US012797460B2

(12) United States Patent
Dormitzer et al.

(10) Patent No.: US 12,797,460 B2
(45) Date of Patent: Nov. 17, 2026

(54) IMMUNOGENIC COMPOSITION AGAINST INFLUENZA

(71) Applicant: PFIZER INC., New York, NY (US)

(72) Inventors: Philip Ralph Dormitzer, Sherborn, MA (US); Advait Vijay Badkar, Westford, MA (US); Christina Van Geen Hoven, Boxford, MA (US); Kathrin Ute Jansen, New York, NY (US); Pirada Suphaphiphat Allen, Congers, NY (US); Ramin Darvari, Lexington, MA (US); Mark Duda, Lynn, MA (US)

(73) Assignee: PFIZER INC., New York, NY (US)

( * ) Notice: Subject to any disclaimer, the term of this patent is extended or adjusted under 35 U.S.C. 154(b) by 1031 days.

(21) Appl. No.: 17/733,566

(22) Filed: Apr. 29, 2022

(65) Prior Publication Data

US 2022/0362372 A1 Nov. 17, 2022

Related U.S. Application Data

(60) Provisional application No. 63/261,784, filed on Sep. 28, 2021, provisional application No. 63/197,325, filed on Jun. 4, 2021, provisional application No. 63/184,201, filed on May 4, 2021, provisional application No. 63/183,624, filed on May 3, 2021.

(51) Int. Cl.

*A61K 39/145* (2006.01)
*A61P 31/16* (2006.01)
*A61K 39/00* (2006.01)

(52) U.S. Cl.

CPC ............ *A61K 39/145* (2013.01); *A61P 31/16* (2018.01); *A61K 2039/53* (2013.01); *A61K 2039/6018* (2013.01); *A61K 2039/70* (2013.01)

(58) Field of Classification Search

CPC ........ A61K 2039/6018; A61K 2039/70; A61K 39/12; A61K 39/145; A61K 2039/53; A61K 2039/55555; A61K 9/5123; A61P 31/16; C12N 2760/16134

See application file for complete search history.

(56) References Cited

U.S. PATENT DOCUMENTS

| | | | | |
|---|---|---|---|---|
| 2019/0015501 | A1 | 1/2019 | Ciaramella et al. | |
| 2023/0181715 | A1* | 6/2023 | Pardi ....................... | A61P 31/22 424/498 |
| 2024/0150386 | A1 | 5/2024 | Heinz et al. | |

FOREIGN PATENT DOCUMENTS

| | | | |
|---|---|---|---|
| RU | 2018118337 | A | 11/2019 |
| RU | 2746406 | C2 | 4/2021 |
| RU | 2020117848 | A | 12/2021 |
| WO | 2018/078053 | A1 | 5/2018 |
| WO | 2022043551 | A2 | 3/2022 |
| WO | 2022/099003 | A1 | 5/2022 |
| WO | 2022/234417 | A1 | 11/2022 |

OTHER PUBLICATIONS

Buschmann et al, "Nanomaterial Delivery Systems for mRNA Vaccines", Vaccines, 9(1): 65 (30 pages) (2021).
Chaudhary et al, "mRNA vaccines for infectious diseases: principles, delivery and clinical translation", Nature Reviews Drug Discovery, 20(11):817-838 (2021).
Freyn et al, "A Multi-Targeting, Nucleoside-Modified mRNA Influenza Virus Vaccine Provides Broad Protection in Mice", Molecular Therapy, 28(7):1569-1584 (2020).
Polack et al, "Safety and Efficacy of the BNT162b2 mRNA Covid-19 Vaccine", The New England Journal of Medicine, 383(27):2603-2615 (2020).
Zhuang et al, "mRNA Vaccines Encoding the HA Protein of Influenza A H1N1 Virus Delivered by Cationic Lipid Nanoparticles Induce Protective Immune Responses in Mice", Vaccines, 8(1): 123 (17 pages) (2020).

* cited by examiner

*Primary Examiner* — Bao Q Li
(74) *Attorney, Agent, or Firm* — Pfizer Inc.

(57) ABSTRACT

The invention relates to compositions and methods for the preparation, manufacture and therapeutic use ribonucleic acid vaccines comprising polynucleotide molecules encoding one or more influenza antigens, such as hemagglutinin antigens.

22 Claims, No Drawings

Specification includes a Sequence Listing.

SEQUENCE LISTING

```
<160> NUMBER OF SEQ ID NOS: 8

<210> SEQ ID NO 1
<211> LENGTH: 52
<212> TYPE: RNA
<213> ORGANISM: Artificial Sequence
<220> FEATURE:
<223> OTHER INFORMATION: Synthetic construct

<400> SEQUENCE: 1

gaauaaacua guauucuucu ggucccccaca gacucagaga gaacccgcca cc              52


<210> SEQ ID NO 2
<211> LENGTH: 295
<212> TYPE: RNA
<213> ORGANISM: Artificial Sequence
<220> FEATURE:
<223> OTHER INFORMATION: Synthetic construct

<400> SEQUENCE: 2

cucgagcugg uacugcaugc acgcaaugcu agcugccccu uucccguccu ggguaccccg        60

agucuccccc gaccucgggu cccagguaug cucccaccuc caccugcccc acucaccacc       120

ucugcuaguu ccagacaccu cccaagcacg cagcaaugca gcucaaaacg cuuagccuag       180

ccacaccccc acgggaaaca gcagugauua accuuuagca auaaacgaaa guuuaacuaa       240

gcuauacuaa ccccaggguu ggucaauuuc gugccagcca cacccuggag cuagc            295


<210> SEQ ID NO 3
<211> LENGTH: 110
<212> TYPE: RNA
<213> ORGANISM: Artificial Sequence
<220> FEATURE:
<223> OTHER INFORMATION: Synthetic construct

<400> SEQUENCE: 3

aaaaaaaaaa aaaaaaaaaa aaaaaaaaaa gcauaugacu aaaaaaaaaa aaaaaaaaaa        60

aaaaaaaaaa aaaaaaaaaa aaaaaaaaaa aaaaaaaaaa aaaaaaaaaa                  110


<210> SEQ ID NO 4
<211> LENGTH: 45
<212> TYPE: DNA
<213> ORGANISM: Artificial Sequence
<220> FEATURE:
<223> OTHER INFORMATION: Synthetic construct

<400> SEQUENCE: 4

aataaactag tattcttctg gtccccacag actcagagag aaccc                        45


<210> SEQ ID NO 5
<211> LENGTH: 54
<212> TYPE: RNA
<213> ORGANISM: Artificial Sequence
<220> FEATURE:
<223> OTHER INFORMATION: Synthetic construct
```

<400> SEQUENCE: 5
gagaauaaac uaguauucuu cugguccccca cagacucaga gagaacccgc cacc 54

<210> SEQ ID NO 6
<211> LENGTH: 47
<212> TYPE: DNA
<213> ORGANISM: Artificial Sequence
<220> FEATURE:
<223> OTHER INFORMATION: Synthetic construct

<400> SEQUENCE: 6
agaataaact agtattcttc tggtccccac agactcagag agaaccc 47

<210> SEQ ID NO 7
<211> LENGTH: 295
<212> TYPE: RNA
<213> ORGANISM: Artificial Sequence
<220> FEATURE:
<223> OTHER INFORMATION: Synthetic construct

<400> SEQUENCE: 7
cucgagcugg uacugcaugc acgcaaugcu agcugccccu uucccguccu ggguaccccg 60
agucuccccc gaccucgggu cccagguaug cucccaccuc caccugcccc acucaccacc 120
ucugcuaguu ccagacaccu cccaagcacg cagcaaugca gcucaaaacg cuuagccuag 180
ccacaccccc acgggaaaca gcagugauua accuuuagca auaaacgaaa guuuaacuaa 240
gcuauacuaa ccccaggguu ggucaauuuc gugccagcca cacccuggag cuagc 295

<210> SEQ ID NO 8
<211> LENGTH: 295
<212> TYPE: RNA
<213> ORGANISM: Artificial Sequence
<220> FEATURE:
<223> OTHER INFORMATION: Synthetic construct

<400> SEQUENCE: 8
cucgagcugg uacugcaugc acgcaaugcu agcugccccu uucccguccu ggguaccccg 60
agucuccccc gaccucgggu cccagguaug cucccaccuc caccugcccc acucaccacc 120
ucugcuaguu ccagacaccu cccaagcacg cagcaaugca gcucaaaacg cuuagccuag 180
ccacaccccc acgggaaaca gcagugauua accuuuagca auaaacgaaa guuuaacuaa 240
gcuauacuaa ccccaggguu ggucaauuuc gugccagcca cacccuggag cuagc 295

IMMUNOGENIC COMPOSITION AGAINST INFLUENZA

RELATED APPLICATIONS

This application claims priority to each of the following applications, the disclosure of each of which is hereby incorporated by reference in its entirety: U.S. Provisional Patent Application 63/183,624, filed on May 3, 2021; U.S. Provisional Patent Application 63/184,201, filed on May 4, 2021; U.S. Provisional Patent Application 63/197,325, filed on Jun. 4, 2021; and U.S. Provisional Patent Application 63/261,784, filed on Sep. 28, 2021.

FIELD

The invention relates to compositions and methods for the preparation, manufacture and therapeutic use of ribonucleic acid vaccines comprising polynucleotide molecules encoding one or more influenza antigens, such as hemagglutinin antigens.

BACKGROUND

Influenza viruses are members of the orthomyxoviridae family, and are classified into three types (A, B, and C), based on antigenic differences between their nucleoprotein (NP) and matrix (M) protein.

The genome of influenza A virus includes eight molecules (seven for influenza C virus) of linear, negative polarity, single-stranded RNAs, which encode several polypeptides including: the RNA-directed RNA polymerase proteins (PB2, PB1 and PA) and nucleoprotein (NP), which form the nucleocapsid; the matrix proteins (M1, M2, which is also a surface-exposed protein embedded in the virus membrane); two surface glycoproteins, which project from the lipoprotein envelope: hemagglutinin (HA) and neuraminidase (NA); and nonstructural proteins (NS1 and NS2). Hemagglutinin is the major envelope glycoprotein of influenza A and B viruses, and hemagglutinin-esterase (HE) of influenza C viruses is a protein homologous to HA.

A challenge for therapy and prophylaxis against influenza and other infections using traditional vaccines is the limitation of vaccines in breadth, providing protection only against closely related subtypes. In addition, the length of time required to complete current standard influenza virus vaccine production processes inhibits the rapid development and production of an adapted vaccine in a pandemic situation.

There is a need for improved immunogenic compositions against influenza.

SUMMARY

The unmet needs for improved immunogenic compositions against influenza, among other things, are provided herein. In one aspect, the disclosure relates to an immunogenic composition including: (i) a first ribonucleic acid (RNA) polynucleotide having an open reading frame encoding a first antigen, said antigen including at least one influenza virus antigenic polypeptide or an immunogenic fragment thereof, and (ii) a second RNA polynucleotide having an open reading frame encoding a second antigen, said second antigen including at least one influenza virus antigenic polypeptide or an immunogenic fragment thereof, wherein the first and second RNA polynucleotides are formulated in a lipid nanoparticle (LNP). In some embodiments, the first and second antigens include hemagglutinin (HA), or an immunogenic fragment or variant thereof. In some embodiments, the first antigen includes an HA from a different subtype of influenza virus to the influenza virus antigenic polypeptide or an immunogenic fragment thereof of the second antigen. In some embodiments, the composition further includes (iii) a third antigen including at least one influenza virus antigenic polypeptide or an immunogenic fragment thereof, wherein the third antigen is from influenza virus but is from a different strain of influenza virus to both the first and second antigens. In some embodiments, the first, second and third RNA polynucleotides are formulated in a lipid nanoparticle. In some embodiments, the composition further includes (iv) a fourth RNA polynucleotide having an open reading frame encoding a fourth antigen, said antigen including at least one influenza virus antigenic polypeptide or an immunogenic fragment thereof, wherein the fourth antigen is from influenza virus but is from a different strain of influenza virus to the first, second and third antigens. In some embodiments, the first, second, third, and fourth RNA polynucleotides are formulated in a lipid nanoparticle.

In some embodiments, each RNA polynucleotide includes a modified nucleotide. In some embodiments, the modified nucleotide is selected from the group consisting of pseudouridine, 1-methylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, and 2'—O-methyl uridine.

In some embodiments, each RNA polynucleotide includes a 5' terminal cap, a 5' UTR, a 3'UTR, and a 3' polyadenylation tail. In some embodiments, the 5' terminal cap includes:

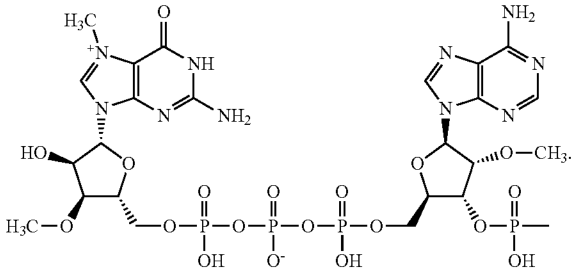

In some embodiments, the 5' UTR includes SEQ ID NO: 1. In some embodiments, the 3' UTR includes SEQ ID NO: 2. In some embodiments, the 3' polyadenylation tail includes SEQ ID NO: 3.

In some embodiments, the RNA polynucleotide has an integrity greater than 85%. In some embodiments, the RNA polynucleotide has a purity of greater than 85%. In some embodiments, the lipid nanoparticle includes 20-60 mol % ionizable cationic lipid, 5-25 mol % neutral lipid, 25-55 mol % cholesterol, and 0.5-5 mol % PEG-modified lipid.

In some embodiments, the cationic lipid includes:

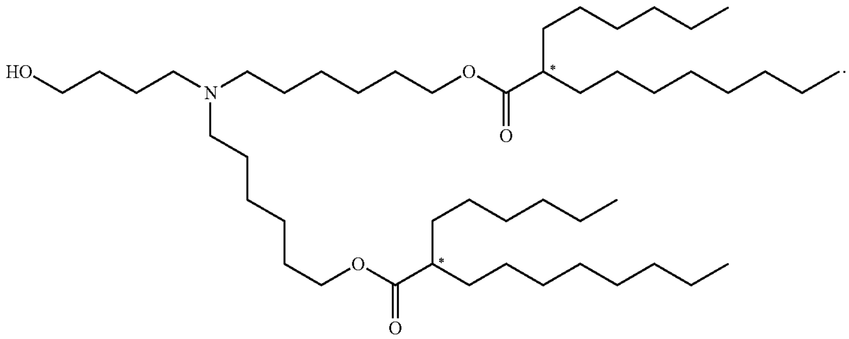

Asterisks (*) indicate chiral centers.

In some embodiments, the PEG-modified lipid includes:

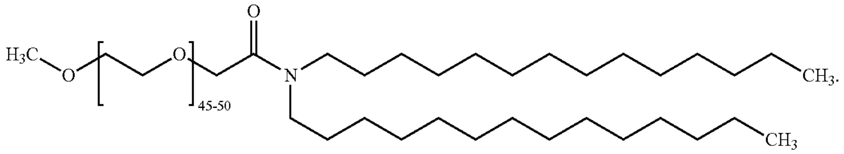

In some embodiments, the first antigen is HA from influenza A subtype H1 or an immunogenic fragment or variant thereof and the second antigen is HA from a different H1 strain to the first antigen or an immunogenic fragment or variant thereof. In some embodiments, the first and second antigens are HA from influenza A subtype H3 or an immunogenic fragment or variant thereof and wherein both antigens are derived from different strains of H3 influenza virus.

In some embodiments, the first and second antigens are HA from influenza A subtype H1 or an immunogenic fragment or variant thereof and the third and fourth antigens are from influenza A subtype H3 or an immunogenic fragment or variant thereof and wherein the first and second antigens are derived from different strains of H1 virus and the third and fourth antigens are from different strains of H3 influenza virus.

In some embodiments, at least the first and second RNA polynucleotides are formulated in a single lipid nanoparticle. In some embodiments, the first and second RNA polynucleotides are formulated in a single lipid nanoparticle. In some embodiments, the first, second, and third RNA polynucleotides are formulated in a single lipid nanoparticle. In some embodiments, the first, second, third, and fourth RNA polynucleotides are formulated in a single LNP.

In some embodiments, each of the RNA polynucleotides is formulated in a single LNP, wherein each single LNP encapsulates the RNA polynucleotide encoding one antigen. In some embodiments, the first RNA polynucleotide is formulated in a first LNP; and the second RNA polynucleotide is formulated in a second LNP. In some embodiments, the first RNA polynucleotide is formulated in a first LNP; the second RNA polynucleotide is formulated in a second LNP; and the third RNA polynucleotide is formulated in a third LNP. In some embodiments, the first RNA polynucleotide is formulated in a first LNP; the second RNA polynucleotide is formulated in a second LNP; the third RNA polynucleotide is formulated in a third LNP; and the fourth RNA polynucleotide is formulated in a fourth LNP.

In another aspect, the disclosure relates to any of the immunogenic compositions described herein, for use in the eliciting an immune response against influenza.

In another aspect, the disclosure relates to a method of eliciting an immune response against influenza disease, including administering an effective amount of any of the immunogenic compositions described herein.

In another aspect, the disclosure relates to a method of purifying an RNA polynucleotide synthesized by in vitro transcription. The method includes ultrafiltration and diafiltration. In some embodiments, the method does not comprise a chromatography step. In some embodiments, the purified RNA polynucleotide is substantially free of contaminants comprising short abortive RNA species, long abortive RNA species, double- stranded RNA (dsRNA), residual plasmid DNA, residual in vitro transcription enzymes, residual solvent and/or residual salt. In some embodiments, the residual plasmid DNA is ≤500 ng DNA/mg RNA. In some embodiments, the yield of the purified mRNA is about 70% to about 99%. In some embodiments, purity of the purified mRNA is between about 60% and about 100%. In some embodiments, purity of the purified mRNA is between about 85%-95%.

DETAILED DESCRIPTION

Embodiments of the present disclosure provide RNA (e.g., mRNA) vaccines that include polynucleotide encoding an influenza virus antigen. Influenza virus RNA vaccines, as provided herein may be used to induce a balanced immune response, comprising both cellular and humoral immunity, without many of the risks associated with DNA vaccination. In some embodiments, the virus is a strain of Influenza A or Influenza B or combinations thereof.

In one aspect, the disclosure relates to an immunogenic composition including: (i) a first ribonucleic acid (RNA) polynucleotide having an open reading frame encoding a first antigen, said antigen including at least one influenza virus antigenic polypeptide or an immunogenic fragment thereof, and (ii) a second RNA polynucleotide having an open reading frame encoding a second antigen, said second antigen including at least one influenza virus antigenic polypeptide or an immunogenic fragment thereof, wherein the first and second RNA polynucleotides are formulated in a lipid nanoparticle (LNP). In some embodiments, the first and second antigens include hemagglutinin (HA), or an immunogenic fragment or variant thereof. In some embodiments, the first antigen includes an HA from a different subtype of influenza virus to the influenza virus antigenic polypeptide or an immunogenic fragment thereof of the second antigen. In some embodiments, the composition further includes (iii) a third antigen including at least one influenza virus antigenic polypeptide or an immunogenic fragment thereof, wherein the third antigen is from influenza virus but is from a different strain of influenza virus to both the first and second antigens. In some embodiments, the first, second and third RNA polynucleotides are formulated in a lipid nanoparticle.

In some embodiments, the composition further includes (iv) a fourth RNA polynucleotide having an open reading frame encoding a fourth antigen, said antigen including at least one influenza virus antigenic polypeptide or an immunogenic fragment thereof, wherein the fourth antigen is from influenza virus but is from a different strain of influenza virus to the first, second and third antigens. In some embodiments, the first, second, third, and fourth RNA polynucleotides are formulated in a lipid nanoparticle.

In some embodiments, the RNA polynucleotides are mixed in desired ratios in a single vessel and are subsequently formulated into lipid nanoparticles. The inventors surprisingly discovered that the initial input of different RNA polynucleotides at a known ratio to be formulated in a single LNP process surprisingly resulted in LNPs encapsulating the different RNA polynucleotides in about the same ratio as the input ratio. The results were surprising in view of the potential for the manufacturing process to favor one RNA polynucleotide to another when encapsulating the RNA polynucleotides into an LNP. Such embodiments may be referred herein as “pre-mix”. Accordingly, in some embodiments, first and second RNA polynucleotides are formulated in a single lipid nanoparticle. In some embodiments, the first, second, third, and fourth RNA polynucleotides are formulated in a single LNP. In some embodiments, the first, second, third, fourth, and fifth RNA polynucleotides are formulated in a single LNP. In some embodiments, the first, second, third, fourth, fifth, and sixth RNA polynucleotides are formulated in a single LNP. In some embodiments, the first, second, third, fourth, fifth, sixth, and seventh RNA polynucleotides are formulated in a single LNP. In some embodiments, the first, second, third, fourth, fifth, sixth, seventh, and eighth RNA polynucleotides are formulated in a single LNP.

In some embodiments, the molar ratio of the first RNA polynucleotide to the second RNA polynucleotide in the mix of RNA polynucleotides prior to formulation into LNPs is about 1:50, about 1:25, about 1:10, about 1:5, about 1:4, about 1:3, about 1:2, about 1:1, about 2:1, about 3:1, about 4:1, or about 5:1, about 10:1, about 25:1 or about 50:1. In some embodiments, the molar ratio of the first RNA polynucleotide to the second RNA polynucleotide is greater than 1:1.

In some embodiments, the molar ratio of the first RNA polynucleotide to the third RNA polynucleotide in the mix of RNA polynucleotides prior to formulation into LNPs is about 1:50, about 1:25, about 1: 10, about 1:5, about 1:4, about 1:3, about 1:2, about 1:1, about 2:1, about 3:1, about 4:1, or about 5:1, about 10:1, about 25:1 or about 50:1. In some embodiments, the molar ratio of the first RNA polynucleotide to the third RNA polynucleotide is greater than 1:1.

In some embodiments, the molar ratio of the first RNA polynucleotide to the fourth RNA polynucleotide in the mix of RNA polynucleotides prior to formulation into LNPs is about 1:50, about 1:25, about 1:10, about 1:5, about 1:4, about 1:3, about 1:2, about 1:1, about 2:1, about 3:1, about 4:1, or about 5:1, about 10:1, about 25:1 or about 50:1. In some embodiments, the molar ratio of the first RNA polynucleotide to the fourth RNA polynucleotide is greater than 1:1. In some embodiments, the molar ratio of the first RNA polynucleotide to the fifth RNA polynucleotide in the mix of RNA polynucleotides prior to formulation into LNPs is about 1:50, about 1:25, about 1:10, about 1:5, about 1:4, about 1:3, about 1:2, about 1:1, about 2:1, about 3:1, about 4:1, or about 5:1, about 10:1, about 25:1 or about 50:1. In some embodiments, the molar ratio of the first RNA polynucleotide to the fifth RNA polynucleotide is greater than 1:1. In some embodiments, the molar ratio of the first RNA polynucleotide to the sixth RNA polynucleotide in the mix of RNA polynucleotides prior to formulation into LNPs is about 1:50, about 1:25, about 1:10, about 1:5, about 1:4, about 1:3, about 1:2, about 1:1, about 2:1, about 3:1, about 4:1, or about 5:1, about 10:1, about 25:1 or about 50:1. In some embodiments, the molar ratio of the first RNA polynucleotide to the sixth RNA polynucleotide is greater than 1:1. In some embodiments, the molar ratio of the first RNA polynucleotide to the seventh RNA polynucleotide in the mix of RNA polynucleotides prior to formulation into LNPs is about 1:50, about 1:25, about 1:10, about 1:5, about 1:4, about 1:3, about 1:2, about 1:1, about 2:1, about 3:1, about 4:1, or about 5:1, about 10:1, about 25:1 or about 50:1. In some embodiments, the molar ratio of the first RNA polynucleotide to the seventh RNA polynucleotide is greater than 1:1. In some embodiments, the molar ratio of the first RNA polynucleotide to the eighth RNA polynucleotide in the mix of RNA polynucleotides prior to formulation into LNPs is about 1:50, about 1:25, about 1:10, about 1:5, about 1:4, about 1:3, about 1:2, about 1:1, about 2:1, about 3:1, about 4:1, or about 5:1, about 10:1, about 25:1 or about 50:1. In some embodiments, the molar ratio of the first RNA polynucleotide to the eighth RNA polynucleotide is greater than 1:1.

In alternative embodiments, each RNA polynucleotide encoding a particular antigen is formulated in an individual LNP, such that each LNP encapsulates an RNA polynucleotide encoding identical antigens. Such embodiments may be referred herein as “post-mix”. Accordingly, in some embodiments, the first RNA polynucleotide is formulated in a first LNP; the second RNA polynucleotide is formulated in a second LNP; the third RNA polynucleotide is formulated in a third LNP; the fourth RNA polynucleotide is formulated in a fourth LNP; the fifth RNA polynucleotide is formulated in a fifth LNP; the sixth RNA polynucleotide is formulated in a sixth LNP; the seventh RNA polynucleotide is formulated in a seventh LNP; and the eighth RNA polynucleotide is formulated in an eighth LNP.

In some embodiments, the molar ratio of the first LNP to the second LNP in the mix of LNPs prior to formulation into LNPs is about 1:50, about 1:25, about 1:0, about 1:5, about 1:4, about 1:3, about 1:2, about 1:1, about 2:1, about 3:1, about 4:1, or about 5:1, about 10:1, about 25:1 or about 50:1. In some embodiments, the molar ratio of the first LNP to the second LNP is greater than 1:1.

In some embodiments, the molar ratio of the first LNP to the third LNP in the mix of LNPs prior to formulation into LNPs is about 1:50, about 1:25, about 1:10, about 1:5, about 1:4, about 1:3, about 1:2, about 1:1, about 2:1, about 3:1, about 4:1, or about 5:1, about 10:1, about 25:1 or about 50:1. In some embodiments, the molar ratio of the first LNP to the third LNP is greater than 1:1.

In some embodiments, the molar ratio of the first LNP to the fourth LNP in the mix of LNPs prior to formulation into LNPs is about 1:50, about 1:25, about 1:10, about 1:5, about 1:4, about 1:3, about 1:2, about 1:1, about 2:1, about 3:1, about 4:1, or about 5:1, about 10:1, about 25:1 or about 50:1. In some embodiments, the molar ratio of the first LNP to the fourth LNP is greater than 1:1. In some embodiments, the molar ratio of the first LNP to the fifth LNP in the mix of LNPs prior to formulation into LNPs is about 1:50, about 1:25, about 1: 10, about 1:5, about 1:4, about 1:3, about 1:2, about 1:1, about 2:1, about 3:1, about 4:1, or about 5:1, about 10:1, about 25:1 or about 50:1. In some embodiments, the molar ratio of the first LNP to the fifth LNP is greater than 1:1. In some embodiments, the molar ratio of the first LNP to the sixth LNP in the mix of LNPs prior to formulation into LNPs is about 1:50, about 1:25, about 1:10, about 1:5, about 1:4, about 1:3, about 1:2, about 1:1, about 2:1, about 3:1, about 4:1, or about 5:1, about 10:1, about 25:1 or about 50:1. In some embodiments, the molar ratio of the first LNP to the sixth LNP is greater than 1:1. In some embodiments, the molar ratio of the first LNP to the seventh LNP in the mix of LNPs prior to formulation into LNPs is about 1:50, about 1:25, about 1:10, about 1:5, about 1:4, about 1:3, about 1:2, about 1:1, about 2:1, about 3:1, about 4:1, or about 5:1, about 10:1, about 25:1 or about 50:1. In some embodiments, the molar ratio of the first LNP to the seventh LNP is greater than 1:1. In some embodiments, the molar ratio of the first LNP to the eighth LNP in the mix of LNPs prior to formulation into LNPs is about 1:50, about 1:25, about 1:10, about 1:5, about 1:4, about 1:3, about 1:2, about 1:1, about 2:1, about 3:1, about 4:1, or about 5:1, about 10:1, about 25:1 or about 50:1. In some embodiments, the molar ratio of the first LNP to the eighth LNP is greater than 1:1.

Surprisingly, the inventors discovered that regardless of the process, the resulting ratio of RNA polynucleotide was comparable whether the plurality of RNA polynucleotides are mixed prior to formulation in an LNP (pre-mixed) or whether the RNA polynucleotides encoding a particular antigen is formulated in an individual LNP and the plurality of LNPs for different antigens are mixed (post-mixed). As a result of the discovery, there may be an option for medical professionals to mix and administer different ratios of antigens depending on the influenza season, particularly when the individual LNPs encapsulate RNA for a single antigen.

In some embodiments, the antigenic polypeptide encodes a hemagglutinin protein or immunogenic fragment thereof. In some embodiments, the hemagglutinin protein is H1, H2, H3, H4, H5, H6, H7, H8, H9, H10, H11, H12, H13, H14, H15, H16, H17, H18, or an immunogenic fragment thereof. In some embodiments, the hemagglutinin protein does not comprise a head domain. In some embodiments, the hemagglutinin protein comprises a portion of the head domain. In some embodiments, the hemagglutinin protein does not comprise a cytoplasmic domain. In some embodiments, the hemagglutinin protein comprises a portion of the cytoplasmic domain. In some embodiments, the truncated hemagglutinin protein comprises a portion of the transmembrane domain.

Some embodiments provide influenza vaccines comprising one or more RNA polynucleotides having an open reading frame encoding a hemagglutinin protein and a pharmaceutically acceptable carrier or excipient, formulated within a cationic lipid nanoparticle. In some embodiments, the hemagglutinin protein is selected from H1, H7 and H10. In some embodiments, the RNA polynucleotide further encodes neuraminidase (NA) protein. In some embodiments, the hemagglutinin protein is derived from a strain of Influenza A virus or Influenza B virus or combinations thereof. In some embodiments, the Influenza virus is selected from H1N1, H3N2, H7N9, and H10N8.

In some embodiments, the virus is a strain of Influenza A or Influenza B or combinations thereof. In some embodiments, the strain of Influenza A or Influenza B is associated with birds, pigs, horses, dogs, humans, or non-human primates. In some embodiments, the antigenic polypeptide encodes a hemagglutinin protein or fragment thereof. In some embodiments, the hemagglutinin protein is H7 or H10 or a fragment thereof. In some embodiments, the hemagglutinin protein comprises a portion of the head domain (HA1). In some embodiments, the hemagglutinin protein comprises a portion of the cytoplasmic domain. In some embodiments, the truncated hemagglutinin protein. In some embodiments, the protein is a truncated hemagglutinin protein comprises a portion of the transmembrane domain. In some embodiments, the virus is selected from the group consisting of H7N9 and H10N8. Protein fragments, functional protein domains, and homologous proteins are also considered to be within the scope of polypeptides of interest. For example, provided herein is any protein fragment (meaning a polypeptide sequence at least one amino acid residue shorter than a reference polypeptide sequence but otherwise identical) of a reference protein 10, 20, 30, 40, 50, 60, 70, 80, 90, 100 or greater than 100 amino acids in length.

In some embodiments, an Influenza RNA composition includes an RNA encoding an antigenic fusion protein. Thus, the encoded antigen or antigens may include two or more proteins (e.g., protein and/or protein fragment) joined together. Alternatively, the protein to which a protein antigen is fused does not promote a strong immune response to itself, but rather to the influenza antigen. Antigenic fusion proteins, in some embodiments, retain the functional property from each original protein.

Some embodiments provide methods of preventing or treating influenza viral infection comprising administering to a subject any of the vaccines described herein. In some embodiments, the antigen specific immune response comprises a T cell response. In some embodiments, the antigen specific immune response comprises a B cell response. In some embodiments, the antigen specific immune response comprises both a T cell response and a B cell response. In some embodiments, the method of producing an antigen specific immune response involves a single administration of the vaccine. In some embodiments, the vaccine is administered to the subject by intradermal, intramuscular injection, subcutaneous injection, intranasal inoculation, or oral administration.

In some embodiments, the RNA (e.g., mRNA) polynucleotides or portions thereof may encode one or more polypeptides or fragments thereof of an influenza strain as an antigen.

1. mRNA Vaccines of the Disclosure

The present disclosure relates to mRNA vaccines in general. Several mRNA vaccine platforms are available in the prior art. The basic structure of in vitro transcribed (IVT) mRNA closely resembles "mature" eukaryotic mRNA and includes (i) a protein-encoding open reading frame (ORF), flanked by (ii) 5' and 3' untranslated regions (UTRs), and at the end sides (iii) a 7-methyl guanosine 5' cap structure and (iv) a 3' poly(A) tail. The non-coding structural features play important roles in the pharmacology of mRNA and can be individually optimized to modulate the mRNA stability, translation efficiency, and immunogenicity. By incorporating modified nucleosides, mRNA transcripts referred to as "nucleoside-modified mRNA" can be produced with reduced immunostimulatory activity, and therefore an improved safety profile can be obtained. In addition, modified nucleosides allow the design of mRNA vaccines with strongly enhanced stability and translation capacity, as they can avoid the direct antiviral pathways that are induced by type IFNs and are programmed to degrade and inhibit invading mRNA. For instance, the replacement of uridine with pseudouridine in IVT mRNA reduces the activity of 2'-5'-oligoadenylate synthetase, which regulates the mRNA cleavage by RNase L. In addition, lower activities are measured for protein kinase R, an enzyme that is associated with the inhibition of the mRNA translation process.

Besides the incorporation of modified nucleotides, other approaches have been validated to increase the translation capacity and stability of mRNA. One example is the development of "sequence-engineered mRNA". Here, mRNA expression can be strongly increased by sequence optimizations in the ORF and UTRs of mRNA, for instance by enriching the GC content, or by selecting the UTRs of natural long-lived mRNA molecules. Another approach is the design of "self-amplifying mRNA" constructs. These are mostly derived from alphaviruses and contain an ORF that is replaced by the antigen of interest together with an additional ORF encoding viral replicase. The latter drives the intracellular amplification of mRNA and can therefore significantly increase the antigen expression capacity.

Also, several modifications have been implemented at the end structures of mRNA. Anti-reverse cap (ARCA) modifications can ensure the correct cap orientation at the 5' end, which yields almost complete fractions of mRNA that can efficiently bind the ribosomes. Other cap modifications, such as phosphorothioate cap analogs, can further improve the affinity towards the eukaryotic translation initiation factor 4E, and increase the resistance against the RNA decapping complex.

Conversely, by modifying its structure, the potency of mRNA to trigger innate immune responses can be further improved, but to the detriment of translation capacity. By stabilizing the mRNA with either a phosphorothioate backbone, or by its precipitation with the cationic protein protamine, antigen expression can be diminished, but stronger immune-stimulating capacities can be obtained.

In one aspect the invention relates to an immunogenic composition comprising an mRNA molecule that encodes one or more polypeptides or fragments thereof of an influenza strain as an antigen.

In some embodiments, the mRNA molecule comprises a nucleoside-modified mRNA. mRNA useful in the disclosure typically include a first region of linked nucleosides encoding a polypeptide of interest (e.g., a coding region), a first flanking region located at the 5'-terminus of the first region (e.g., a 5-UTR), a second flanking region located at the 3'-terminus of the first region (e.g., a 3-UTR), at least one 5'-cap region, and a 3'-stabilizing region. In some embodiments, the mRNA of the disclosure further includes a poly-A region or a Kozak sequence (e.g., in the 5'-UTR). In some cases, mRNA of the disclosure may contain one or more intronic nucleotide sequences capable of being excised from the polynucleotide. In some embodiments, mRNA of the disclosure may include a 5' cap structure, a chain terminating nucleotide, a stem loop, a poly A sequence, and/or a polyadenylation signal. Any one of the regions of a nucleic acid may include one or more alternative components (e.g., an alternative nucleoside). For example, the 3'-stabilizing region may contain an alternative nucleoside such as an L-nucleoside, an inverted thymidine, or a 2'-0-methyl nucleoside and/or the coding region, 5'-UTR, 3'-UTR, or cap region may include an alternative nucleoside such as a 5-substituted uridine (e.g., 5-methoxyuridine), a 1-substituted pseudouridine (e.g., 1-methyl-pseudouridine), and/or a 5-substituted cytidine (e.g., 5-methyl-cytidine).

The compositions described herein comprise at least one RNA polynucleotide, such as a mRNA (e.g., modified mRNA). mRNA, for example, is transcribed in vitro from template DNA, referred to as an "in vitro transcription template." In some embodiments, an in vitro transcription template encodes a 5' untranslated (UTR) region, contains an open reading frame, and encodes a 3' UTR and a polyA tail. The particular nucleic acid sequence composition and length of an in vitro transcription template will depend on the mRNA encoded by the template.

A "5' untranslated region" (UTR) refers to a region of an mRNA that is directly upstream (i.e., 5') from the start codon (i.e., the first codon of an mRNA transcript translated by a ribosome) that does not encode a polypeptide.

In preferred embodiments, the 5' UTR comprises SEQ ID NO: 1.

A "3' untranslated region" (UTR) refers to a region of an mRNA that is directly downstream (i.e., 3') from the stop codon (i.e., the codon of an mRNA transcript that signals a termination of translation) that does not encode a polypeptide.

In preferred embodiments, the 3' UTR comprises SEQ ID NO: 2.

An "open reading frame" is a continuous stretch of DNA beginning with a start codon (e.g., methionine (ATG)), and ending with a stop codon (e.g., TAA, TAG or TGA) and encodes a polypeptide.

A "polyA tail" is a region of mRNA that is downstream, e.g., directly downstream (i.e., 3'), from the 3' UTR that contains multiple, consecutive adenosine monophosphates. A polyA tail may contain 10 to 300 adenosine monophosphates. For example, a polyA tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a polyA tail contains 50 to 250 adenosine monophosphates. In a relevant biological setting (e.g., in cells, in vivo) the poly(A) tail functions to protect mRNA from enzymatic degradation, e.g., in the cytoplasm, and aids in transcription termination, export of the mRNA from the nucleus and translation.

In preferred embodiments, the 3' polyadenylation tail comprises SEQ ID NO: 3.

In some embodiments, a polynucleotide includes 200 to 3,000 nucleotides. For example, a polynucleotide may include 200 to 500, 200 to 1000, 200 to 1500, 200 to 3000, 500 to 1000, 500 to 1500, 500 to 2000, 500 to 3000, 1000 to 1500, 1000 to 2000, 1000 to 3000, 1500 to 3000, or 2000 to 3000 nucleotides).

In some embodiments, a LNP includes one or more RNAs, and the one or more RNAs, lipids, and amounts thereof may be selected to provide a specific N:P ratio. The N:P ratio of the composition refers to the molar ratio of nitrogen atoms in one or more lipids to the number of phosphate groups in an RNA. In general, a lower N:P ratio is preferred. The one or more RNA, lipids, and amounts thereof may be selected to provide an N:P ratio from about 2:1 to about 30:1, such as 2:1, 3:1, 4:1, 5:1, 6:1, 7:1, 8:1, 9:1, 10:1, 12:1, 14:1, 16:1, 18:1, 20:1, 22:1, 24:1, 26:1, 28:1, or 30:1. In certain embodiments, the N:P ratio may be from about 2:1 to about 8:1. In other embodiments, the N:P ratio is from about 5:1 to about 8:1. For example, the N:P ratio may be about 5.0:1, about 5.5 :1, about 5.67:1, about 6.0:1, about 6.5:1, or about 7.0:1. For example, the N:P ratio may be about 5.67:1.

mRNA of the disclosure may include one or more naturally occurring components, including any of the canonical nucleotides A (adenosine), G (guanosine), C (cytosine), U (uridine), or T (thymidine). In one embodiment, all or substantially all of the nucleotides comprising (a) the 5'-UTR, (b) the open reading frame (ORF), (c) the 3'-UTR, (d) the poly A tail, and any combination of (a, b, c, or d above) comprise naturally occurring canonical nucleotides A (adenosine), G (guanosine), C (cytosine), U (uridine), or T (thymidine).

mRNA of the disclosure may include one or more alternative components, as described herein, which impart useful properties including increased stability and/or the lack of a substantial induction of the innate immune response of a cell into which the polynucleotide is introduced. For example, a modRNA may exhibit reduced degradation in a cell into which the modRNA is introduced, relative to a corresponding unaltered mRNA. These alternative species may enhance the efficiency of protein production, intracellular retention of the polynucleotides, and/or viability of contacted cells, as well as possess reduced immunogenicity.

mRNA of the disclosure may include one or more modified (e.g., altered or alternative) nucleobases, nucleosides, nucleotides, or combinations thereof. The mRNA useful in a LNP can include any useful modification or alteration, such as to the nucleobase, the sugar, or the internucleoside linkage (e.g., to a linking phosphate/to a phosphodiester linkage/to the phosphodiester backbone). In certain embodiments, alterations (e.g., one or more alterations) are present in each of the nucleobase, the sugar, and the internucleoside linkage. Alterations according to the present disclosure may be alterations of ribonucleic acids (RNAs), e.g., the substitution of the 2'—OH of the ribofuranosyl ring to 2'—H, threose nucleic acids (TNAs), glycol nucleic acids (GNAs), peptide nucleic acids (PNAs), locked nucleic acids (LNAs), or hybrids thereof. Additional alterations are described herein.

mRNA of the disclosure may or may not be uniformly altered along the entire length of the molecule. For example, one or more or all types of nucleotide (e.g., purine or pyrimidine, or any one or more or all of A, G, U, C) may or may not be uniformly altered in a mRNA, or in a given predetermined sequence region thereof. In some instances, all nucleotides X in a mRNA (or in a given sequence region thereof) are altered, wherein X may any one of nucleotides A, G, U, C, or any one of the combinations A+G, A+U, A+C, G+U, G+C, U+C, A+G+U, A+G+C, G+U+C or A+G+C.

Different sugar alterations and/or internucleoside linkages (e.g., backbone structures) may exist at various positions in a polynucleotide. One of ordinary skill in the art will appreciate that the nucleotide analogs or other alteration(s) may be located at any position(s) of a polynucleotide such that the function of the polynucleotide is not substantially decreased. An alteration may also be a 5'- or 3'-terminal alteration. In some embodiments, the polynucleotide includes an alteration at the 3'-terminus. The polynucleotide may contain from about 1% to about 100% alternative nucleotides (either in relation to overall nucleotide content, or in relation to one or more types of nucleotide, i.e., any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of a canonical nucleotide (e.g., A, G, U, or C).

Polynucleotides may contain at a minimum zero and at maximum 100% alternative nucleotides, or any intervening percentage, such as at least 5% alternative nucleotides, at least 10% alternative nucleotides, at least 25% alternative nucleotides, at least 50% alternative nucleotides, at least 80% alternative nucleotides, or at least 90% alternative nucleotides. For example, polynucleotides may contain an alternative pyrimidine such as an alternative uracil or cytosine. In some embodiments, at least 5%, at least 10%, at least 25%, at least 50%, at least 80%, at least 90% or 100% of the uracil in a polynucleotide is replaced with an alternative uracil (e.g., a 5-substituted uracil). The alternative uracil can be replaced by a compound having a single unique structure or can be replaced by a plurality of compounds having different structures (e.g., 2, 3, 4 or more unique structures). In some instances, at least 5%, at least 10%, at least 25%, at least 50%, at least 80%, at least 90% or 100% of the cytosine in the polynucleotide is replaced with an alternative cytosine (e.g., a 5-substituted cytosine). The alternative cytosine can be replaced by a compound having a single unique structure or can be replaced by a plurality of compounds having different structures (e.g., 2, 3, 4 or more unique structures).

In some instances, nucleic acids do not substantially induce an innate immune response of a cell into which the polynucleotide (e.g., mRNA) is introduced. Features of an induced innate immune response include 1) increased expression of pro-inflammatory cytokines, 2) activation of intracellular PRRs (RIG-I, MDAS, etc., and/or 3) termination or reduction in protein translation.

In some embodiments, the mRNA comprises one or more alternative nucleoside or nucleotides. The alternative nucleosides and nucleotides can include an alternative nucleobase. A nucleobase of a nucleic acid is an organic base such as a purine or pyrimidine or a derivative thereof. A nucleobase may be a canonical base (e.g., adenine, guanine, uracil, thymine, and cytosine). These nucleobases can be altered or wholly replaced to provide polynucleotide molecules having enhanced properties, e.g., increased stability such as resistance to nucleases. Non-canonical or modified bases may include, for example, one or more substitutions or modifications including but not limited to alkyl, aryl, halo, oxo, hydroxyl, alkyloxy, and/or thio substitutions; one or more fused or open rings; oxidation; and/or reduction.

In some embodiments, the nucleobase is an alternative uracil. Exemplary nucleobases and nucleosides having an alternative uracil include pseudouridine (Ψ), pyridin-4- one ribonucleoside, 5-aza-uracil, 6-aza-uracil, 2-thio-5-aza-uracil, 2-thio-uracil (s2U), 4-thio- uracil (s4U), 4-thio-pseudouridine, 2-thio-pseudouridine, 5 -hydroxy -uracil (ho5U), 5-aminoallyl-uracil, 5-halo-uracil (e.g., 5-iodo-uracil or 5-bromo-uracil), 3-methyl-uracil (m U), 5-methoxy-uracil (mo5U), uracil 5-oxyacetic acid (cmo5U), uracil 5-oxyacetic acid methyl ester (mcmo5U), 5-carboxymethyl-uracil (cm5U), 1 -carboxymethyl-pseudouridine, 5-carboxyhydroxymethyl-uracil (chm5U), 5-carboxyhydroxymethyl-uracil methyl ester (mchm5U), 5-methoxycarbonylmethyl-uracil (mcm5U), 5-methoxycarbonylmethyl-2-thio-uracil (mcm5s2U), 5-aminomethyl-2-thio-uracil (nmVu), 5-methylaminomethyl-uracil (mnm5U), 5-methylaminomethyl-2-thio-uracil (mnmVu), 5-methylaminomethyl-2-seleno-uracil (mnm5se2U), 5-carbamoylmethyl-uracil (ncm5U), 5-carboxymethylaminomethyl-uracil (cmnm5U), 5- carboxymethylaminomethyl-2-thio-uracil (cmnmVu), 5-propynyl-uracil, 1- propynyl-pseudouracil, 5-taurinomethyl-uracil (xm5U), 1-taurinomethyl-pseudouridine, 5- taurinomethyl-2-thio-uracil(xm5s2U), 1 -taurinomethyl-4-thio-pseudouridine, 5-methyl-uracil (m5U, i.e., having the nucleobase deoxythymine), 1-methyl-pseudouridine (mV), 5-methyl-2-thio-uracil (m5s2U), l-methyl-4-thio-pseudouridine (m xj/), 4-thio- 1-methyl-pseudouridine, 3- methyl-pseudouridine (m \l/), 2 -thio- 1-methyl-pseudouridine, 1 -methyl- 1-deaza-pseudouri dine, 2-thio-I -methyl- 1-deaza-pseudouri dine, dihydrouracil (D), dihydropseudouridine, 5,6- dihydrouracil, 5-methyl-dihydrouracil (m5D), 2-thio-dihydrouracil, 2-thio-dihydropseudouridine, 2-methoxy-uracil, 2-methoxy-4-thio-uracil, 4-methoxy-pseudouridine, 4-methoxy -2-thio-pseudouridine, N1-methyl-pseudouridine, 3-(3-amino-3- carboxypropyl)uracil (acp U), l-methyl-3-(3-amino-3-carboxypropyl)pseudouridine (acp Ψ), 5-(isopentenylaminomethyl)uracil (inm5U), 5-(isopentenylaminomethyl)-2-thio-uracil (inm5s2U), 5,2'-0-dimethyl-uridine (m5Um), 2-thio-2'-0_methyl-uridine (s2Um), 5-methoxycarbonylmethyl-2'-0- methyl-uridine (mem Um), 5-carbamoylmethyl-2'-0-methyl- uridine (ncm5Um), 5-carboxymethylaminomethyl-2'-0-methyl-uridine (cmnm5Um), 3,2'-0- dimethyl-uridine (m Um), and 5-(isopentenylaminomethyl)-2'-0-methyl-uridine (inm5Um), 1- thio-uracil, deoxythymidine, 5-(2-carbomethoxyvinyl)-uracil, 5-(carbamoylhydroxymethyl)-uracil, 5-carbamoylmethyl-2-thio-uracil, 5-carboxymethyl-2-thio- uracil, 5-cyanomethyl-uracil, 5-methoxy-2-thio-uracil, and 5-[3-(I-E-propenylamino)] uracil.

In some embodiments, the nucleobase is an alternative cytosine. Exemplary nucleobases and nucleosides having an alternative cytosine include 5-aza-cytosine, 6-aza-cytosine, pseudoisocytidine, 3-methyl-cytosine (m3C), N4-acetyl-cytosine (ac4C), 5-formyl-cytosine (f5C), N4-methyl-cytosine (m4C), 5-methyl-cytosine (m5C), 5-halo-cytosine (e.g., 5-iodo-cytosine), 5-hydroxymethyl-cytosine (hm5C), 1-methyl-pseudoisocytidine, pyrrolo-cytosine, pyrrolo-pseudoisocytidine, 2-thio-cytosine (s2C), 2-thio-5-methyl-cytosine, 4-thio-pseudoisocy tidine, 4-thio- 1 -methy 1-pseudoisocy tidine, 4-thio- 1 -methyl- 1 -deaza-pseudoisocytidine, 1 -methyl- 1-deaza-pseudoisocyti dine, zebularine, 5-aza-zebularine, 5 -methy 1- zebularine, 5-aza-2-thio-zebularine, 2-thio-zebularine, 2-methoxy-cytosine, 2-methoxy-5- methyl-cytosine, 4-methoxy-pseudoisocytidine, 4-methoxy- 1 -methyl-pseudoisocytidine, lysidine (k2C), 5,2'-0-dimethyl-cytidine (m5Cm), N4-acetyl-2'-0-methyl-cytidine (ac4Cm), N4,2'-0-dimethyl-cytidine (m4Cm), 5-formyl-2'-0-methyl-cytidine (f5Cm), N4,N4,2'-0- trimethyl-cytidine (m42Cm), 1 -thio-cytosine, 5-hydroxy-cytosine, 5-(3-azidopropyl)-cytosine, and 5-(2-azidoethyl)-cytosine.

In some embodiments, the nucleobase is an alternative adenine. Exemplary nucleobases and nucleosides having an alternative adenine include 2-amino-purine, 2,6-diaminopurine, 2-amino-6-halo-purine (e.g., 2-amino-6-chloro-purine), 6-halo-purine (e.g., 6-chloro-purine), 2-amino-6-methyl-purine, 8-azido-adenine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1 -methy 1-adenine (ml A), 2-methyl-adenine (m2A), N6-methyl-adenine (m6A), 2-methylthio-N6-methyl-adenine (ms2m6A), N6-isopentenyl-adenine (i6A), 2-methylthio-N6-isopentenyl-adenine (ms2i6A), N6-(cis-hydroxyisopentenyl)adenine (io6A), 2-methylthio-N6-(cis-hydroxyisopentenyl)adenine (ms2io6A), N6-glycinylcarbamoyl-adenine (g6A), N6-threonylcarbamoyl-adenine (t6A), N6-methyl-N6-threonylcarbamoyl- adenine (m6t6A), 2-methylthio-N6-threonylcarbamoyl-adenine (ms2g6A), N6,N6-dimethyl- adenine (m62A), N6-hydroxynorvalylcarbamoyl-adenine (hn6A), 2-methylthio-N6-hydroxynorvalylcarbamoyl-adenine (ms2hn6A), N6-acetyl-adenine (ac6A), 7-methyl-adenine, 2-methylthio-adenine, 2-methoxy -adenine, N6,2'-0-dimethyl-adenosine (m6Am), N6,N6,2'-0-trimethyl-adenosine (m62Am),I,2'-0-dimethyl-adenosine (ml Am), 2-amino-N6-methyl-purine, 1-thio-adenine, 8-azido-adenine, N6-(19-amino-pentaoxanonadecyl)-adenine, 2,8-dimethyl-adenine, N6-formyl-adenine, and N6-hydroxymethyl-adenine.

In some embodiments, the nucleobase is an alternative guanine. Exemplary nucleobases and nucleosides having an alternative guanine include inosine (1), 1-methyl-inosine (mil), wyosine (imG), methylwyosine (mimG), 4-demethyl-wyosine (imG-14), isowyosine (imG2), wybutosine (yVV), peroxywybutosine (o2yW), hydroxywybutosine (OHyW), undermodified hydroxywybutosine (OHyW*), 7-deaza-guanine, queuosine (Q), epoxyqueuosine (oQ), galactosyl-queuosine (galQ), mannosyl-queuosine (manQ), 7-cyano-7-deaza-guanine (preQO), 7-aminomethyl-7-deaza-guanine (preQI), archaeosine (G+), 7-deaza-8-aza-guanine, 6- thio-guanine, 6-thio-7-deaza-guanine, 6-thio-7-deaza-8-aza-guanine, 7-methyl-guanine (m7G), 6-thio-7-methyl-guanine, 7-methyl-inosine, 6-methoxy-guanine, 1 -methyl-guanine (mIG), N2-methyl-guanine (m2G), N2,N2-dimethyl-guanine (m22G), N2,7-dimethyl-guanine (m2,7G), N2, N2,7-dimethyl-guanine (m2,2,7G), 8-oxo-guanine, 7-methyl-8-oxo-guanine, 1 -methyl-6-thio-guanine, N2-methyl-6-thio-guanine, N2,N2-dimethyl-6-thio-guanine, N2-methyl-2'-0-methyl- guanosine (m2Gm), N2,N2-dimethyl-2'-0-methyl-guanosine (m22Gm), 1 -methyl-2'-0-methyl-guanosine (mlGm), N2,7-dimethyl-2'-0-methyl-guanosine (m2,7Gm), 2'-0-methyl-inosine (Im), 1,2'-0-dimethyl-inosine (mllm), 1 -thio-guanine, and O—6-methyl-guanine.

The alternative nucleobase of a nucleotide can be independently a purine, a pyrimidine, a purine or pyrimidine analog. For example, the nucleobase can be an alternative to adenine, cytosine, guanine, uracil, or hypoxanthine. In another embodiment, the nucleobase can also include, for example, naturally-occurring and synthetic derivatives of a base, including pyrazolo[3,4-d]pyrimidines, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-propynyl uracil and cytosine, 6-azo uracil, cytosine and thymine, 5-uracil (pseudouracil), 4-thiouracil, 8-halo (e.g., 8-bromo), 8-amino, 8-thiol, 8-thioalkyl, 8-hydroxy and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, deazaguanine, 7-deazaguanine, 3-deazaguanine, deazaadenine, 7-deazaadenine, 3 -deazaadenine, pyrazolo[3,4-d]pyrimidine, imidazo[I,5-a]I,3,5 triazinones, 9-deazapurines, imidazo[4,5-d]pyrazines, thiazolo[4,5-d]pyrimidines, pyrazin-2-ones, 1,2,4-triazine, pyridazine; or 1,3,5 triazine. When the nucleotides are depicted using the shorthand A, G, C, T or U, each letter refers to the representative base and/or derivatives thereof, e.g., A includes adenine or adenine analogs, e.g., 7-deaza adenine).

The mRNA may include a 5'-cap structure. The 5'-cap structure of a polynucleotide is involved in nuclear export and increasing polynucleotide stability and binds the mRNA Cap Binding Protein (CBP), which is responsible for polynucleotide stability in the cell and translation competency through the association of CBP with poly -A binding protein to form the mature cyclic mRNA species. The cap further assists the removal of 5'-proximal introns removal during mRNA splicing.

Endogenous polynucleotide molecules may be 5'-end capped generating a 5'-ppp-5' -triphosphate linkage between a terminal guanosine cap residue and the 5'-terminal transcribed sense nucleotide of the polynucleotide. This 5'-guanylate cap may then be methylated to generate an N7-methyl-guanylate residue. The ribose sugars of the terminal and/or anteterminal transcribed nucleotides of the 5' end of the polynucleotide may optionally also be 2'-0-methylated. 5'-decapping through hydrolysis and cleavage of the guanylate cap structure may target a polynucleotide molecule, such as an mRNA molecule, for degradation.

Alterations to polynucleotides may generate a non-hydrolyzable cap structure preventing decapping and thus increasing polynucleotide half-life. Because cap structure hydrolysis requires cleavage of 5'-ppp-5' phosphorodiester linkages, alternative nucleotides may be used during the capping reaction. For example, a Vaccinia Capping Enzyme from New England Biolabs (Ipswich, MA) may be used with a-thio-guanosine nucleotides according to the manufacturers instructions to create a phosphorothioate linkage in the 5'-ppp-5' cap.

Additional alternative guanosine nucleotides may be used such as a-methyl-phosphonate and seleno-phosphate nucleotides. Additional alterations include, but are not limited to, 2'-0-methylation of the ribose sugars of 5'-terminal and/or 5 '-anteterminal nucleotides of the polynucleotide (as mentioned above) on the 2'-hydroxy group of the sugar. Multiple distinct 5'-cap structures can be used to generate the 5'-cap of an mRNA molecule.

Cap analogs, which herein are also referred to as synthetic cap analogs, chemical caps, chemical cap analogs, or structural or functional cap analogs, differ from natural (i.e., endogenous, wild-type, or physiological) 5'-caps in their chemical structure, while retaining cap function. Cap analogs may be chemically (i.e., non-enzymatically) or enzymatically synthesized and/linked to a polynucleotide. For example, the Anti-Reverse Cap Analog (ARCA) cap contains two guanosines linked by a 5'-5'-triphosphate group, wherein one guanosine contains an N7-methyl group as well as a 3'-0-methyl group (i.e., N7, '-0-dimethyl-guanosine-5'-triphosphate-5 '-guanosine, m7G-3'mppp-G, which may equivalently be designated 3' 0-Me-m7G(5')ppp(5')G). The 3'-0 atom of the other, unaltered, guanosine becomes linked to the 5 '-terminal nucleotide of the capped polynucleotide (e.g., an mRNA). The N7- and 3'-0-methylated guanosine provides the terminal moiety of the capped polynucleotide (e.g., mRNA). Another exemplary cap is mCAP, which is similar to ARCA but has a 2'-0-methyl group on guanosine (i.e., N7,2'-0-dimethyl-guanosine-5 '-triphosphate-5'-guanosine, m7Gm- ppp-G).

A cap may be a dinucleotide cap analog. As a non-limiting example, the dinucleotide cap analog may be modified at different phosphate positions with a boranophosphate group or a phophoroselenoate group such as the dinucleotide cap analogs described in US Patent No. 8,519,110, the cap structures of which are herein incorporated by reference.

Alternatively, a cap analog may be a N7-(4-chlorophenoxy ethyl) substituted dinucleotide cap analog known in the art and/or described herein. Non-limiting examples of N7-(4-chlorophenoxy ethyl) substituted dinucleotide cap analogs include a N7-(4-chlorophenoxyethyl)-G(5)ppp(5')G and a N7-(4-chlorophenoxyethyl)-m3 '—OG(5)ppp(5')G cap analog (see, e.g., the various cap analogs and the methods of synthesizing cap analogs described in Kore et al. Bioorganic & Medicinal Chemistry 2013 21 :4570-4574; the cap structures of which are herein incorporated by reference). In other instances, a cap analog useful in the polynucleotides of the present disclosure is a 4-chloro/bromophenoxy ethyl analog.

While cap analogs allow for the concomitant capping of a polynucleotide in an in vitro transcription reaction, up to 20% of transcripts remain uncapped. This, as well as the structural differences of a cap analog from endogenous 5'-cap structures of polynucleotides produced by the endogenous, cellular transcription machinery, may lead to reduced translational competency and reduced cellular stability.

Alternative polynucleotides may also be capped post-transcriptionally, using enzymes, in order to generate more authentic 5'-cap structures. As used herein, the phrase "more authentic" refers to a feature that closely mirrors or mimics, either structurally or functionally, an endogenous or wild type feature. That is, a "more authentic" feature is better representative of an endogenous, wild-type, natural or physiological cellular function, and/or structure as compared to synthetic features or analogs of the prior art, or which outperforms the corresponding endogenous, wild-type, natural, or physiological feature in one or more respects.

Non-limiting examples of more authentic 5'-cap structures useful in the polynucleotides of the present disclosure are those which, among other things, have enhanced binding of cap binding proteins, increased half-life, reduced susceptibility to 5'-endonucleases, and/or reduced 5'-decapping, as compared to synthetic 5'-cap structures known in the art (or to a wild-type, natural or physiological 5'-cap structure). For example, recombinant Vaccinia Virus Capping Enzyme and recombinant 2'-0-methyltransferase enzyme can create a canonical 5'-5'-triphosphate linkage between the 5'-terminal nucleotide of a polynucleotide and a guanosine cap nucleotide wherein the cap guanosine contains an N7-methylation and the 5'-terminal nucleotide of the polynucleotide contains a 2'-0-methyl. Such a structure is termed the Capl structure. This cap results in a higher translational-competency, cellular stability, and a reduced activation of cellular pro-inflammatory cytokines, as compared, e.g., to other 5' cap analog structures known in the art. Other exemplary cap structures include 7mG(5')ppp(5')N,pN2p (Cap 0), 7mG(5')ppp(5')NImpNp (Cap 1), 7mG(5 ')-ppp(5') NImpN2mp (Cap 2), and m(7)Gpppm(3)(6,6,2')Apm(2') Apm(2')Cpm(2)(3,2')Up (Cap 4).

Because the alternative polynucleotides may be capped post-transcriptionally, and because this process is more efficient, nearly 100% of the mRNA may be capped. This is in contrast to -80% when a cap analog is linked to a polynucleotide in the course of an in vitro transcription reaction. 5'-terminal caps may include endogenous caps or cap analogs. A 5'-terminal cap may include a guanosine analog. Useful guanosine analogs include inosine, N1-methyl-guanosine, 2'-fluoro-guanosine, 7-deaza-guanosine, 8-oxo-guanosine, 2-amino-guanosine, LNA-guanosine, and 2-azido-guanosine. In some cases, a polynucleotide contains a modified 5'-cap. A modification on the 5'-cap may increase the stability of polynucleotide, increase the half-life of the polynucleotide, and could increase the polynucleotide translational efficiency. The modified 5 '-cap may include, but is not limited to, one or more of the following modifications: modification at the 2'- and/or 3'-position of a capped guanosine triphosphate (GTP), a replacement of the sugar ring oxygen (that produced the carbocyclic ring) with a methylene moiety (CH2), a modification at the triphosphate bridge moiety of the cap structure, or a modification at the nucleobase (G) moiety.

A 5'-UTR may be provided as a flanking region to the mRNA. A 5'-UTR may be homologous or heterologous to the coding region found in a polynucleotide. Multiple 5'-UTRs may be included in the flanking region and may be the same or of different sequences. Any portion of the flanking regions, including none, may be codon optimized and any may independently contain one or more different structural or chemical alterations, before and/or after codon optimization.

In one embodiment, an ORF encoding an antigen of the disclosure is codon optimized. Codon optimization methods are known in the art. For example, an ORF of any one or more of the sequences provided herein may be codon optimized. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g., glycosylation sites); add, remove or shuffle protein domains; insert or delete restriction sites; modify ribosome binding sites and mRNA degradation sites; adjust translational rates to allow the various domains of the protein to fold properly; or reduce or eliminate problem secondary structures within the polynucleotide. Codon optimization tools, algorithms and services are known in the art—non-limiting examples include services from GeneArt (Life Technologies), DNA2.0 (Menlo Park Calif.) and/or proprietary methods. In some embodiments, the open reading frame (ORF) sequence is optimized using optimization algorithms.To alter one or more properties of an mRNA, 5'-UTRs which are heterologous to the coding region of an mRNA may be engineered. The mRNA may then be administered to cells, tissue or organisms and outcomes such as protein level, localization, and/or half-life may be measured to evaluate the beneficial effects the heterologous 5'-UTR may have on the mRNA. Variants of the 5'-UTRs may be utilized wherein one or more nucleotides are added or removed to the termini, including A, T, C or G. 5'-UTRs may also be codon-optimized, or altered in any manner described herein.

mRNAs may include a stem loop such as, but not limited to, a histone stem loop. The stem loop may be a nucleotide sequence that is about 25 or about 26 nucleotides in length. The histone stem loop may be located 3'-relative to the coding region (e.g., at the 3'-terminus of the coding region). As a non-limiting example, the stem loop may be located at the 3'-end of a polynucleotide described herein. In some cases, an mRNA includes more than one stem loop (e.g., two stem loops). A stem loop may be located in a second terminal region of a polynucleotide. As a non-limiting example, the stem loop may be located within an untranslated region (e.g., 3'-UTR) in a second terminal region. In some cases, a mRNA which includes the histone stem loop may be stabilized by the addition of a 3'-stabilizing region (e.g., a 3'-stabilizing region including at least one chain terminating nucleoside). Not wishing to be bound by theory, the addition of at least one chain terminating nucleoside may slow the degradation of a polynucleotide and thus can increase the half-life of the polynucleotide. In other cases, a mRNA, which includes the histone stem loop may be stabilized by an alteration to the 3'-region of the polynucleotide that can prevent and/or inhibit the addition of oligio(U). In yet other cases, a mRNA, which includes the histone stem loop may be stabilized by the addition of an oligonucleotide that terminates in a 3'-deoxynucleoside, 2',3'-dideoxpucleoside 3'-0-methylnucleosides, 3-0- ethylnucleosides, 3'-arabinosides, and other alternative nucleosides known in the art and/or described herein. In some instances, the mRNA of the present disclosure may include a histone stem loop, a poly-A region, and/or a 5'-cap structure. The histone stem loop may be before and/or after the poly-A region. The polynucleotides including the histone stem loop and a poly-A region sequence may include a chain terminating nucleoside described herein. In other instances, the polynucleotides of the present disclosure may include a histone stem loop and a 5'-cap structure. The 5'-cap structure may include, but is not limited to, those described herein and/or known in the art. In some cases, the conserved stem loop region may include a miR sequence described herein. As a non-limiting example, the stem loop region may include the seed sequence of a miR sequence described herein. In another non-limiting example, the stem loop region may include a miR- 122 seed sequence.

mRNA may include at least one histone stem-loop and a poly-A region or polyadenylation signal. In certain cases, the polynucleotide encoding for a histone stem loop and a poly-A region or a polyadenylation signal may code for a pathogen antigen or fragment thereof. In other cases, the polynucleotide encoding for a histone stem loop and a poly-A region or a polyadenylation signal may code for a therapeutic protein. In some cases, the polynucleotide encoding for a histone stem loop and a poly-A region or a polyadenylation signal may code for a tumor antigen or fragment thereof. In other cases, the polynucleotide encoding for a histone stem loop and a poly-A region or a polyadenylation signal may code for an allergenic antigen or an autoimmune self-antigen.

An mRNA may include a polyA sequence and/or polyadenylation signal. A polyA sequence may be comprised entirely or mostly of adenine nucleotides or analogs or derivatives thereof. A polyA sequence may be a tail located adjacent to a 3' untranslated region of a nucleic acid. During RNA processing, a long chain of adenosine nucleotides (poly-A region) is normally added to messenger RNA (mRNA) molecules to increase the stability of the molecule. Immediately after transcription, the 3'-end of the transcript is cleaved to free a 3'-hydroxy. Then poly-A polymerase adds a chain of adenosine nucleotides to the RNA. The process, called polyadenylation, adds a poly-A region that is between 100 and 250 residues long. Unique poly-A region lengths may provide certain advantages to the alternative polynucleotides of the present disclosure. Generally, the length of a poly-A region of the present disclosure is at least 30 nucleotides in length. In another embodiment, the poly-A region is at least 35 nucleotides in length. In another embodiment, the length is at least 40 nucleotides. In another embodiment, the length is at least 45 nucleotides. In another embodiment, the length is at least 55 nucleotides. In another embodiment, the length is at least 60 nucleotides. In another embodiment, the length is at least 70 nucleotides. In another embodiment, the length is at least 80 nucleotides. In another embodiment, the length is at least 90 nucleotides. In another embodiment, the length is at least 100 nucleotides. In another embodiment, the length is at least 120 nucleotides. In another embodiment, the length is at least 140 nucleotides. In another embodiment, the length is at least 160 nucleotides. In another embodiment, the length is at least 180 nucleotides. In another embodiment, the length is at least 200 nucleotides. In another embodiment, the length is at least 250 nucleotides. In another embodiment, the length is at least 300 nucleotides. In another embodiment, the length is at least 350 nucleotides. In another embodiment, the length is at least 400 nucleotides. In another embodiment, the length is at least 450 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 900 nucleotides. In another embodiment, the length is at least 1000 nucleotides. In another embodiment, the length is at least 1100 nucleotides. In another embodiment, the length is at least 1200 nucleotides. In another embodiment, the length is at least 1300 nucleotides. In another embodiment, the length is at least 1400 nucleotides. In another embodiment, the length is at least 1500 nucleotides. In another embodiment, the length is at least 1600 nucleotides. In another embodiment, the length is at least 1700 nucleotides. In another embodiment, the length is at least 1800 nucleotides. In another embodiment, the length is at least 1900 nucleotides. In another embodiment, the length is at least 2000 nucleotides. In another embodiment, the length is at least 2500 nucleotides. In another embodiment, the length is at least 3000 nucleotides. In some instances, the poly-A region may be 80 nucleotides, 120 nucleotides, 160 nucleotides in length on an alternative polynucleotide molecule described herein. In other instances, the poly-A region may be 20, 40, 80, 100, 120, 140 or 160 nucleotides in length on an alternative polynucleotide molecule described herein. In some cases, the poly-A region is designed relative to the length of the overall alternative polynucleotide. This design may be based on the length of the coding region of the alternative polynucleotide, the length of a particular feature or region of the alternative polynucleotide (such as mRNA) or based on the length of the ultimate product expressed from the alternative polynucleotide. When relative to any feature of the alternative polynucleotide (e.g., other than the mRNA portion which includes the poly-A region) the poly-A region may be 10, 20, 30, 40, 50, 60, 70, 80, 90 or 100% greater in length than the additional feature. The poly-A region may also be designed as a fraction of the alternative polynucleotide to which it belongs. In this context, the poly-A region may be 10, 20, 30, 40, 50, 60, 70, 80, or 90% or more of the total length of the construct or the total length of the construct minus the poly-A region.

In certain cases, engineered binding sites and/or the conjugation of mRNA for poly-A binding protein may be used to enhance expression. The engineered binding sites may be sensor sequences which can operate as binding sites for ligands of the local microenvironment of the mRNA. As a non-limiting example, the mRNA may include at least one engineered binding site to alter the binding affinity of poly-A binding protein (PABP) and analogs thereof. The incorporation of at least one engineered binding site may increase the binding affinity of the PABP and analogs thereof.

Additionally, multiple distinct mRNA may be linked together to the PABP (poly-A binding protein) through the 3'-end using alternative nucleotides at the 3'- terminus of the poly-A region. Transfection experiments can be conducted in relevant cell lines at and protein production can be assayed by ELISA at 12 hours, 24 hours, 48 hours, 72 hours, and day 7 post-transfection. As a non-limiting example, the transfection experiments may be used to evaluate the effect on PABP or analogs thereof binding affinity as a result of the addition of at least one engineered binding site. In certain cases, a poly-A region may be used to modulate translation initiation. While not wishing to be bound by theory, the poly-A region recruits PABP which in turn can interact with translation initiation complex and thus may be essential for protein synthesis. In some cases, a poly-A region may also be used in the present disclosure to protect against 3'-5'-exonuclease digestion. In some instances, an mRNA may include a polyA-G Quartet. The G-quartet is a cyclic hydrogen bonded array of four guanosine nucleotides that can be formed by G-rich sequences in both DNA and RNA. In this embodiment, the G-quartet is incorporated at the end of the poly-A region. The resultant mRNA may be assayed for stability, protein production and other parameters including half-life at various time points. It has been discovered that the polyA-G quartet results in protein production equivalent to at least 75% of that seen using a poly-A region of 120 nucleotides alone. In some cases, mRNA may include a poly-A region and may be stabilized by the addition of a 3'-stabilizing region. The mRNA with a poly-A region may further include a 5'-cap structure. In other cases, mRNA may include a poly-A-G Quartet. The mRNA with a poly-A-G Quartet may further include a 5'-cap structure. In some cases, the 3'-stabilizing region which may be used to stabilize mRNA includes a poly-A region or poly-A-G Quartet. In other cases, the 3'-stabilizing region which may be used with the present disclosure include a chain termination nucleoside such as 3'-deoxyadenosine (cordycepin), 3'-deoxyuridine, 3'- deoxycytosine, 3'-deoxyguanosine, 3'-deoxy thymine, 2',3'-dideoxpucleosides, such as 2',3 dideoxyadenosine, 2',3 '-dideoxpridine, 2',3'-dideoxycytosine, 2', 3 '-dideoxyguanosine, 2',3'-dideoxythymine, a 2'-deoxynucleoside, or an O—methylnucleoside. In other cases, mRNA which includes a polyA region or a poly-A-G Quartet may be stabilized by an alteration to the 3'-region of the polynucleotide that can prevent and/or inhibit the addition of oligio(U). In yet other instances, mRNA which includes a poly-A region or a poly-A-G Quartet may be stabilized by the addition of an oligonucleotide that terminates in a 3'-deoxynucleoside, 2',3'-dideoxynucleoside 3—O—methylnucleosides, 3'—O—ethylnucleosides, 3'-arabinosides, and other alternative nucleosides known in the art and/or described herein.

In an embodiment, the mRNA vaccines of the disclosure comprise lipids. The lipids and modRNA can together form nanoparticles. The lipids can encapsulate the mRNA in the form of a lipid nanoparticle (LNP) to aid cell entry and stability of the RNA/lipid nanoparticles.

Lipid nanoparticles may include a lipid component and one or more additional components, such as a therapeutic and/or prophylactic. A LNP may be designed for one or more specific applications or targets. The elements of a LNP may be selected based on a particular application or target, and/or based on the efficacy, toxicity, expense, ease of use, availability, or other feature of one or more elements. Similarly, the particular formulation of a LNP may be selected for a particular application or target according to, for example, the efficacy and toxicity of particular combinations of elements. The efficacy and tolerability of a LNP formulation may be affected by the stability of the formulation.

Lipid nanoparticles may be designed for one or more specific applications or targets. For example, a LNP may be designed to deliver a therapeutic and/or prophylactic such as an RNA to a particular cell, tissue, organ, or system or group thereof in a mammal's body.

Physiochemical properties of lipid nanoparticles may be altered to increase selectivity for particular bodily targets. For instance, particle sizes may be adjusted based on the fenestration sizes of different organs. The therapeutic and/or prophylactic included in a LNP may also be selected based on the desired delivery target or targets. For example, a therapeutic and/or prophylactic may be selected for a particular indication, condition, disease, or disorder and/or for delivery to a particular cell, tissue, organ, or system or group thereof (e.g., localized or specific delivery). In certain embodiments, a LNP may include an mRNA encoding a polypeptide of interest capable of being translated within a cell to produce the polypeptide of interest. Such a composition may be designed to be specifically delivered to a particular organ. In some embodiments, a composition may be designed to be specifically delivered to a mammalian liver. In some embodiments, a composition may be designed to be specifically delivered to a lymph node. In some embodiments, a composition may be designed to be specifically delivered to a mammalian spleen.

A LNP may include one or more components described herein. In some embodiments, the LNP formulation of the disclosure includes at least one lipid nanoparticle component. Lipid nanoparticles may include a lipid component and one or more additional components, such as a therapeutic and/or prophylactic, such as a nucleic acid. A LNP may be designed for one or more specific applications or targets. The elements of a LNP may be selected based on a particular application or target, and/or based on the efficacy, toxicity, expense, ease of use, availability, or other feature of one or more elements. Similarly, the particular formulation of a LNP may be selected for a particular application or target according to, for example, the efficacy and toxicity of particular combination of elements. The efficacy and tolerability of a LNP formulation may be affected by the stability of the formulation.

In some embodiments, for example, a polymer may be included in and/or used to encapsulate or partially encapsulate a LNP. A polymer may be biodegradable and/or biocompatible. A polymer may be selected from, but is not limited to, polyamines, polyethers, polyamides, polyesters, poly carbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, and polyarylates. For example, a polymer may include poly(caprolactone) (PCL), ethylene vinyl acetate polymer (EVA), poly (lactic acid) (PLA), poly(L-lactic acid) (PLLA), poly(gly colic acid) (PGA), poly(lactic acid-co-gly colic acid) (PLGA), poly(L-lactic acid-co-gly colic acid) (PLLGA), poly(D,L-lactide) (PDLA), poly(L- lactide) (PLLA), poly (D,L-lactide-co-caprolactone), poly(D,L-lactide-co- caprolactone-co- glycolide), poly(D,L-lactide-co-PEO-co-D,L-lactide), poly(D,L-lactide-co-PPO-co-D,L-lactide), polyalkyl cyanoacrylate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly (vinyl chloride) (PVC), polyvinylpyrrolidone (PVP), polysiloxanes, polystyrene, polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl (meth)acrylate), poly(butyl(meth)acrylate), poly(isobutyl (meth)acrylate), poly(hexyl(meth)acrylate), poly(isodecyl (meth)acrylate), poly(lauryl(meth)acrylate), poly(phenyl (meth)acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, poloxamines, poly(ortho)esters, poly(butyric acid), poly(valeric acid), poly(lactide-co-caprolactone), trimethylene carbonate, poly (N-acryloylmorpholine) (PAcM), poly(2-methyl-2-oxazoline) (PMOX), poly(2-ethyl-2-oxazoline) (PEOZ), and polyglycerol.

Surface altering agents may include, but are not limited to, anionic proteins (e.g., bovine serum albumin), surfactants (e.g., cationic surfactants such as dimethyldioctadecylammonium bromide), sugars or sugar derivatives (e.g., cyclodextrin), nucleic acids, polymers (e.g., heparin, polyethylene glycol, and poloxamer), mucolytic agents (e.g., acetylcysteine, mugwort, bromelain, papain, clerodendrum, bromhexine, carbocisteine, eprazinone, mesna, ambroxol, sobrerol, domiodol, letosteine, stepronin, tiopronin, gelsolin, thymosin β4, dornase alfa, neltenexine, and erdosteine), and DNases (e.g., rhDNase). A surface altering agent may be disposed within a nanoparticle and/or on the surface of a LNP (e.g., by coating, adsorption, covalent linkage, or other process).

A LNP may also comprise one or more functionalized lipids. For example, a lipid may be functionalized with an alkyne group that, when exposed to an azide under appropriate reaction conditions, may undergo a cycloaddition reaction. In particular, a lipid bilayer may be functionalized in this fashion with one or more groups useful in facilitating membrane permeation, cellular recognition, or imaging. The surface of a LNP may also be conjugated with one or more useful antibodies. Functional groups and conjugates useful in targeted cell delivery, imaging, and membrane permeation are well known in the art.

In addition to these components, lipid nanoparticles may include any substance useful in pharmaceutical compositions. For example, the lipid nanoparticle may include one or more pharmaceutically acceptable excipients or accessory ingredients such as, but not limited to, one or more solvents, dispersion media, diluents, dispersion aids, suspension aids, surface active agents, buffering agents, preservatives, and other species.

Surface active agents and/or emulsifiers may include, but are not limited to, natural emulsifiers (e.g., acacia, alginic acid, sodium alginate, cholesterol, and lecithin), sorbitan fatty acid esters (e.g., polyoxy ethylene sorbitan monolaurate [TWEEN®20], polyoxy ethylene sorbitan [TWEEN® 60], polyoxy ethylene sorbitan monooleate [TWEEN®80], sorbitan monopalmitate [SPAN®40], sorbitan monostearate [SPAN®60], sorbitan tristearate [SPAN®65], glyceryl monooleate, sorbitan monooleate [SPAN®80]), polyoxyethylene esters (e.g., polyoxyethylene monostearate [MYRJ® 45], polyoxyethylene hydrogenated castor oil, polyethoxylated castor oil, polyoxymethylene stearate, and SOLUTOL®), sucrose fatty acid esters, polyethylene glycol fatty acid esters (e.g., CREMOPHOR®), polyoxyethylene ethers, (e.g., polyoxyethylene lauryl ether [BRIJ® 30]), poly(vinylpyrrolidone), diethylene glycol monolaurate, triethanolamine oleate, sodium oleate, potassium oleate, ethyl oleate, oleic acid, ethyl laurate, sodium lauryl sulfate, PLURONIC®F 68, POLOXAMER® 188, cetrimonium bromide, cetylpyridinium chloride, benzalkonium chloride, docusate sodium, and/or combinations thereof.

Examples of preservatives may include, but are not limited to, antioxidants, chelating agents, free radical scavengers, antimicrobial preservatives, antifungal preservatives, alcohol preservatives, acidic preservatives, and/or other preservatives. Examples of antioxidants include, but are not limited to, alpha tocopherol, ascorbic acid, ascorbyl palmitate, butylated hydroxyanisole, butylated hydroxy toluene, monothioglycerol, potassium metabisulfite, propionic acid, propyl gallate, sodium ascorbate, sodium bisulfite, sodium metabisulfite, and/or sodium sulfite. Examples of chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Examples of antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Examples of antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Examples of alcohol preservatives include, but are not limited to, ethanol, polyethylene glycol, benzyl alcohol, phenol, phenolic compounds, bisphenol, chlorobutanol, hydroxybenzoate, and/or phenylethyl alcohol. Examples of acidic preservatives include, but are not limited to, vitamin A, vitamin C, vitamin E, beta-carotene, citric acid, acetic acid, dehydroascorbic acid, ascorbic acid, sorbic acid, and/or phytic acid. Other preservatives include, but are not limited to, tocopherol, tocopherol acetate, deteroxime mesylate, cetrimide, butylated hydroxyanisole (BHA), butylated hydroxy toluene (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL® 115, GERMABEN®II, NEOLONETM, KATHON™, and/or EUXYL®. An exemplary free radical scavenger includes butylated hydroxytoluene (BHT or butylhydroxytoluene) or deferoxamine.

Examples of buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, d-gluconic acid, calcium glycerophosphate, calcium lactate, calcium lactobionate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, amino-sulfonate buffers (e.g., HEPES), magnesium hydroxide, aluminum hydroxide, alginic acid, pyrogen-free water, isotonic saline, Ringer's solution, ethyl alcohol, and/or combinations thereof.

In some embodiments, the formulation including a LNP may further include a salt, such as a chloride salt. In some embodiments, the formulation including a LNP may further includes a sugar such as a disaccharide. In some embodiments, the formulation further includes a sugar but not a salt, such as a chloride salt.In some embodiments, a LNP may further include one or more small hydrophobic molecules such as a vitamin (e.g., vitamin A or vitamin E) or a sterol. Carbohydrates may include simple sugars (e.g., glucose) and polysaccharides (e.g., glycogen and derivatives and analogs thereof).

The characteristics of a LNP may depend on the components thereof. For example, a LNP including cholesterol as a structural lipid may have different characteristics than a LNP that includes a different structural lipid. As used herein, the term "structural lipid" refers to sterols and also to lipids containing sterol moieties. As defined herein, "sterols" are a subgroup of steroids consisting of steroid alcohols. In some embodiments, the structural lipid is a steroid. In some embodiments, the structural lipid is cholesterol. In some embodiments, the structural lipid is an analog of cholesterol. In some embodiments, the structural lipid is alpha-tocopherol.

In some embodiments, the characteristics of a LNP may depend on the absolute or relative amounts of its components. For instance, a LNP including a higher molar fraction of a phospholipid may have different characteristics than a LNP including a lower molar fraction of a phospholipid. Characteristics may also vary depending on the method and conditions of preparation of the lipid nanoparticle. In general, phospholipids comprise a phospholipid moiety and one or more fatty acid moieties.

A phospholipid moiety can be selected, for example, from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin. A fatty acid moiety can be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid. Particular phospholipids can facilitate fusion to a membrane. In some embodiments, a cationic phospholipid can interact with one or more negatively charged phospholipids of a membrane (e.g., a cellular or intracellular membrane). Fusion of a phospholipid to a membrane can allow one or more elements (e.g., a therapeutic agent) of a lipid-containing composition (e.g., LNPs) to pass through the membrane permitting, e.g., delivery of the one or more elements to a target tissue. Non-natural phospholipid species including natural species with modifications and substitutions including branching, oxidation, cyclization, and alkynes are also contemplated. In some embodiments, a phospholipid can be functionalized with or cross-linked to one or more alkynes (e.g., an alkenyl group in which one or more double bonds is replaced with a triple bond). Under appropriate reaction conditions, an alkyne group can undergo a copper-catalyzed cycloaddition upon exposure to an azide. Such reactions can be useful in functionalizing a lipid bilayer of a nanoparticle composition to facilitate membrane permeation or cellular recognition or in conjugating a nanoparticle composition to a useful component such as a targeting or imaging moiety (e.g., a dye). Phospholipids include, but are not limited to, glycerophospholipids such as phosphatidylcholines, phosphatidyl-ethanolamines, phosphatidylserines, phosphatidylinositols, phosphatidy glycerols, and phosphatidic acids. Phospholipids also include phosphosphingolipid, such as sphingomyelin. In some embodiments, a phospholipid useful or potentially useful in the present invention is an analog or variant of DSPC.

Lipid nanoparticles may be characterized by a variety of methods. For example, microscopy (e.g., transmission electron microscopy or scanning electron microscopy) may be used to examine the morphology and size distribution of a LNP. Dynamic light scattering or potentiometry (e.g., potentiometric titrations) may be used to measure zeta potentials. Dynamic light scattering may also be utilized to determine particle sizes. Instruments such as the Zetasizer Nano ZS (Malvern Instruments Ltd, Malvern, Worcestershire, UK) may also be used to measure multiple characteristics of a LNP, such as particle size, polydispersity index, and zeta potential.

The mean size of a LNP may be between 10s of nm and 100s of nm, e.g., measured by dynamic light scattering (DLS). For example, the mean size may be from about 40 nm to about 150 nm, such as about 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm. In some embodiments, the mean size of a LNP may be from about 50 nm to about 100 nm, from about 50 nm to about 90 nm, from about 50 nm to about 80 nm, from about 50 nm to about 70 nm, from about 50 nm to about 60 nm, from about 60 nm to about 100 nm, from about 60 nm to about 90 nm, from about 60 nm to about 80 nm, from about 60 nm to about 70 nm, from about 70 nm to about 100 nm, from about 70 nm to about 90 nm, from about 70 nm to about 80 nm, from about 80 nm to about 100 nm, from about 80 nm to about 90 nm, or from about 90 nm to about 100 nm. In certain embodiments, the mean size of a LNP may be from about 70 nm to about 100 nm. In a particular embodiment, the mean size may be about 80 nm. In other embodiments, the mean size may be about 100 nm.

A LNP may be relatively homogenous. A polydispersity index may be used to indicate the homogeneity of a LNP, e.g., the particle size distribution of the lipid nanoparticles. A small (e.g., less than 0.3) polydispersity index generally indicates a narrow particle size distribution. A LNP may have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a LNP may be from about 0.10 to about 0.20.

The zeta potential of a LNP may be used to indicate the electrokinetic potential of the composition. For example, the zeta potential may describe the surface charge of a LNP. Lipid nanoparticles with relatively low charges, positive or negative, are generally desirable, as more highly charged species may interact undesirably with cells, tissues, and other elements in the body. In some embodiments, the zeta potential of a LNP may be from about −10 mV to about +20 mV, from about −10 mV to about +15 mV, from about −10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

The efficiency of encapsulation of a therapeutic and/or prophylactic describes the amount of therapeutic and/or prophylactic that is encapsulated or otherwise associated with a LNP after preparation, relative to the initial amount provided. The encapsulation efficiency is desirably high (e.g., close to 100%). The encapsulation efficiency may be measured, for example, by comparing the amount of therapeutic and/or prophylactic in a solution containing the lipid nanoparticle before and after breaking up the lipid nanoparticle with one or more organic solvents or detergents. Fluorescence may be used to measure the amount of free therapeutic and/or prophylactic (e.g., RNA) in a solution. For the lipid nanoparticles described herein, the encapsulation efficiency of a therapeutic and/or prophylactic may be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency may be at least 80%. In certain embodiments, the encapsulation efficiency may be at least 90%.

A LNP may optionally comprise one or more coatings. For example, a LNP may be formulated in a capsule, film, or tablet having a coating. A capsule, film, or tablet including a composition described herein may have any useful size, tensile strength, hardness, or density.

Formulations comprising amphiphilic polymers and lipid nanoparticles may be formulated in whole or in part as pharmaceutical compositions. Pharmaceutical compositions may include one or more amphiphilic polymers and one or more lipid nanoparticles. For example, a pharmaceutical composition may include one or more amphiphilic polymers and one or more lipid nanoparticles including one or more different therapeutics and/or prophylactics. Pharmaceutical compositions may further include one or more pharmaceutically acceptable excipients or accessory ingredients such as those described herein. General guidelines for the formulation and manufacture of pharmaceutical compositions and agents are available, for example, in Remington's The Science and Practice of Pharmacy, 21st Edition, A. R. Gennaro; Lippincott, Williams & Wilkins, Baltimore, Md., 2006. Conventional excipients and accessory ingredients may be used in any pharmaceutical composition, except insofar as any conventional excipient or accessory ingredient may be incompatible with one or more components of a LNP or the one or more amphiphilic polymers in the formulation of the disclosure. An excipient or accessory ingredient may be incompatible with a component of a LNP or the amphiphilic polymer of the formulation if its combination with the component or amphiphilic polymer may result in any undesirable biological effect or otherwise deleterious effect.

In some embodiments, one or more excipients or accessory ingredients may make up greater than 50% of the total mass or volume of a pharmaceutical composition including a LNP. For example, the one or more excipients or accessory ingredients may make up 50%, 60%, 70%, 80%, 90%, or more of a pharmaceutical convention. In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia. Relative amounts of the one or more amphiphilic polymers, the one or more lipid nanoparticles, the one or more pharmaceutically acceptable excipients, and/or any additional ingredients in a pharmaceutical composition in accordance with the present disclosure will vary, depending upon the identity, size, and/or condition of the subject treated and further depending upon the route by which the composition is to be administered. By way of example, a pharmaceutical composition may comprise between 0.1% and 100% (wt/wt) of one or more lipid nanoparticles. As another example, a pharmaceutical composition may comprise between 0.1% and 15% (wt/vol) of one or more amphiphilic polymers (e.g., 0.5%, 1%, 2.5%, 5%, 10%, or 12.5% w/v).

In certain embodiments, the lipid nanoparticles and/or pharmaceutical compositions of the disclosure are refrigerated or frozen for storage and/or shipment (e.g., being stored at a temperature of 4° C. or lower, such as a temperature between about −150° C. and about 0° C. or between about −80° C. and about −20° C. (e.g., about −5° C., −10° C., −15° C., −20° C., −25° C., −30° C., −40° C., −50° C., −60° C., −70° C., −80° C., −90° C., −130° C. or −150° C.). For example, the pharmaceutical composition comprising one or more amphiphilic polymers and one or more lipid nanoparticles is a solution or solid (e.g., via lyophilization) that is refrigerated for storage and/or shipment at, for example, about −20° C., −30° C., −40° C., −50° C., −60° C., −70° C., or −80° C. In certain embodiments, the disclosure also relates to a method of increasing stability of the lipid nanoparticles by adding an effective amount of an amphiphilic polymer and by storing the lipid nanoparticles and/or pharmaceutical compositions thereof at a temperature of 4° C. or lower, such as a temperature between about −150° C. and about 0° C. or between about −80° C. and about −20° C., e.g., about −5° C., −10° C., −15° C., −20° C., −25° C., −30° C., −40° C., −50° C., −60° C., −70° C., −80° C., −90° C., −130° C. or −150° C.).

The chemical properties of the LNP, LNP suspension, lyophilized LNP composition, or LNP formulation of the present disclosure may be characterized by a variety of methods. In some embodiments, electrophoresis (e.g., capillary electrophoresis) or chromatography (e.g., reverse phase liquid chromatography) may be used to examine the mRNA integrity.

The efficacy of the product is dependent on expression of the delivered RNA, which requires a sufficiently intact RNA molecule. RNA integrity is a measure of RNA quality that quantitates intact RNA. The method is also capable of detecting potential degradation products. RNA integrity is preferably determined by capillary gel electrophoresis. The initial specification is set to ensure sufficient RNA integrity in drug product preparations. In some embodiments, the RNA polynucleotide has an integrity of at least about 80%,85%, 90%, 92%, 94%, 95%, 96%, 97%, 98%, or 99%. In some embodiments, the RNA polynucleotide has an integrity of or greater than about 95%. In some embodiments, the RNA polynucleotide has an integrity of or greater than about 98%. In some embodiments, the RNA polynucleotide has an integrity of or greater than about 99%.

In preferred embodiments, the RNA polynucleotide has a clinical grade purity. In some embodiments, the purity of the RNA polynucleotide is between about 60% and about 100%. In some embodiments, the purity of the RNA polynucleotide is between about 80% and 99%. In some embodiments, the purity of the RNA polynucleotide is between about 90% and about 99%. In some embodiments, wherein the purified mRNA has a clinical grade purity without further purification. In some embodiments, the clinical grade purity is achieved through a method including tangential flow filtration (TFF) purification. In some embodiments, the clinical grade purity is achieved without the further purification selected from high performance liquid chromatography (HPLC) purification, ligand or binding based purification, and/or ion exchange chromatography. In some embodiments, the method of producing the RNA polynucleotides removes long abortive RNA species, double-stranded RNA (dsRNA), residual plasmid DNA residual solvent and/or residual salt. In some embodiments, the short abortive transcript contaminants comprise less than 15 bases. In some embodiments, the short abortive transcript contaminants comprise about 8-12 bases. In some embodiments, the method of the invention also removes RNAse inhibitor.

In some embodiments, the purified RNA polynucleotide comprises 5% or less, 4% or less, 3% or less, 2% or less, 1% or less or is substantially free of protein contaminants as determined by capillary electrophoresis. In some embodiments, the purified RNA polynucleotide comprises less than 5%, less than 4%, less than 3%, less than 2%, less than 1%, or is substantially free of salt contaminants determined by high performance liquid chromatography (HPLC). In some embodiments, the purified RNA polynucleotide comprises 5% or less, 4% or less, 3% or less, 2% or less, 1% or less or is substantially free of short abortive transcript contaminants determined by known methods, such as, e.g., high performance liquid chromatography (HPLC). In some embodiments, the purified RNA polynucleotide has integrity of 95% or greater, 96% or greater, 97% or greater, 98% or greater, or 99% or greater as determined by a known method, such as, e.g., capillary electrophoresis.

In some embodiments, the LNP integrity of the LNP, LNP suspension, lyophilized LNP composition, or LNP formulation of the present disclosure is about 20% or higher, about 25% or higher, about 30% or higher, about 35% or higher, about 40% or higher, about 45% or higher, about 50% or higher, about 55% or higher, about 60% or higher, about 65% or higher, about 70% or higher, about 75% or higher, about 80% or higher, about 85% or higher, about 90% or higher, about 95% or higher, about 96% or higher, about 97% or higher, about 98% or higher, or about 99% or higher.

In some embodiments, the LNP integrity of the LNP, LNP suspension, lyophilized LNP composition, or LNP formulation of the present disclosure is higher than the LNP integrity of the LNP, LNP suspension, lyophilized LNP composition, or LNP formulation produced by a comparable method by about 5% or higher, about 10% or more, about 15% or more, about 20% or more, about 30% or more, about 40% or more, about 50% or more, about 60% or more, about 70% or more, about 80% or more, about 90% or more, about 1 folds or more, about 2 folds or more, about 3 folds or more, about 4 folds or more, about 5 folds or more, about 10 folds or more, about 20 folds or more, about 30 folds or more, about 40 folds or more, about 50 folds or more, about 100 folds or more, about 200 folds or more, about 300 folds or more, about 400 folds or more, about 500 folds or more, about 1000 folds or more, about 2000 folds or more, about 3000 folds or more, about 4000 folds or more, about 5000 folds or more, or about 10000 folds or more.

In some embodiments, the Txo% of the LNP, LNP suspension, lyophilized LNP composition, or LNP formulation of the present disclosure is about 12 months or longer, about 15 months or longer, about 18 months or longer, about 21 months or longer, about 24 months or longer, about 27 months or longer, about 30 months or longer, about 33 months or longer, about 36 months or longer, about 48 months or longer, about 60 months or longer, about 72 months or longer, about 84 months or longer, about 96 months or longer, about 108 months or longer, about 120 months or longer.

In some embodiments, the Txo% of the LNP, LNP suspension, lyophilized LNP composition, or LNP formulation of the present disclosure is longer than the Txo% of the LNP, LNP suspension, lyophilized LNP composition, or LNP formulation produced by a comparable method by about 5% or higher, about 10% or more, about 15% or more, about 20% or more, about 30% or more, about 40% or more, about 50% or more, about 60% or more, about 70% or more, about 80% or more, about 90% or more, about 1 folds or more, about 2 folds or more, about 3 folds or more, about 4 folds or more, about 5 folds or more.

In some embodiments, the T1/2 of the LNP, LNP suspension, lyophilized LNP composition, or LNP formulation of the present disclosure is about 12 months or longer, about 15 months or longer, about 18 months or longer, about 21 months or longer, about 24 months or longer, about 27 months or longer, about 30 months or longer, about 33 months or longer, about 36 months or longer, about 48 months or longer, about 60 months or longer, about 72 months or longer, about 84 months or longer, about 96 months or longer, about 108 months or longer, about 120 months or longer.

In some embodiments, the T1/2 of the LNP, LNP suspension, lyophilized LNP composition, or LNP formulation of the present disclosure is longer than the T1/2 of the LNP, LNP suspension, lyophilized LNP composition, or LNP formulation produced by a comparable method by about 5% or higher, about 10% or more, about 15% or more, about 20% or more, about 30% or more, about 40% or more, about 50% or more, about 60% or more, about 70% or more, about 80% or more, about 90% or more, about 1 folds or more, about 2 folds or more, about 3 folds or more, about 4 folds or more, about 5 folds or more As used herein,"Tx" refers to the amount of time lasted for the nucleic acid integrity (e.g., mRNA integrity) of a LNP, LNP suspension, lyophilized LNP composition, or LNP formulation to degrade to about X of the initial integrity of the nucleic acid (e.g., mRNA) used for the preparation of the LNP, LNP suspension, lyophilized LNP composition, or LNP formulation. For example,"T8o%" refers to the amount of time lasted for the nucleic acid integrity (e.g., mRNA integrity) of a LNP, LNP suspension, lyophilized LNP composition, or LNP formulation to degrade to about 80% of the initial integrity of the nucleic acid (e.g., mRNA) used for the preparation of the LNP, LNP suspension, lyophilized LNP composition, or LNP formulation. For another example,"T1/2" refers to the amount of time lasted for the nucleic acid integrity (e.g., mRNA integrity) of a LNP, LNP suspension, lyophilized LNP composition, or LNP formulation to degrade to about ½ of the initial integrity of the nucleic acid (e.g., mRNA) used for the preparation of the LNP, LNP suspension, lyophilized LNP composition, or LNP formulation.

Lipid nanoparticles may include a lipid component and one or more additional components, such as a therapeutic and/or prophylactic, such as a nucleic acid. A LNP may be designed for one or more specific applications or targets. The elements of a LNP may be selected based on a particular application or target, and/or based on the efficacy, toxicity, expense, ease of use, availability, or other feature of one or more elements. Similarly, the particular formulation of a LNP may be selected for a particular application or target according to, for example, the efficacy and toxicity of particular combination of elements. The efficacy and tolerability of a LNP formulation may be affected by the stability of the formulation.

The lipid component of a LNP may include, for example, a cationic lipid, a phospholipid (such as an unsaturated lipid, e.g., DOPE or DSPC), a PEG lipid, and a structural lipid. The elements of the lipid component may be provided in specific fractions.

In some embodiments, the LNP further comprises a phospholipid, a PEG lipid, a structural lipid, or any combination thereof. Suitable phospholipids, PEG lipids, and structural lipids for the methods of the present disclosure are further disclosed herein.

In some embodiments, the lipid component of a LNP includes a cationic lipid, a phospholipid, a PEG lipid, and a structural lipid. In certain embodiments, the lipid component of the lipid nanoparticle includes about 30 mol % to about 60 mol % cationic lipid, about 0 mol % to about 30 mol % phospholipid, about 18.5 mol % to about 48.5 mol % structural lipid, and about 0 mol % to about 10 mol % of PEG lipid, provided that the total mol % does not exceed 100%. In some embodiments, the lipid component of the lipid nanoparticle includes about 35 mol % to about 55 mol % compound of cationic lipid, about 5 mol % to about 25 mol % phospholipid, about 30 mol % to about 40 mol % structural lipid, and about 0 mol % to about 10 mol % of PEG lipid. In a particular embodiment, the lipid component includes about 50 mol % said cationic lipid, about 10 mol % phospholipid, about 38.5 mol % structural lipid, and about 1.5 mol % of PEG lipid. In another embodiment, the lipid component includes about 40 mol % said cationic lipid, about 20 mol % phospholipid, about 38.5 mol % structural lipid, and about 1.5 mol % of PEG lipid. In some embodiments, the phospholipid may be DOPE or DSPC. In other embodiments, the PEG lipid may be PEG-DMG and/or the structural lipid may be cholesterol.

The amount of a therapeutic and/or prophylactic in a LNP may depend on the size, composition, desired target and/or application, or other properties of the lipid nanoparticle as well as on the properties of the therapeutic and/or prophylactic. For example, the amount of an RNA useful in a LNP may depend on the size, sequence, and other characteristics of the RNA. The relative amounts of a therapeutic and/or prophylactic (i.e. pharmaceutical substance) and other elements (e.g., lipids) in a LNP may also vary. In some embodiments, the wt/wt ratio of the lipid component to a therapeutic and/or prophylactic in a LNP may be from about 5: 1 to about 60:1, such as 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1, and 60:1. For example, the wt/wt ratio of the lipid component to a therapeutic and/or prophylactic may be from about 10:1 to about 40:1. In certain embodiments, the wt/wt ratio is about 20:1. The amount of a therapeutic and/or prophylactic in a LNP may, for example, be measured using absorption spectroscopy (e.g., ultraviolet-visible spectroscopy).

In some embodiments, the ionizable lipid is a compound of Formula (I):

(I)

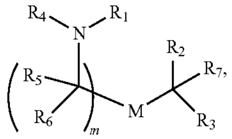

or their N-oxides, or salts or isomers thereof, wherein: Ri is selected from the group consisting of C5-30 alkyl, C5-20 alkenyl, -R*YR", -YR", and -R"M'R'; R2 and R3 are independently selected from the group consisting of H, C1-14 alkyl, C2-14 alkenyl, -R*YR", -YR", and -R*OR", or R2 and R3, together with the atom to which they are attached, form a heterocycle or carbocycle; R4 is selected from the group consisting of hydrogen, a C3-6 carbocycle, —(CH2)nQ, —(CH2)nCHQR, —CHQR, —CQ(R)2, and unsubstituted C1-6 alkyl, where Q is selected from a carbocycle, heterocycle, —OR, —0(CH2)nN(R)2, —C(0)0R, -0C(0)R, -CX3, —CX2H, —CXH2, —CN, —N(R)2, —C(0)N(R)2, -N(R)C(0)R, -N(R)S(0)2R, -N(R)C(0)N(R)2, —N(R)C(S)N(R)2, —N(R)Re, N(R)S(0)2R8, —0(CH2) nOR, —N(R)C(=NR9)N(R)2, -N(R)C(=CHR9)N(R)2, -0C (0)N(R)2J —N(R)C(0)0R, —N(OR)C(0)R, —N(OR)S(0) 2R, —N(OR)C(0)0R, —N(OR)C(0)N(R)2, —N(OR)C(S)N (R)2, —N(OR)C(=NR9)N(R)2, —N(OR)C(=CHR9)N(R)2, —C(=NR9)N(R)2, —C(=NR9)R, —C(0)N(R)OR, and —C(R)N(R)2C(0)0R, and each n is independently selected from 1, 2, 3, 4, and 5; each R5 is independently selected from the group consisting of C1-3 alkyl, C2-3 alkenyl, and H; each Re is independently selected from the group consisting of C1-3 alkyl, C2-3 alkenyl, and H; M and M' are independently selected from -C(0)0-, -OC(O)-, -0C(0)-M"—C(0)0-, —C(0)N(R')-, —N(R')C(0)-, —C(O)-, —C(S)—, —C(S)S—, —SC(S)—, —CH(OH)—, —P(0)(OR')O—, —S(0)2-, —S—S—, an aryl group, and a heteroaryl group, in which M" is a bond, C1-13 alkyl or C2-13 alkenyl; R7 is selected from the group consisting of C1-3 alkyl, C2-3 alkenyl, and H; Re is selected from the group consisting of C3-6 carbocycle and heterocycle; R9 is selected from the group consisting of H, CN, NO2, Ci-6 alkyl, —OR, —S(0)2R, —S(0)2N(R)2, C2-6 alkenyl, C3-6 carbocycle and heterocycle; each R is independently selected from the group consisting of C1-3 alkyl, C2-3 alkenyl, and H; each R' is independently selected from the group consisting of Ci-is alkyl, C2-is alkenyl, -R*YR", -YR", and H; each R" is independently selected from the group consisting of C3-15 alkyl and C3-15 alkenyl; each R* is independently selected from the group consisting of Ci-i2 alkyl and C2-i2 alkenyl; each Y is independently a C3-6 carbocycle; each X is independently selected from the group consisting of F, CI, Br, and I; and m is selected from 5, 6, 7, 8, 9, 10, 11, 12, and 13; and wherein when R4 is —(CH2)nQ, —(CH2)nCHQR, —CHQR, or —CQ(R)2, then (i) Q is not —N(R)2 when n is 1, 2, 3, 4 or 5, or (ii) Q is not 5, 6, or 7-membered heterocycloalkyl when n is 1 or 2. In some embodiments, the ionizable lipid is:

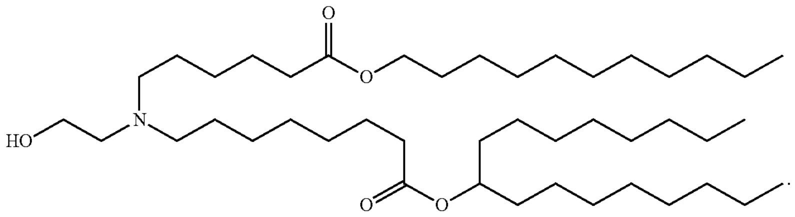 [SMILES: CCCCCCCCCCCOC(=O)CCCCCN(CCO)CCCCCCCC(=O)OC(CCCCCCCC)CCCCCCCC]

In some embodiments, the compounds have the following structure (I):

(IE)

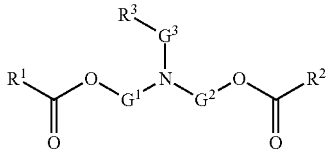

or a pharmaceutically acceptable salt, tautomer, prodrug or stereoisomer thereof, wherein: one of L1 or L2 is —O(C=O)—, —(C=O)O—, —C(=O)—, —O—, —S(O)x—, —S—S—, —C(=O)S—, SC(=O)—, —NRaC(=O)—, —C(=O)NRa—, NRaC(=O)NRa—, —OC(=O)NRa— or —NRaC(=O)O—, and the other of L1 or L2 is —O(C=O)—, —(C=O)O—, —C(=O)—, —O—, —S(O)x , —S—S—, —C(=O)S—, SC(=O)—, —NRaC(=O)—, —C(=O)NRa—, NRaC(=O)NRa—, —OC(=O)NRa— or —NRaC(=O)O— or a direct bond; G1 and G2 are each independently unsubstituted C1-C12 alkylene or C1-C12 alkenylene; G3 is C1-C 24 alkylene, C1-C24 alkenylene, C3-C8 cycloalkylene, C3-C8 cycloalkenylene; Ra is H or C1-C12 alkyl; R1 and R2 are each independently C6-C24 alkyl or C6-C24 alkenyl; R3 is H, OR5, CN, —C(=O)OR4, —OC(=O)R4 or —NR5C(=O)R4, R4 is C1-C12 alkyl; R5 is H or C1-C6 alkyl; and x is 0, 1 or 2. In a preferred embodiment, the ionizable lipid is:

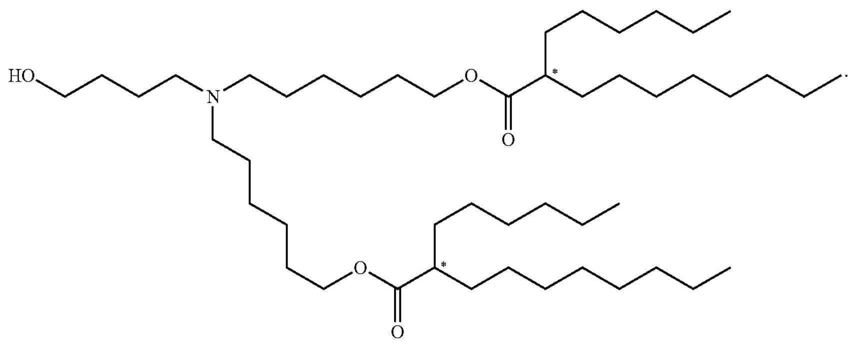

Asterisks (*) indicate chiral centers.

The lipid component of a lipid nanoparticle composition may include one or more molecules comprising polyethylene glycol, such as PEG or PEG-modified lipids. Such species may be alternately referred to as PEGylated lipids. A PEG lipid is a lipid modified with polyethylene glycol. A PEG lipid may be selected from the non-limiting group including PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. In some embodiments, a PEG lipid may be PEG-c-DOMG, PEG-DMG, PEG-DLPE, PEG-DMPE, PEG-DPPC, ora PEG-DSPE lipid. As used herein, the term "PEG lipid" refers to polyethylene glycol (PEG) -modified lipids. Non-limiting examples of PEG lipids include PEG-modified phosphatidylethanolamine and phosphatidic acid, PEG-ceramide conjugates (e.g., PEG-CerCl4 or PEG-CerC20), PEG- modified dialkylamines and PEG-modified I,2-diacyloxpropan-3 -amines. Such lipids are also referred to as PEGylated lipids. In some embodiments, a PEG lipid can be PEG-c-DOMG, PEG- DMG, PEG-DLPE, PEG-DMPE, PEG-DPPC, or a PEG-DSPE lipid. In some embodiments, the PEG-modified lipids are a modified form of PEG DMG. In some embodiments, the PEG-modified lipid is PEG lipid with the formula (IV):

(IV)

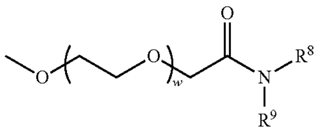

wherein R8 and R9 are each independently a straight or branched, saturated or unsaturated alkyl chain containing from 10 to 30 carbon atoms, wherein the alkyl chain is optionally interrupted by one or more ester bonds; and w has a mean value ranging from 30 to 60. The RNA (e.g., mRNA) vaccines may be utilized in various settings depending on the prevalence of the infection or the degree or level of unmet medical need. The RNA vaccines may be utilized to treat and/or prevent an influenza virus of various genotypes, strains, and isolates. The RNA vaccines typically have superior properties in that they produce much larger antibody titers and produce responses earlier than commercially available anti-viral therapeutic treatments. While not wishing to be bound by theory, it is believed that the RNA vaccines, as mRNA polynucleotides, are better designed to produce the appropriate protein conformation upon translation as the RNA vaccines co-opt natural cellular machinery. Unlike traditional vaccines, which are manufactured ex vivo and may trigger unwanted cellular responses, RNA (e.g., mRNA) vaccines are presented to the cellular system in a more native fashion.

In one aspect, a method of purifying an RNA polynucleotide synthesized by in vitro transcription is provided. The method includes ultrafiltration and diafiltration. In some embodiments, the method does not comprise a chromatography step. In some embodiments, the purified RNA polynucleotide is substantially free of contaminants comprising short abortive RNA species, long abortive RNA species, double- stranded RNA (dsRNA), residual plasmid DNA, residual in vitro transcription enzymes, residual solvent and/or residual salt. In some embodiments, the residual plasmid DNA is ≤ 500 ng DNA/mg RNA. In some embodiments, purity of the purified mRNA is between about 60% and about 100%. In another aspect, a method of producing an RNA polynucleotide-encapsulated LNP is provided. The method includes buffer exchanging the LNPs. The method further includes concentrating the LNPs via flat sheet cassette membranes. In preferred embodiments, the UFDF process does not utilize hollow fiber membranes.

There may be situations in which persons are at risk for infection with more than one strain of influenza virus. RNA (e.g., mRNA) therapeutic vaccines are particularly amenable to combination vaccination approaches due to a number of factors including, but not limited to, speed of manufacture, ability to rapidly tailor vaccines to accommodate perceived geographical threat, and the like. Moreover, because the vaccines utilize the human body to produce the antigenic protein, the vaccines are amenable to the production of larger, more complex antigenic proteins, allowing for proper folding, surface expression, antigen presentation, etc. in the human subject. To protect against more than one strain of influenza, a combination vaccine can be administered that includes RNA (e.g., mRNA) encoding at least one antigenic polypeptide protein (or antigenic portion thereof) of a first influenza virus or organism and further includes RNA encoding at least one antigenic polypeptide protein (or antigenic portion thereof) of a second influenza virus or organism. RNA (e.g., mRNA) can be co-formulated, for example, in a single lipid nanoparticle (LNP) or can be formulated in separate LNPs for co-administration.

Some embodiments of the present disclosure provide influenza virus (influenza) vaccines (or compositions or immunogenic compositions) that include at least one RNA polynucleotide having an open reading frame encoding at least one influenza antigenic polypeptide or an immunogenic fragment thereof (e.g., an immunogenic fragment capable of inducing an immune response to influenza).

In some embodiments, the at least one antigenic polypeptide is one of the defined antigenic subdomains of HA, termed HA1, HA2, or a combination of HA1 and HA2, and at least one antigenic polypeptide selected from neuraminidase (NA), nucleoprotein (NP), matrix protein 1 (M1), matrix protein 2 (M2), non-structural protein 1 (NS1) and non-structural protein 2 (NS2).

In some embodiments, the at least one antigenic polypeptide is HA or derivatives thereof comprising antigenic sequences from HA1 and/or HA2, and at least one antigenic polypeptide selected from NA, NP, M1, M2, NS1 and NS2.

In some embodiments, the at least one antigenic polypeptide is HA or derivatives thereof comprising antigenic sequences from HA1 and/or HA2 and at least two antigenic polypeptides selected from NA, NP, M1, M2, NS1 and NS2.

In some embodiments, a vaccine comprises at least one RNA (e.g., mRNA) polynucleotide having an open reading frame encoding an influenza virus protein, or an immunogenic fragment thereof.

In some embodiments, a vaccine comprises at least one RNA (e.g., mRNA) polynucleotide having an open reading frame encoding multiple influenza virus proteins, or immunogenic fragments thereof.

In some embodiments, a vaccine comprises at least one RNA (e.g., mRNA) polynucleotide having an open reading frame encoding a HA protein, or an immunogenic fragment thereof (e.g., at least one HA1, HA2, or a combination of both).

In some embodiments, a vaccine comprises at least one RNA (e.g., mRNA) polynucleotide having an open reading frame encoding a HA protein, or an immunogenic fragment thereof (e.g., at least one HA1, HA2, or a combination of both, of any one of or a combination of any or all of H1, H2, H3, H4, H5, H6, H7, H8, H9, H10, H11, H12, H13, H14, H15, H16, H17, and/or H18) and at least one other RNA (e.g., mRNA) polynucleotide having an open reading frame encoding a protein selected from a NP protein, a NA protein, a M1 protein, a M2 protein, a NS1 protein and a NS2 protein obtained from influenza virus.

In some embodiments, a vaccine comprises at least one RNA (e.g., mRNA) polynucleotide having an open reading frame encoding a HA protein, or an immunogenic fragment thereof (e.g., at least one any one of or a combination of any or all of H1, H2, H3, H4, H5, H6, H7, H8, H9, H10, H11, H12, H13, H14, H15, H16, H17, and/or H18) and at least two other RNAs (e.g., mRNAs) polynucleotides having two open reading frames encoding two proteins selected from a NP protein, a NA protein, a M1 protein, a M2 protein, a NS1 protein and a NS2 protein obtained from influenza virus.

In some embodiments, a vaccine comprises at least one RNA (e.g., mRNA) polynucleotide having an open reading frame encoding a HA protein, or an immunogenic fragment thereof (e.g., at least one of any one of or a combination of any or all of H1, H2, H3, H4, H5, H6, H7, H8, H9, H10, H11, H12, H13, H14, H15, H16, H17, and/or H18) and at least three other RNAs (e.g., mRNAs) polynucleotides having three open reading frames encoding three proteins selected from a NP protein, a NA protein, a M protein, a M2 protein, a NS1 protein and a NS2 protein obtained from influenza virus.

In some embodiments, a vaccine comprises at least one RNA (e.g., mRNA) polynucleotide having an open reading frame encoding a HA protein, or an immunogenic fragment thereof (e.g., at least one of any one of or a combination of any or all of H1, H2, H3, H4, H5, H6, H7, H8, H9, H10, H11, H12, H13, H14, H15, H16, H17, and/or H18) and at least four other RNAs (e.g., mRNAs) polynucleotides having four open reading frames encoding four proteins selected from a NP protein, a NA protein, a M1 protein, a M2 protein, a NS1 protein and a NS2 protein obtained from influenza virus.

In some embodiments, a vaccine comprises at least one RNA (e.g., mRNA) polynucleotide having an open reading frame encoding a HA protein, or an immunogenic fragment thereof (e.g., at least one of any one of or a combination of any or all of H1, H2, H3, H4, H5, H6, H7, H8, H9, H10, H11, H12, H13, H14, H15, H16, H17, and/or H18) and at least five other RNAs (e.g., mRNAs) polynucleotides having five open reading frames encoding five proteins selected from a NP protein, a NA protein, a M1 protein, a M2 protein, a NS1 protein and a NS2 protein obtained from influenza virus.

In some embodiments, a vaccine comprises at least one RNA (e.g., mRNA) polynucleotide having an open reading frame encoding a HA protein or an immunogenic fragment thereof (e.g., at least one of any one of or a combination of any or all of H1, H2, H3, H4, H5, H6, H7, H8, H9, H10, H11, H12, H13, H14, H15, H16, H17, and/or H18), a NP protein or an immunogenic fragment thereof, a NA protein or an immunogenic fragment thereof, a M1 protein or an immunogenic fragment thereof, a M2 protein or an immunogenic fragment thereof, a NS1 protein or an immunogenic fragment thereof and a NS2 protein or an immunogenic fragment thereof obtained from influenza virus.

Some embodiments of the present disclosure provide the following novel influenza virus polypeptide sequences: H1HA10-Foldon_ΔNgly1; H1HA10TM-PR8 (H1 A/Puerto Rico/8/34 HA); H1HA10-PR8-DS (H1 A/Puerto Rico/8/34 HA; pH1HA10-Ca104-DS (H1 A/California/04/2009 HA); Pandemic H1HA10 from California 04; pH1HA10-ferritin; HA10; Pandemic H1HA10 from California 04; Pandemic H1HA10 from California 04 strain/without foldon and with K68C/R76C mutation for trimerization; H1HA10 from A/Puerto Rico/8/34 strain, without foldon and with Y94D/N95L mutation for trimerization; H1HA10 from A/Puerto Rico/8/34 strain, without foldon and with K68C/R76C mutation for trimerization; H1N1 A/Viet Nam/850/2009; H3N2 A/Wisconsin/67/2005; H7N9 (A/Anhui/1/2013); H9N2 A/Hong Kong/1073/99; H10N8 A/JX346/2013.

Some embodiments of the present disclosure provide influenza virus (influenza) vaccines that include at least one RNA polynucleotide having an open reading frame encoding at least one influenza antigenic polypeptide or an immunogenic fragment of the novel influenza virus polypeptide sequences described above (e.g., an immunogenic fragment capable of inducing an immune response to influenza). In some embodiments, an influenza vaccine comprises at least one RNA (e.g., mRNA) polynucleotide having an open reading frame encoding at least one influenza antigenic polypeptide comprising a modified sequence that is at least 75% (e.g., any number between 75% and 100%, inclusive, e.g., 70%, 80%, 85%, 90%, 95%, 99%, and 100%) identity to an amino acid sequence of the novel influenza virus sequences described above. The modified sequence can be at least 75% (e.g., any number between 75% and 100%, inclusive, e.g., 70%, 80%, 85%, 90%, 95%, 99%, and 100%) identical to an amino acid sequence of the novel influenza virus sequences described above.

Some embodiments of the present disclosure provide an isolated nucleic acid comprising a sequence encoding the novel influenza virus polypeptide sequences described above; an expression vector comprising the nucleic acid; and a host cell comprising the nucleic acid. The present disclosure also provides a method of producing a polypeptide of any of the novel influenza virus sequences described above. A method may include culturing the host cell in a medium under conditions permitting nucleic acid expression of the novel influenza virus sequences described above, and purifying from the cultured cell or the medium of the cell a novel influenza virus polypeptide. The present disclosure also provides antibody molecules, including full length antibodies and antibody derivatives, directed against the novel influenza virus sequences.

In some embodiments, an open reading frame of a RNA (e.g., mRNA) vaccine is codon-optimized. In some embodiments, the open reading frame which the influenza polypeptide or fragment thereof is encoded is codon-optimized. Some embodiments provide use of an influenza vaccine that includes at least one ribonucleic acid (RNA) polynucleotide having an open reading frame encoding at least one influenza antigenic polypeptide or an immunogenic fragment thereof, wherein at least 80% (e.g., 85%, 90%, 95%, 98%, 99%, 100%) of the uracil in the open reading frame have a chemical modification, optionally wherein the vaccine is formulated in a lipid nanoparticle. In some embodiments, 100% of the uracil in the open reading frame have a chemical modification. In some embodiments, a chemical modification is in the 5-position of the uracil. In some preferred embodiments, a chemical modification is a N1-methyl pseudouridine.

In some embodiments, a RNA (e.g., mRNA) vaccine further comprising an adjuvant.

In some embodiments, at least one RNA polynucleotide encodes at least one influenza antigenic polypeptide that attaches to cell receptors.

In some embodiments, at least one RNA polynucleotide encodes at least one influenza antigenic polypeptide that causes fusion of viral and cellular membranes.

In some embodiments, at least one RNA polynucleotide encodes at least one influenza antigenic polypeptide that is responsible for binding of the virus to a cell being infected.

Some embodiments of the present disclosure provide a vaccine that includes at least one ribonucleic acid (RNA) (e.g., mRNA) polynucleotide having an open reading frame encoding at least one influenza antigenic polypeptide, at least one 5' terminal cap and at least one chemical modification, formulated within a lipid nanoparticle.

In some embodiments, a 5' terminal cap is 7mG(5')ppp(5')NlmpNp. In some preferred embodiments, the 5' cap comprises:

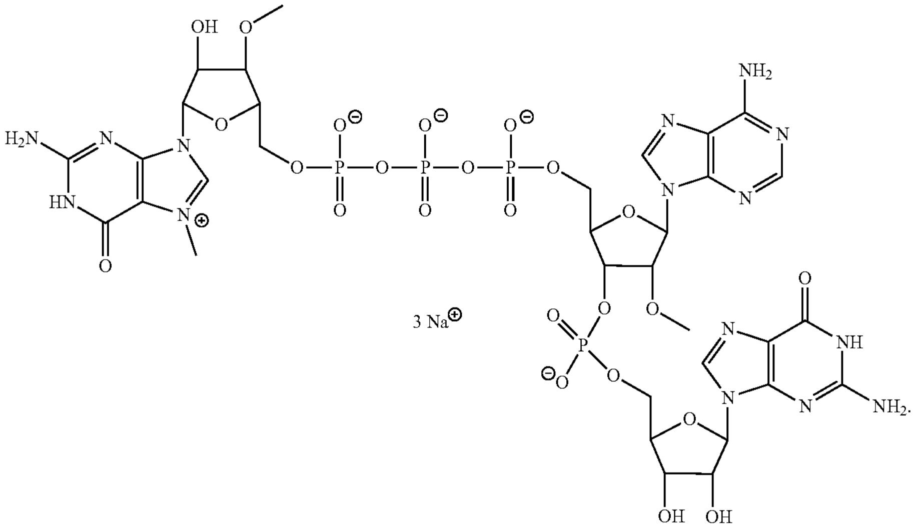 [SMILES: COC1C(COP(=O)([O-])OP(=O)([O-])OP(=O)([O-])OCC2OC(n3cnc4c(N)ncnc43)C(OC)C2OP(=O)([O-])OCC2OC(n3cnc4c(=O)[nH]c(N)nc43)C(O)C2O)OC(n2c[n+](C)c3c(=O)[nH]c(N)nc32)C1O]

In some embodiments, at least one chemical modification is selected from pseudouridine, N1-methylpseudouridine, N1-ethylpseudouridine, 2-thiouridine, 4'-thiouridine, 5-methylcytosine, 5-methyluridine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'—O-methyl uridine. In some embodiments, the chemical modification is in the 5-position of the uracil. In some embodiments, the chemical modification is a N1-methylpseudouridine. In some embodiments, the chemical modification is a N1-ethylpseudouridine.

In some embodiments, a lipid nanoparticle comprises a cationic lipid, a PEG-modified lipid, a sterol and a non-cationic lipid. In some embodiments, a cationic lipid is an ionizable cationic lipid and the non-cationic lipid is a neutral lipid, and the sterol is a cholesterol. In some embodiments, a cationic lipid is selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate (L319), (12Z,15Z)—N,N-dimethyl-2-nonylhenicosa-12,15-dien-1-amine (L608), and N,N-dimethyl-1-[(1S,2R)-2-octylcyclopropyl]heptadecan-8-amine (L530).

Some embodiments of the present disclosure provide a vaccine that includes at least one RNA (e.g., mRNA) polynucleotide having an open reading frame encoding at least one influenza antigenic polypeptide, wherein at least 80% (e.g., 85%, 90%, 95%, 98%, 99%) of the uracil in the open reading frame have a chemical modification, optionally wherein the vaccine is formulated in a lipid nanoparticle (e.g., a lipid nanoparticle comprises a cationic lipid, a PEG-modified lipid, a sterol and a non-cationic lipid).

In some embodiments, 100% of the uracil in the open reading frame have a chemical modification. In some embodiments, a chemical modification is in the 5-position of the uracil. In some embodiments, a chemical modification is a N1-methyl pseudouridine. In some embodiments, 100% of the uracil in the open reading frame have a N1-methyl pseudouridine in the 5-position of the uracil.

In some embodiments, an open reading frame of a RNA (e.g., mRNA) polynucleotide encodes at least one influenza antigenic polypeptides. In some embodiments, the open reading frame encodes at least two, at least five, or at least ten antigenic polypeptides. In some embodiments, the open reading frame encodes at least 100 antigenic polypeptides. In some embodiments, the open reading frame encodes 1-100 antigenic polypeptides.

In some embodiments, a vaccine comprises at least two RNA (e.g., mRNA) polynucleotides, each having an open reading frame encoding at least one influenza antigenic polypeptide. In some embodiments, the vaccine comprises at least five or at least ten RNA (e.g., mRNA) polynucleotides, each having an open reading frame encoding at least one antigenic polypeptide or an immunogenic fragment thereof. In some embodiments, the vaccine comprises at least 100 RNA (e.g., mRNA) polynucleotides, each having an open reading frame encoding at least one antigenic polypeptide. In some embodiments, the vaccine comprises 2-100 RNA (e.g., mRNA) polynucleotides, each having an open reading frame encoding at least one antigenic polypeptide.

Also provided herein is an influenza RNA (e.g., mRNA) vaccine of any one of the foregoing paragraphs formulated in a nanoparticle (e.g., a lipid nanoparticle).

In some embodiments, the nanoparticle has a mean diameter of 50-200 nm. In some embodiments, the nanoparticle is a lipid nanoparticle. In some embodiments, the lipid nanoparticle comprises a cationic lipid, a PEG-modified lipid, a sterol and a non-cationic lipid. In some embodiments, the lipid nanoparticle comprises a molar ratio of about 20-60% cationic lipid, 0.5-15% PEG-modified lipid, 25-55% sterol, and 25% non-cationic lipid. In some embodiments, the cationic lipid is an ionizable cationic lipid and the non-cationic lipid is a neutral lipid, and the sterol is a cholesterol.

In some embodiments, the nanoparticle has a polydispersity value of less than 0.4 (e.g., less than 0.3, 0.2 or 0.1).

In some embodiments, the nanoparticle has a net neutral charge at a neutral pH value.

In some embodiments, the RNA (e.g., mRNA) vaccine is multivalent.

Some embodiments of the present disclosure provide methods of inducing an antigen specific immune response in a subject, comprising administering to the subject any of the RNA (e.g., mRNA) vaccine as provided herein in an amount effective to produce an antigen-specific immune response. In some embodiments, the RNA (e.g., mRNA) vaccine is an influenza vaccine. In some embodiments, the RNA (e.g., mRNA) vaccine is a combination vaccine comprising a combination of influenza vaccines (a broad spectrum influenza vaccine).

In some embodiments, an antigen-specific immune response comprises a T cell response or a B cell response.

In some embodiments, a method of producing an antigen-specific immune response comprises administering to a subject a single dose (no booster dose) of an influenza RNA (e.g., mRNA) vaccine of the present disclosure.

In some embodiments, a method further comprises administering to the subject a second (booster) dose of an influenza RNA (e.g., mRNA) vaccine. Additional doses of an influenza RNA (e.g., mRNA) vaccine may be administered.

In some embodiments, the subjects exhibit a seroconversion rate of at least 80% (e.g., at least 85%, at least 90%, or at least 95%) following the first dose or the second (booster) dose of the vaccine. Seroconversion is the time period during which a specific antibody develops and becomes detectable in the blood. After seroconversion has occurred, a virus can be detected in blood tests for the antibody. During an infection or immunization, antigens enter the blood, and the immune system begins to produce antibodies in response. Before seroconversion, the antigen itself may or may not be detectable, but antibodies are considered absent. During seroconversion, antibodies are present but not yet detectable. Any time after seroconversion, the antibodies can be detected in the blood, indicating a prior or current infection.

In some embodiments, an influenza RNA (e.g., mRNA) vaccine is administered to a subject by intradermal injection, intramuscular injection, or by intranasal administration. In some embodiments, an influenza RNA (e.g., mRNA) vaccine is administered to a subject by intramuscular injection.

Some embodiments, of the present disclosure provide methods of inducing an antigen specific immune response in a subject, including administering to a subject an influenza RNA (e.g., mRNA) vaccine in an effective amount to produce an antigen specific immune response in a subject. Antigen-specific immune responses in a subject may be determined, in some embodiments, by assaying for antibody titer (for titer of an antibody that binds to an influenza antigenic polypeptide) following administration to the subject of any of the influenza RNA (e.g., mRNA) vaccines of the present disclosure. In some embodiments, the anti-antigenic polypeptide antibody titer produced in the subject is increased by at least 1 log relative to a control. In some embodiments, the anti-antigenic polypeptide antibody titer produced in the subject is increased by 1-3 log relative to a control.

In some embodiments, the anti-antigenic polypeptide antibody titer produced in a subject is increased at least 2 times relative to a control. In some embodiments, the anti-antigenic polypeptide antibody titer produced in the subject is increased at least 5 times relative to a control. In some embodiments, the anti-antigenic polypeptide antibody titer produced in the subject is increased at least 10 times relative to a control. In some embodiments, the anti-antigenic polypeptide antibody titer produced in the subject is increased 2-10 times relative to a control.

In some embodiments, the control is an anti-antigenic polypeptide antibody titer produced in a subject who has not been administered a RNA (e.g., mRNA) vaccine of the present disclosure. In some embodiments, the control is an anti-antigenic polypeptide antibody titer produced in a subject who has been administered a live attenuated or inactivated influenza, or wherein the control is an anti-antigenic polypeptide antibody titer produced in a subject who has been administered a recombinant or purified influenza protein vaccine. In some embodiments, the control is an anti-antigenic polypeptide antibody titer produced in a subject who has been administered an influenza virus-like particle (VLP) vaccine.

A RNA (e.g., mRNA) vaccine of the present disclosure is administered to a subject in an effective amount (an amount effective to induce an immune response). In some embodiments, the effective amount is a dose equivalent to an at least 2-fold, at least 4-fold, at least 10-fold, at least 100-fold, at least 1000-fold reduction in the standard of care dose of a recombinant influenza protein vaccine, wherein the anti-antigenic polypeptide antibody titer produced in the subject is equivalent to an anti-antigenic polypeptide antibody titer produced in a control subject administered the standard of care dose of a recombinant influenza protein vaccine, a purified influenza protein vaccine, a live attenuated influenza vaccine, an inactivated influenza vaccine, or an influenza VLP vaccine. In some embodiments, the effective amount is a dose equivalent to 2-1000-fold reduction in the standard of care dose of a recombinant influenza protein vaccine, wherein the anti-antigenic polypeptide antibody titer produced in the subject is equivalent to an anti-antigenic polypeptide antibody titer produced in a control subject administered the standard of care dose of a recombinant influenza protein vaccine, a purified influenza protein vaccine, a live attenuated influenza vaccine, an inactivated influenza vaccine, or an influenza VLP vaccine.

In some embodiments, the control is an anti-antigenic polypeptide antibody titer produced in a subject who has been administered a virus-like particle (VLP) vaccine comprising structural proteins of influenza.

In some embodiments, the RNA (e.g., mRNA) vaccine is formulated in an effective amount to produce an antigen specific immune response in a subject.

In some embodiments, the effective amount is a total dose of 25 μg to 1000 μg, or 50 μg to 1000 μg. In some embodiments, the effective amount is a total dose of 100 μg. In some embodiments, the effective amount is a dose of 25 μg administered to the subject a total of two times. In some embodiments, the effective amount is a dose of 100 μg administered to the subject a total of two times. In some embodiments, the effective amount is a dose of 400 μg administered to the subject a total of two times. In some embodiments, the effective amount is a dose of 500 μg administered to the subject a total of two times.

In some embodiments, the efficacy (or effectiveness) of a RNA (e.g., mRNA) vaccine is greater than 60%. In some embodiments, the RNA (e.g., mRNA) polynucleotide of the vaccine at least one Influenza antigenic polypeptide.

Vaccine efficacy may be assessed using standard analyses. For example, vaccine efficacy may be measured by double-blind, randomized, clinical controlled trials. Vaccine efficacy may be expressed as a proportionate reduction in disease attack rate (AR) between the unvaccinated (ARU) and vaccinated (ARV) study cohorts and can be calculated from the relative risk (RR) of disease among the vaccinated group with use of the following formulas:

$$\text{Efficacy}=(\text{ARU-ARV})/\text{ARU}\times 100;\ \text{and Efficacy}=(1-\text{RR})\times 100.$$

Likewise, vaccine effectiveness may be assessed using standard analyses. Vaccine effectiveness is an assessment of how a vaccine (which may have already proven to have high vaccine efficacy) reduces disease in a population. This measure can assess the net balance of benefits and adverse effects of a vaccination program, not just the vaccine itself, under natural field conditions rather than in a controlled clinical trial. Vaccine effectiveness is proportional to vaccine efficacy (potency) but is also affected by how well target groups in the population are immunized, as well as by other non-vaccine-related factors that influence the 'real-world' outcomes of hospitalizations, ambulatory visits, or costs. For example, a retrospective case control analysis may be used, in which the rates of vaccination among a set of infected cases and appropriate controls are compared. Vaccine effectiveness may be expressed as a rate difference, with use of the odds ratio (OR) for developing infection despite vaccination: Effectiveness=(1—OR)×100. In some embodiments, the efficacy (or effectiveness) of a RNA (e.g., mRNA) vaccine is at least 65%, at least 70%, at least 75%, at least 80%, at least 85%, or at least 90%.

In some embodiments, the vaccine immunizes the subject against Influenza for up to 2 years. In some embodiments, the vaccine immunizes the subject against Influenza for more than 2 years, more than 3 years, more than 4 years, or for 5-10 years.

In some embodiments, the subject is about 5 years old or younger. For example, the subject may be between the ages of about 1 year and about 5 years (e.g., about 1, 2, 3, 5 or 5 years), or between the ages of about 6 months and about 1 year (e.g., about 6, 7, 8, 9, 10, 11 or 12 months). In some embodiments, the subject is about 12 months or younger (e.g., 12, 11, 10, 9, 8, 7, 6, 5, 4, 3, 2 months or 1 month). In some embodiments, the subject is about 6 months or younger.

In some embodiments, the subject was born full term (e.g., about 37-42 weeks). In some embodiments, the subject was born prematurely, for example, at about 36 weeks of gestation or earlier (e.g., about 36, 35, 34, 33, 32, 31, 30, 29, 28, 27, 26 or 25 weeks). For example, the subject may have been born at about 32 weeks of gestation or earlier. In some embodiments, the subject was born prematurely between about 32 weeks and about 36 weeks of gestation. In such subjects, a RNA (e.g., mRNA) vaccine may be administered later in life, for example, at the age of about 6 months to about 5 years, or older.

In some embodiments, the subject is a young adult between the ages of about 20 years and about 50 years (e.g., about 20, 25, 30, 35, 40, 45 or 50 years old).

In some embodiments, the subject is an elderly subject about 60 years old, about 70 years old, or older (e.g., about 60, 65, 70, 75, 80, 85 or 90 years old).

In some embodiments, the subject has been exposed to influenza (e.g., *C. trachomatis*); the subject is infected with influenza (e.g., *C. trachomatis*); or subject is at risk of infection by influenza (e.g., *C. trachomatis*).

In some embodiments, the subject has been exposed to betacoronavirus (e.g., SARS-CoV-2); the subject is infected with betacoronavirus (e.g., SARS-CoV-2); or subject is at risk of infection by betacoronavirus (e.g., SARS-CoV-2).

In some embodiments, the subject has received at least one dose of an immunogenic composition against betacoronavirus (e.g., SARS-CoV-2), e.g., selected from any one of COMIRNATY®, the Pfizer-BioNTech COVID-19 vaccine, the Moderna mRNA-1273 COVID-19 vaccine, and the Janssen COVID-19 vaccine; the subject has received at least two doses of an immunogenic composition against betacoronavirus (e.g., SARS-CoV-2); the subject is receiving at least one dose of an immunogenic composition against betacoronavirus (e.g., SARS-CoV-2), e.g., selected from any one of COMIRNATY®, the Pfizer-BioNTech COVID-19 vaccine, the Moderna mRNA-1273 COVID-19 vaccine, and the Janssen COVID-19 vaccine; or the subject is being administered an immunogenic composition against betacoronavirus (e.g., SARS-CoV-2), e.g., selected from any one of COMIRNATY®, the Pfizer-BioNTech COVID-19 vaccine, the Moderna mRNA-1273 COVID-19 vaccine, and the Janssen COVID-19 vaccine at risk of infection by betacoronavirus (e.g., SARS-CoV-2) concomitantly, simultaneously, or within 12-48 hours of any one of the immunogenic compositions against influenza disclosed herein.

In some embodiments, the subject is immunocompromised (has an impaired immune system, e.g., has an immune disorder or autoimmune disorder).

In some embodiments the nucleic acid vaccines described herein are chemically modified. In other embodiments the nucleic acid vaccines are unmodified.

Yet other aspects provide compositions for and methods of vaccinating a subject comprising administering to the subject a nucleic acid vaccine comprising one or more RNA polynucleotides having an open reading frame encoding a first virus antigenic polypeptide, wherein the RNA polynucleotide does not include a stabilization element, and wherein an adjuvant is not coformulated or co-administered with the vaccine.

In other aspects the invention is a composition for or method of vaccinating a subject comprising administering to the subject a nucleic acid vaccine comprising one or more RNA polynucleotides having an open reading frame encoding a first antigenic polypeptide wherein a dosage of between 10 μg/kg and 400 μg/kg of the nucleic acid vaccine is administered to the subject. In some embodiments the dosage of the RNA polynucleotide is 1-5 μg, 5-10 μg, 10-15 μg, 15-20 μg, 10-25 μg, 20-25 μg, 20-50 μg, 30-50 μg, 40-50 μg, 40-60 μg, 60-80 μg, 60-100 μg, 50-100 μg, 80-120 μg, 40-120 μg, 40-150 μg, 50-150 μg, 50-200 μg, 80-200 μg, 100-200 μg, 120-250 μg, 150-250 μg, 180-280 μg, 200-300 μg, 50-300 μg, 80-300 μg, 100-300 μg, 40-300 μg, 50-350 μg, 100-350 μg, 200-350 μg, 300-350 μg, 320-400 μg, 40-380 μg, 40-100 μg, 100-400 μg, 200-400 μg, or 300-400 μg per dose. In some embodiments, the nucleic acid vaccine is administered to the subject by intradermal or intramuscular injection. In some embodiments, the nucleic acid vaccine is administered to the subject on day zero. In some embodiments, a second dose of the nucleic acid vaccine is administered to the subject on day twenty-one.

In some embodiments, a dosage of 25 micrograms of the RNA polynucleotide is included in the nucleic acid vaccine administered to the subject. In some embodiments, a dosage of 100 micrograms of the RNA polynucleotide is included in the nucleic acid vaccine administered to the subject. In some embodiments, a dosage of 50 micrograms of the RNA polynucleotide is included in the nucleic acid vaccine administered to the subject. In some embodiments, a dosage of 75 micrograms of the RNA polynucleotide is included in the nucleic acid vaccine administered to the subject. In some embodiments, a dosage of 150 micrograms of the RNA polynucleotide is included in the nucleic acid vaccine administered to the subject. In some embodiments, a dosage of 400 micrograms of the RNA polynucleotide is included in the nucleic acid vaccine administered to the subject. In some embodiments, a dosage of 200 micrograms of the RNA polynucleotide is included in the nucleic acid vaccine administered to the subject. In some embodiments, the RNA polynucleotide accumulates at a 100-fold higher level in the local lymph node in comparison with the distal lymph node. In other embodiments the nucleic acid vaccine is chemically modified and in other embodiments the nucleic acid vaccine is not chemically modified.

Aspects of the disclosure provide a nucleic acid vaccine comprising one or more RNA polynucleotides having an open reading frame encoding a first antigenic polypeptide, wherein the RNA polynucleotide does not include a stabilization element, and a pharmaceutically acceptable carrier or excipient, wherein an adjuvant is not included in the vaccine. In some embodiments, the stabilization element is a histone stem-loop. In some embodiments, the stabilization element is a nucleic acid sequence having increased GC content relative to wild type sequence.

Aspects of the disclosure provide nucleic acid vaccines comprising one or more RNA polynucleotides having an open reading frame encoding a first antigenic polypeptide, wherein the RNA polynucleotide is present in the formulation for in vivo administration to a host, which confers an antibody titer superior to the criterion for seroprotection for the first antigen for an acceptable percentage of human subjects. In some embodiments, the antibody titer produced by the mRNA vaccines of the disclosure is a neutralizing antibody titer. In some embodiments the neutralizing antibody titer is greater than a protein vaccine. In other embodiments the neutralizing antibody titer produced by the mRNA vaccines of the disclosure is greater than an adjuvanted protein vaccine. In yet other embodiments the neutralizing antibody titer produced by the mRNA vaccines of the disclosure is 1,000-10,000, 1,200-10,000, 1,400-10,000, 1,500-10,000, 1,000-5,000, 1,000-4,000, 1,800-10,000, 2000-10,000, 2,000-5,000, 2,000-3,000, 2,000-4,000, 3,000-5,000, 3,000-4,000, or 2,000-2,500. A neutralization titer is typically expressed as the highest serum dilution required to achieve a 50% reduction in the number of plaques.

Also provided are nucleic acid vaccines comprising one or more RNA polynucleotides having an open reading frame encoding a first antigenic polypeptide, wherein the RNA polynucleotide is present in a formulation for in vivo administration to a host for eliciting a longer lasting high antibody titer than an antibody titer elicited by an mRNA vaccine having a stabilizing element or formulated with an adjuvant and encoding the first antigenic polypeptide. In some embodiments, the RNA polynucleotide is formulated to produce a neutralizing antibodies within one week of a single administration. In some embodiments, the adjuvant is selected from a cationic peptide and an immunostimulatory nucleic acid. In some embodiments, the cationic peptide is protamine.

Aspects provide nucleic acid vaccines comprising one or more RNA polynucleotides having an open reading frame comprising at least one chemical modification or optionally no modified nucleotides, the open reading frame encoding a first antigenic polypeptide, wherein the RNA polynucleotide is present in the formulation for in vivo administration to a host such that the level of antigen expression in the host significantly exceeds a level of antigen expression produced by an mRNA vaccine having a stabilizing element or formulated with an adjuvant and encoding the first antigenic polypeptide.

Other aspects provide nucleic acid vaccines comprising one or more RNA polynucleotides having an open reading frame comprising at least one chemical modification or optionally no modified nucleotides, the open reading frame encoding a first antigenic polypeptide, wherein the vaccine has at least 10-fold less RNA polynucleotide than is required for an unmodified mRNA vaccine to produce an equivalent antibody titer. In some embodiments, the RNA polynucleotide is present in a dosage of 25-100 micrograms.

Aspects of the disclosure also provide a unit of use vaccine, comprising between 10 ug and 400 ug of one or more RNA polynucleotides having an open reading frame comprising at least one chemical modification or optionally no modified nucleotides, the open reading frame encoding a first antigenic polypeptide, and a pharmaceutically acceptable carrier or excipient, formulated for delivery to a human subject. In some embodiments, the vaccine further comprises a cationic lipid nanoparticle.

Aspects of the disclosure provide methods of creating, maintaining or restoring antigenic memory to a virus strain in an individual or population of individuals comprising administering to said individual or population an antigenic memory booster nucleic acid vaccine comprising (a) at least one RNA polynucleotide, said polynucleotide comprising at least one chemical modification or optionally no modified nucleotides and two or more codon-optimized open reading frames, said open reading frames encoding a set of reference antigenic polypeptides, and (b) optionally a pharmaceutically acceptable carrier or excipient. In some embodiments, the vaccine is administered to the individual via a route selected from the group consisting of intramuscular administration, intradermal administration, and subcutaneous administration. In some embodiments, the administering step comprises contacting a muscle tissue of the subject with a device suitable for injection of the composition. In some embodiments, the administering step comprises contacting a muscle tissue of the subject with a device suitable for injection of the composition in combination with electroporation.

In some aspects, methods of inducing an antigen specific immune response in a subject are provided. The method includes administering to the subject an influenza RNA composition in an amount effective to produce an antigen specific immune response. In some embodiments, an antigen specific immune response comprises a T cell response or a B cell response. In some embodiments, an antigen specific immune response comprises a T cell response and a B cell response. In some embodiments, a method of producing an antigen specific immune response involves a single administration of the vaccine. In some embodiments, a method further includes administering to the subject a booster dose of the vaccine. In some embodiments, a vaccine is administered to the subject by intradermal or intramuscular injection.

Aspects of the disclosure provide methods of vaccinating a subject comprising administering to the subject a single dosage of between 25 ug/kg and 400 ug/kg of a nucleic acid vaccine comprising one or more RNA polynucleotides having an open reading frame encoding a first antigenic polypeptide in an effective amount to vaccinate the subject.

Other aspects provide nucleic acid vaccines comprising one or more RNA polynucleotides having an open reading frame comprising at least one chemical modification, the open reading frame encoding a first antigenic polypeptide, wherein the vaccine has at least 10-fold less RNA polynucleotide than is required for an unmodified mRNA vaccine to produce an equivalent antibody titer. In some embodiments, the RNA polynucleotide is present in a dosage of 25-100 micrograms.

Other aspects provide nucleic acid vaccines comprising an LNP formulated RNA polynucleotide having an open reading frame comprising no nucleotide modifications (unmodified), the open reading frame encoding a first antigenic polypeptide, wherein the vaccine has at least 10-fold less RNA polynucleotide than is required for an unmodified mRNA vaccine not formulated in a LNP to produce an equivalent antibody titer. In some embodiments, the RNA polynucleotide is present in a dosage of 25-100 micrograms.

The data presented in the Examples demonstrate significant enhanced immune responses using the formulations of the disclosure. Both chemically modified and unmodified RNA vaccines are useful according to the invention. Surprisingly, in contrast to prior art reports that it was preferable to use chemically unmodified mRNA formulated in a carrier to produce vaccines, it is described herein that chemically modified mRNA-LNP vaccines required a much lower effective mRNA dose than unmodified mRNA, i.e., tenfold less than unmodified mRNA when formulated in carriers other than LNP. Both the chemically modified and unmodified RNA vaccines of the disclosure produce better immune responses than mRNA vaccines formulated in a different lipid carrier.

In other aspects the invention encompasses a method of treating an elderly subject age 60 years or older comprising administering to the subject a nucleic acid vaccine comprising one or more RNA polynucleotides having an open reading frame encoding a virus antigenic polypeptide in an effective amount to vaccinate the subject.

In other aspects the invention encompasses a method of treating a young subject age 17 years or younger comprising administering to the subject a nucleic acid vaccine comprising one or more RNA polynucleotides having an open reading frame encoding a virus antigenic polypeptide in an effective amount to vaccinate the subject.

In other aspects the invention encompasses a method of treating an adult subject comprising administering to the subject a nucleic acid vaccine comprising one or more RNA polynucleotides having an open reading frame encoding a virus antigenic polypeptide in an effective amount to vaccinate the subject.

In some aspects the invention is a method of vaccinating a subject with a combination vaccine including at least two nucleic acid sequences encoding antigens wherein the dosage for the vaccine is a combined therapeutic dosage wherein the dosage of each individual nucleic acid encoding an antigen is a sub therapeutic dosage. In some embodiments, the combined dosage is 25 micrograms of the RNA polynucleotide in the nucleic acid vaccine administered to the subject. In some embodiments, the combined dosage is 100 micrograms of the RNA polynucleotide in the nucleic acid vaccine administered to the subject. In some embodiments the combined dosage is 50 micrograms of the RNA polynucleotide in the nucleic acid vaccine administered to the subject. In some embodiments, the combined dosage is 75 micrograms of the RNA polynucleotide in the nucleic acid vaccine administered to the subject. In some embodiments, the combined dosage is 150 micrograms of the RNA polynucleotide in the nucleic acid vaccine administered to the subject. In some embodiments, the combined dosage is 400 micrograms of the RNA polynucleotide in the nucleic acid vaccine administered to the subject.

In preferred aspects, vaccines of the disclosure (e.g., LNP-encapsulated mRNA vaccines) produce prophylactically—and/or therapeutically efficacious levels, concentrations and/or titers of antigen-specific antibodies in the blood or serum of a vaccinated subject. As defined herein, the term antibody titer refers to the amount of antigen-specific antibody produces in s subject, e.g., a human subject. In exemplary embodiments, antibody titer is expressed as the inverse of the greatest dilution (in a serial dilution) that still gives a positive result. In exemplary embodiments, antibody titer is determined or measured by enzyme-linked immunosorbent assay (ELISA). In exemplary embodiments, antibody titer is determined or measured by neutralization assay, e.g., by microneutralization assay. In certain aspects, antibody titer measurement is expressed as a ratio, such as 1:40, 1:100, etc.

In exemplary embodiments of the disclosure, an efficacious vaccine produces an antibody titer of greater than 1:40, greater that 1:100, greater than 1:400, greater than 1:1000, greater than 1:2000, greater than 1:3000, greater than 1:4000, greater than 1:500, greater than 1:6000, greater than 1:7500, greater than 1:10000. In exemplary embodiments, the antibody titer is produced or reached by 10 days following vaccination, by 20 days following vaccination, by 30 days following vaccination, by 40 days following vaccination, or by 50 or more days following vaccination. In exemplary embodiments, the titer is produced or reached following a single dose of vaccine administered to the subject. In other embodiments, the titer is produced or reached following multiple doses, e.g., following a first and a second dose (e.g., a booster dose.) In exemplary aspects of the disclosure, antigen-specific antibodies are measured in units of μg/ml or are measured in units of IU/L (International Units per liter) or mIU/ml (milli International Units per ml). In exemplary embodiments of the disclosure, an efficacious vaccine produces >0.5 μg/ml, >0.1 μg/ml, >0.2 μg/ml, >0.35 μg/ml, >0.5 μg/ml, >1 μg/ml, >2 μg/ml, >5 μg/ml or >10 μg/ml. In exemplary embodiments of the disclosure, an efficacious vaccine produces >10 mIU/ml, >20 mIU/ml, >50 mIU/ml, >100 mIU/ml, >200 mIU/ml, >500 mIU/ml or >1000 mIU/ml. In exemplary embodiments, the antibody level or concentration is produced or reached by 10 days following vaccination, by 20 days following vaccination, by 30 days following vaccination, by 40 days following vaccination, or by 50 or more days following vaccination. In exemplary embodiments, the level or concentration is produced or reached following a single dose of vaccine administered to the subject. In other embodiments, the level or concentration is produced or reached following multiple doses, e.g., following a first and a second dose (e.g., a booster dose.) In exemplary embodiments, antibody level or concentration is determined or measured by enzyme-linked immunosorbent assay (ELISA). In exemplary embodiments, antibody level or concentration is determined or measured by neutralization assay, e.g., by microneutralization assay.

EXAMPLES

Example 1: Drug Product Composition

The drug product composition is an influenza modRNA drug substance targeting the Wisconsin 2021/2022 hemagglutinin.

TABLE 1

Formulation composition of the ready-to-use (RTU) presentation of Flu vaccine drug product

| Components | Function | Concentration, mg/mL |
|---|---|---|
| PF-07829855 Drug substance (mRNA) | Active | 0.1 |
| ALC-0315 | Functional lipid | 1.43 |
| ALC-0159 | Functional lipid | 0.18 |
| DSPC | Structural lipid | 0.31 |
| Cholesterol | Structural lipid | 0.62 |
| Sucrose | Cryoprotectant/Tonicifier | 1.3 |
| Tris/Tromethamine | Buffer, pH 7.4 | 0.18 |
| Tris HCl | | 1.34 |
| Water for injection | Solvent/ehicle | q.s. |

In some embodiments, the immunogenic composition comprising one lipid nanoparticle encapsulated mRNA molecule encoding HA is monovalent and has a dose selected from any one of 1 μg mRNA, 2 μg RNA, 5 μg RNA, and 20 μg RNA.

In some embodiments, the immunogenic composition comprising one lipid nanoparticle encapsulated mRNA molecule encoding HA, a second lipid nanoparticle encapsulated mRNA molecule encoding HA, a third lipid nanoparticle encapsulated mRNA molecule encoding NA, and a fourth lipid nanoparticle encapsulated mRNA molecule encoding NA, wherein the total dose is up to 20 μg RNA.

In some embodiments, the subject is aged 30-50 years.

Example 2: Shipping and Container Closure Information

The Drug Product is shipped frozen on dry ice. The primary container closure is a 2 mL glass Type 1 vial with 13 mm stopper. The drug product should be stored at −60 to −90° C.

Example 3: Dosage Forms

The PF-07252220 influenza modRNA immunogenic composition candidates include one of 3 different dosage forms, selected from 2 monovalent forms and one quadrivalent form, each of which incorporate different constructs of mRNA.

Four Constructs of modRNA:
Wisconsin modRNA (Wisc2019 HA)
Phuket modRNA (Phuk2013 HA)
Washington modRNA (Wash2019 HA)
Cambodia modRNA (Camb2020 HA)

Accordingly, there are 2 monovalent immunogenic compositions (also referred to herein as drug products (DPs)) and one quadrivalent immunogenic composition.

1. Monovalent including Wisconsin modRNA
2. Monovalent including Phuket modRNA
3. Quadrivalent, which includes Wisconsin modRNA, Phuket modRNA, Washington modRNA, and Cambodia modRNA The immunogenic composition is supplied in a 2 mL glass vial sealed with a chlorobutyl rubber stopper and an aluminum seal with flip-off plastic cap (nominal volume of 0.3 mL). 4.2. Components of the Immunogenic Composition The immunogenic composition includes modRNA encoding a strain-specific full length, codon-optimized HA envelope glycoprotein which is responsible for viral binding to target cells and mediating cell entry.

The immunogenic composition is a preservative-free, sterile dispersion of LNPs in aqueous cryoprotectant buffer for IM administration. The immunogenic composition is formulated at 0.1 mg/mL RNA in 10 mM Tris buffer, 300 mM sucrose, pH 7.4 as a single-dose vial with 0.5 mL/vial fill volume, and 0.3 mL nominal volume. 4.2.1. Drug Substance The specific constructs (i.e., Wisconsin modRNA [Wisc2019 HA] and Phuket modRNA [Phuk2013 HA]) or constructs (quadrivalent: Wisconsin modRNA, Phuket modRNA, Washington modRNA, and Cambodia modRNA, in the drug substance (modRNA) are the only active ingredient(s) in the DP. The drug substance is formulated in 10 mM HEPES buffer, 0.1 mM EDTA at pH 7.0 and stored at 20±5° C. in HDPE bottles EVA flexible containers. In addition to the codon-optimized sequence encoding the antigen, the RNA contains common structural elements optimized for mediating high RNA stability and translational efficiency (5'-cap, 5'UTR, 3'-UTR, poly(A) - tail; see table and sequences below). Furthermore, an intrinsic signal peptide (sec) is part of the open reading frame and is translated as an N-terminal peptide. The RNA does not contain any uridines; instead of uridine the modified N1-methylpseudouridine is used in RNA synthesis.

The specific constructs each comprise the following elements:

5'-cap analog)($m_2^{7,3'-O}$Gppp($m_1^{2'-O}$) ApG) for production of RNA containing a cap1 structure is shown below

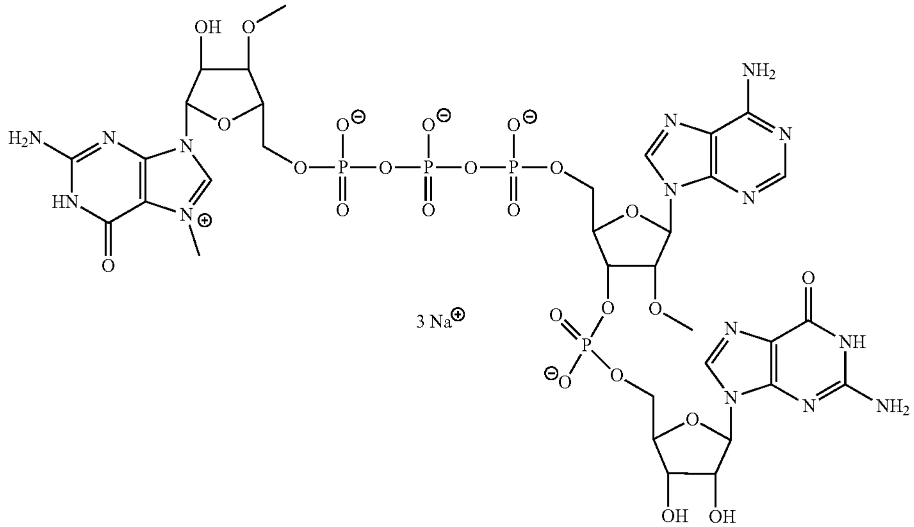 [SMILES: COC1C(COP(=O)([O-])OP(=O)([O-])OP(=O)([O-])OCC2OC(n3cnc4c(N)ncnc43)C(OC)C2OP(=O)([O-])OCC2OC(n3cnc4c(=O)[nH]c(N)nc43)C(O)C2O)OC(n2c[n+](C)c3c(=O)[nH]c(N)nc32)C1O]

3 Na⊕

The cap1 structure (i.e., containing a 2'—O—methyl group on the penultimate nucleoside of the 5'- end of the RNA chain) is incorporated into the drug substance by using a respective cap analog during in vitro transcription. For RNAs with modified uridine nucleotides, the cap1 structure is superior to other cap structures, since cap1 is not recognized by cellular factors such as IFIT1 and, thus, cap1-dependent translation is not inhibited by competition with eukaryotic translation initiation factor 4E . In the context of IFIT1 expression, mRNAs with a cap1 structure give higher protein expression levels.

TABLE 2

| Table of elements | | |
|---|---|---|
| Element | Description | Position |
| cap | A modified 5'-cap1 structure ($m^7G^+m^{3'}$-5'-ppp-5'-Am) | 1-2 |
| 5'-UTR | 5'-untranslated region derived from human alpha-globin RNAwith an optimized Kozak sequence | 3-54 |
| 3'-UTR | The 3' untranslated region comprises two sequence elements derived from the amino-terminal enhancer of split (AES) mRNA and the mitochondrial encoded 12S ribosomal RNA to confer RNA stability and high total protein expression. | 3880-4174 |
| poly(A) | A 110-nucleotide poly(A)-tail consisting of a stretch of 30 adenosine residues, followed by a 10-nucleotide linker sequence and another 70 adenosine residues. | 4175-4284 |

SEQUENCE

GA (SEQ ID NO: 1)
GAAΨAAAC ΨAGΨAΨΨCΨΨ CΨGGΨCCCCA CAGACΨCAGA 50

GAGAACCCGC CACC 54

(SEQ ID NO: 2)
C ΨCGAGCΨGGΨ ACΨGCAΨGCA 3900

CGCAAΨGCΨA GCΨGCCCCΨΨ ΨCCCGΨCCΨG GGΨACCCCGA 3950

GΨCΨCCCCCG

-continued

ACCΨCGGGΨC CCAGGΨAΨGC ΨCCCACCΨCC ACCΨGCCCCA 4000

CΨCACCACCΨ

CΨGCΨAGΨΨC CAGACACCΨC CCAAGCACGC AGCAAΨGCAG 4050

CΨCAAAACGC

ΨΨAGCCΨAGC CACACCCCCA CGGGAAACAG CAGΨGAΨΨAA 4100

CCΨΨΨAGCAA

-continued

ΨAAACGAAAG ΨΨΨAACΨAAG CΨAΨACΨAAC CCCAGGGΨΨG4150

GΨCAAΨΨΨCG ΨGCCAGCCAC ACCCΨGGAGC ΨAGC (SEQ ID NO: 3)
AAAAAA AAAAAAAAAA AAAAAAAAAA 4200

AAAAGCAΨAΨ GACΨAAAAAA AAAAAAAAAA AAAAAAAAAA 4250

AAAAAAAAAA AAAAAAAAAA AAAAAAAAAA AAAAAAAAAA 4284

AAAA
Ψ = 1-methyl-3'-pseudouridlyl

The manufacturing process comprises RNA synthesis via in vitro transcription (IVT) step followed by DNase I and proteinase K digestion steps, purification by ultrafiltration/diafiltration (UFDF), and final filtration and dispense. A platform approach to the IVT, digestion, and purification process steps was used in the production of the four modRNA drug substances. The mRNA drug substance clinical batches were prepared at a scale of 37.6 L starting volume for IVT. The primary objective of the DNase I digestion step is to reduce the size of linear DNA template to enable subsequent removal across the ultrafiltration/diafiltration step. A DNase I solution are added at the end of the final IVT incubation. Temperature and agitation rate from IVT step are maintained during this step. The primary objective of the proteinase K digestion step is to reduce the size of proteins in the reaction mixture for subsequent removal across the ultrafiltration/diafiltration step. Proteinase K solution is added to the reaction vessel and incubated for a predetermined amount of time. Temperature and agitation rate implemented during IVT and DNase digestion steps are maintained during this step. All the material is purified by a single 2-stage Ultrafiltration (UF) and diafiltration (DF) (UFDF) to produce the RNA drug substance. Flat sheet cassette membranes were used as part of the UFDF process.

Preferably, the UFDF process does not utilize hollow fiber membranes. The UFDF step removes small process-related impurities and concentrates, and buffer exchanges the RNA into the final DS formulation.

Based on the retentate RNA concentration determined after diafiltration 2, the diafiltered retentate is then concentrated, if needed, and recovered through a dual-layer filter into a flexible container. The UFDF system is subsequently rinsed and added to the retentate pool through the same dual-layer filter. Formulation buffer may be added. The final pool is then filtered through a second dual-layer filter into HDPE bottle(s).

TABLE 3

Batch Results for Influenza mod RNA Vaccine Wisconsin Drug Substance

| Quality Attribute | Analytical Procedure | Acceptance Criteria | Developmental Material | Developmental Material | Clinical Drug Substance |
|---|---|---|---|---|---|
| Appearance (Clarity) | Clarity | ≤6 NTU | NT | ≤3 NTU | ≤1 NTU |
| Appearance (Coloration) | Coloration | Not more intensely colored than level 7 of the brown (B) color standard. | NT | ≤B9 | ≤B9 |
| PH | Potentiometry | 7.0 ± 0.5 | NT | 6.8 | 6.8 |
| Content (RNA concent ration) | UV spectroscopy | 2.25 ± 0.25 mg/mL | 2.40 mg/mL | 2.28 mg/mL | 2.17 mg/mL |
| RT-PCR | Identity of Encoded RNA Sequence | Identity confirmed | NT | Identity confirmed | Confirmed |
| RNA integrity | Capillary gel electrophoresis | ≥60% | 87% | 86% | 88% |
| RP-HPLC | 5'-Cap | Report Results | 82% | 82% | 83% |
| Residual DNA template | qPCR | ≤500 ng DNA/mg RNA | NT | 23 ng/mg | 112 ng DNA/mg RNA |
| Endotoxin | Endotoxin (LAL) | ≤12.5 EU/mL | NT | 0.35 EU/mL | NMT 1.00 EU/mL |
| Bioburden | Bioburden | ≤1 CFU/10 mL | NT | 0 CFU/10 mL | 0 CFU/10 mL |

Specifical ions only apply to clinical supplies

Abbreviations:

NTU = nephelometric turbidity units;

NT = not tested;

ddPCR = digital droplet polymerase chain reaction;

RP-HPLC = reversed phased high performance liquid chromatography;

qPCR = quantitative polymerase chain reaction;

LAL = limulus amebocyte lysate;

EU = Endotoxin unit;

CFU = Colony forming unit

TABLE 4

| Batch Analyses for Wisconsin Clinical Drug Product | | | |
|---|---|---|---|
| Analytical Procedure | Quality Attributes | Acceptance Criteria | Batch Results |
| Composition and Strength | | | |
| Appearance (Visual) | Appearance | White to off-white suspension | White to off-white suspension |
| Appearance (Particles) | Appearance (Visible Particulates) | May contain white to off-white opaque, amorphous particles | Meets |
| Subvisible particulate matter | Subvisible particles | Particles ≥10 μm: ≤6000 per container<br>Particles ≥25 μm: ≤600 per container | 21 Particles/container<br>1 Particles/container |
| Potentiometry | pH | 7.4 ± 0.5 | 7.4 |
| Osmometry | Osmolality | 240-400 mOsmol/kg | 364 mOsm/kg |
| Dynamic Light Scattering (DLS) | LNP Size | 40-120 nm | 67 nm |
| | LNP Polydispersity | ≤0.3 | 0.2 |
| Fluorescence Assay | RNA Content | 0.074-0.126 mg/mL | 0.104 mg/mL |
| | RNA Encapsulation | ≥80% | 97% |
| HPLC-CAD | ALC-0315 Content | 0.90-1.85 mg/mL | 1.39 mg/mL |
| | ALC-0159 Content | 0.11-0.24 mg/mL | 0.18 mg/mL |
| | DSPC Content | 0.18-0.41 mg/mL | 0.32 mg/mL |
| | Cholesterol Content | 0.36-0.78 mg/mL | 0.61 mg/mL |
| Container content | Vial content (volume) | Not less than 0.30 mL | Not less than labeled volume |
| Identity | | | |
| HPLC-CAD | Lipid identities | Retention times consistent with references (ALC-0315, ALC-0159, Cholesterol, DSPC) | Retention times consistent with references (ALC-0315, ALC-0159, Cholesterol, DSPC) |
| RT-PCR | Identity of encoded RNA sequence(s) | Identity confirmed | Confirmed |
| Purity | | | |
| Capillary Gel Electrophoresis | RNA Integrity | ≥55% intact RNA (release)<br>≥50% intact RNA (stability) | 87% |
| Safety | | | |
| Endotoxin (LAL) | Endotoxin (LAL) | ≤12.5 EU/mL | NMT 5.0 EU/mL |
| Sterility | Sterility | No growth detected | No growth detected |

Specifications only apply to clinical supplies
Abbreviations:
NTU = nephelometric turbidity units;
NT = not tested;
ddPCR = digital droplet polymerase chain reaction;
RP-HPLC = reversed phased high performance liquid chromatography;
qPCR = quantitative polymerase chain reaction;
LAL = limulus amebocyte lysate;
EU = Endotoxin unit;
CFU = Colony forming unit

TABLE 5

| Batch Results for Influenza modRNA Vaccine Phuket Drug Substance | | | | |
|---|---|---|---|---|
| Quality Attribute | Analytical Procedure | Acceptance Criteria | Developmental Material | Clinical Drug Substance |
| Appearance (Clarity) | Clarity | ≤6 NTU | NT | ≤0 NTU |
| Appearance (Coloration) | Coloration | Not more intensely colored than level 7 of the brown (B) color standard. | NT | ≤B9 |

TABLE 5-continued

Batch Results for Influenza modRNA Vaccine Phuket Drug Substance

| Quality Attribute | Analytical Procedure | Acceptance Criteria | Developmental Material | Clinical Drug Substance |
|---|---|---|---|---|
| PH | Potentiometry | 7.0 ± 0.5 | NT | 6.8 |
| Content (RNA concentration) | UV spectroscopy | 2.25 ± 0.25 mg/mL | 2.42 mg/mL | 2.20 mg/mL |
| RT-PCR | Identity of Encoded RNA Sequence | Identity confirmed | NT | Confirmed |
| RNA integrity | Capillary gel electrophoresis | ≥60% | 88% | 87% |
| RP-HPLC | 5'-Cap | Report Results | 85% | 88% |
| Residual DNA template | qPCR | ≤500 ng DNA/mg RNA | NT | 156 ng DNA/mg RNA |
| Endotoxin | Endotoxin (LAL) | ≤12.5 EU/mL | NT | NMT 1.00 EU/mL |
| Bioburden | Bioburden | ≤1 CFU/10 mL | NT | 0 CFU/10 mL |

Specifications only apply to clinical supplies
Abbreviations:
NTU = nephelometric turbidity units;
NT = not tested;
ddPCR = digital droplet polymerase chain reaction;
RP-HPLC = reversed phased high performance liquid chromatography;
qPCR = quantitative polymerase chain reaction;
LAL = limulus amebocyte lysate;
EU = Endotoxin unit;
CFU = Colony forming unit

TABLE 6

Batch Analyses for Phuket Clinical Drug Product

| Analytical Procedure | Quality Attributes | Acceptance Criteria | Batch Results |
|---|---|---|---|
| Composition and Strength | | | |
| Appearance (Visual) | Appearance | White to off-white suspension | White to off-white suspension |
| Appearance (Particles) | Appearance (Visible Particulates) | May contain white to off-white opaque, amorphous particles | Meets |
| Subvisible particulate matter | Subvisible particles | Particles ≥10 µm: ≤6000 per container Particles ≥25 µm: ≤600 per container | 46 Particles/container ≤1 Particles/container |
| Potentiometry | PH | 7.4 ± 0.5 | 7.3 |
| Osmometry | Osmolality | 240-400 mOsmol/kq | 360 mOsm/kg |
| Dynamic Light Scattering (DLS) | LNP Size | 40-120 nm | 80 nm |
| | LNP Polydispersity | ≤0.3 | 0.2 |
| Fluorescence Assay | RNA Content | 0.074-0.126 mg/mL | 0.086 mg/mL |
| | RNA Encapsulation | ≥80% | 94% |
| HPLC-CAD | ALC-0315 Content | 0.90-1.85 mg/mL | 1.39 mg/mL |
| | ALC-0159 Content | 0.11-0.24 mg/mL | 0.17 mg/mL |
| | DSPC Content | 0.18-0.41 mg/mL | 0.29 mg/mL |
| | Cholesterol Content | 0.36-0.78 mg/mL | 0.59 mg/mL |
| Container content | Vial content (volume) | Not less than 0.30 mL | Not less than labeled volume |
| Identity | | | |
| HPLC-CAD | Lipid identities | Retention times consistent with references (ALC-0315, ALC-0159, Cholesterol, DSPC) | Retention times consistent with references (ALC-0315, ALC-0159, Cholesterol, DSPC) |
| RT-PCR | Identity of encoded RNA sequence(s) | Identity confirmed | Confirmed |
| Purity | | | |
| Capillary Gel Electrophoresis | RNA Integrity | ≥55% intact RNA (release) | 85% |

TABLE 6-continued

| Batch Analyses for Phuket Clinical Drug Product | | | |
|---|---|---|---|
| Analytical Procedure | Quality Attributes | Acceptance Criteria | Batch Results |
| Safety | | | |
| Endotoxin (LAL) | Endotoxin (LAL) | ≤12.5 EU/mL | NMT 5.0 EU/mL |
| Sterility | Sterility | No growth detected | No growth detected |

TABLE 7

Batch Results for Influenza modRNA Vaccine Cambodia Drug Substance

| Quality Attribute | Analytical Procedure | Acceptance Criteria | Developmental Material | Clinical Drug Substance |
|---|---|---|---|---|
| Appearance (Clarity) | Clarity | ≤6 NTU | NT | ≤1 NTU |
| Appearance (Coloration) | Coloration | Not more intensely colored than level 7 of the brown (B) color standard. | NT | ≤B9 |
| PH | Potentiometry | 7.0 ± 0.5 | NT | 6.8 |
| Content (RNA concentration) | UV spectroscopy | 2.25 ± 0.25 mg/mL | 2.31 mg/mL | 2.18 mg/mL |
| ddPCR | Identity of Encoded RNA Sequence | Identity confirmed | NT | Confirmed |
| RNA integrity | Capillary gel electrophoresis | ≥60% | 90% | 75% |
| RP-HPLC | 5'-Cap | Report Results | 80% | 86% |
| Residual DNA template | qPCR | ≤1500 ng DNA/mg RNA | NT | 221 ng DNA/mg RNA |
| Endotoxin | Endotoxin (LAL) | ≤12.5 EU/mL | NT | NMT 1.00 EU/mL |
| Bioburden | Bioburden | ≤1 CFU/10 mL | NT | 0 CFU/10 mL |

Specifications only apply to clinical supplies
Abbreviations:
NTU = nephelometric turbidity units;
NT = not tested;
ddPCR = digital droplet polymerase chain reaction;
RP-HPLC = reversed phased high performance liquid chromatography;
qPCR = quantitative polymerase chain reaction;
LAL = limulus amebocyte lysate;
EU = Endotoxin unit;
CFU = Colony forming unit

TABLE 8

Batch Results for Influenza modRNA Vaccine Washington Drug Substance

| Quality Attribute | Analytical Procedure | Acceptance Criteria | Developmental Material | Clinical Drug Substance |
|---|---|---|---|---|
| Appearance (Clarity) | Clarity | ≤6 NTU | NT | ≤1 NTU |
| Appearance (Coloration) | Coloration | Not more intensely colored than level 7 of the brown (B) color standard. | NT | ≤B9 |
| PH | Potentiometry | 7.0 ± 0.5 | NT | 6.9 |
| Content (RNA concentration) | UV spectroscopy | 2.25 ± 0.25 mg/mL | 2.41 mg/mL | 2.22 mg/mL |
| RT-PCR | Identity of Encoded RNA Sequence | Identity confirmed | NT | Confirmed |

TABLE 8-continued

| Batch Results for Influenza modRNA Vaccine Washington Drug Substance | | | | |
|---|---|---|---|---|
| Quality Attribute | Analytical Procedure | Acceptance Criteria | Developmental Material | Clinical Drug Substance |
| RNA integrity | Capillary gel electrophoresis | ≥60% | 87% | 83% |
| RP-HPLC | 5'-Cap | Report Results | 86% | 87% |
| Residual DNA template | qPCR | ≤1500 ng DNA/mg RNA | NT | 364 ng DNA/mg RNA |
| Endotoxin | Endotoxin (LAL) | ≤12.5 EU/mL | NT | NMT 1.00 EU/mL |
| Bioburden | Bioburden | ≤1 CFU/10 mL | NT | 0 CFU/10 mL |

Specifications only apply to clinical supplies
Abbreviations:
NTU = nephelometric turbidity units;
NT = not tested;
ddPCR = digital droplet polymerase chain reaction;
RP-HPLC = reversed phased high performance liquid chromatography;
qPCR = quantitative polymerase chain reaction;
LAL = limulus amebocyte lysate;
EU = Endotoxin unit;
CFU = Colony forming unit The process parameters for formation and stabilization of lipid nanoparticles are summarized in Table 10.

Table 10. Process Parameters for Formation and Stabilization of LNPs

Process Parameter Acceptable Range
Temperature of aqueous phase 15-25° C.
Temperature of organic phase 15-25° C.
Flow rate ratio of citrate buffer to diluted drug substance for preparation of aqueous phase 4:1[a]
Flow rate ratio of LNP suspension to citrate buffer for stabilization 2:1[a]
LNP collection vessel temperature 2-25° C.
[a]Target set-point during LNP formation. Ratios may be calculated from input flow rates.

Lipid Nanoparticle (LNP) Formation and Stabilization

To form the LNPs, the citrate buffer is combined in-line with the diluted drug substance in a 4:1 flowrate ratio to create the aqueous phase. The organic and aqueous phases are fed into one or more T-mixer(s) to form the LNPs. Post formation of the LNP suspension, the LNPs are stabilized via in-line dilution with citrate buffer in a 2:1 ratio of LNP suspension to citrate buffer and then collected in a vessel which is maintained at 2-25° C.

Buffer Exchange and Concentration

To prepare for the Buffer Exchange and Concentration operation, the tangential flow filtration (TFF) membranes are flushed with Tris buffer for equilibration.

The LNPs are processed through a tangential flow filtration (TFF) unit operation where they are concentrated and then buffer exchanged with 2 diavolumes of tris buffer to remove ethanol from the suspension. The LNPs are then concentrated further and buffer exchanged with ≥8 additional diavolumes of Tris buffer.

TABLE 9

| In-Process Controls During Drug Product Manufacturing | | |
|---|---|---|
| Description | In-process control | Acceptance criteria |
| LNP formation and stabilization | pH of citrate buffer | 4.0 ± 0.1 |
| Buffer exchange, concentration and filtration | pH of Tris buffer | 7.5 ± 0.2 |
| Concentration adjustment and addition of cryoprotectant | pH of Sucrose/Tris buffer | 7.5 ± 0.2 |
| Concentration adjustment and addition of cryoprotectant | RNA content prior to Tris addition | ≥0.133 mg/mL (Action limit) |
| Sterile filtration | Bioburden prior to sterile filtration | ≤2 CFU/20 mL |
| Sterile filtration | Filter integrity pre-use/post-use sterile filtration | Pass |
| Aseptic filling | Fill weight (measurement) | 0.5 mL (0.52 g) ± 4% |

4.2.2. Excipients

The excipients Tromethamine (Tris base) and Tris Hydrochloride (HCl) present in the LNP drug product are buffer components used in pharmaceuticals and suitable to achieve the desired product pH. Sucrose is also included and was selected for its stabilizing effect to enable storage as a frozen composition prior to distribution and refrigeration at point of use. The 4 lipid excipients in the immunogenic composition are both functional and structural lipids utilized as part of the modRNA platform.

4.3. Dosage and Administration

The immunogenic composition is diluted as needed with normal saline, either by in-vial dilution or syringe to syringe mixing, prior to administration of the monovalent compositions or combination for the bivalent compositions.

For monovalent dosing, the immunogenic composition is dosed in the range of 3.75 to 30 μg per dose with an injection volume of 0.3 mL. Except for the 30-μg dose, dilution with sterile 0.9% sodium chloride (normal saline) is required for dosing. The 4 dose levels are:

3.75 μg mRNA
7.5 μg mRNA
15 μg mRNA
30 μg mRNA

The Wisconsin immunogenic composition is also dosed as a bivalent vaccine in combination with the Phuket immunogenic composition in a total delivered volume of 0.3 mL. The proposed dosing range (total RNA) and ratios of Wisconsin (VV) immunogenic composition to Phuket (P) immunogenic composition in the bivalent immunogenic composition are:

15 μg at 1W:1P (7.5 μg A+7.5 μg B)
30 μg at 1W:1P (15 μg A+15 μg B)
22.5 μg at 1W:2P (7.5 μg A+15 μg B)
18.75 μg at 1W:4P (3.75 μg A+15 μg B)

For quadrivalent dosing, the immunogenic composition is dosed with an injection volume of 0.3 mL containing each of the 4 modRNA sequences for a total dose of up to 30 μg. No dilution is required for administration of the quadrivalent immunogenic composition Container Closure System.

The type I borosilicate glass vials meet USP <660>, Ph. Eur. 3.2.1, and JP 7.01 compendial requirements for hydrolytic resistance for Type I glass containers. The chlorobutyl elastomeric stoppers meet USP <381>, Ph. Eur. 3.2.9 and JP 7.03 compendial chemical testing requirements for elastomeric closures.

4.4. Storage and Transport, Label and Pack of the Drug Product

The immunogenic composition is frozen and stored at ultralow temperature (ULT) (−90° C. to 60° C.) for long-term storage.

The influenza modRNA immunogenic composition is comprised of one or more nucleoside-modified mRNAs that encode the full-length HA glycoprotein derived from seasonal human influenza strains. The modRNA is formulated with 2 functional and 2 structural lipids, which protect the modRNA from degradation and enable transfection of the modRNA into host cells after IM injection. Influenza HA is the most abundant envelope glycoprotein on the surface of influenza A and B virions.

The primary pharmacology of the influenza modRNA immunogenic composition was evaluated in nonclinical studies in vitro and in vivo. In vitro and in vivo studies demonstrated the mechanism-of-action for the influenza modRNA immunogenic composition, which is to encode influenza HA that induces an immune response characterized by both a strong functional antibody responses and a Th1-type CD4+ and an IFNg+ CD8+ T-cell response. Efficient in vitro expression of the HA glycoprotein from influenza modRNA vaccines was demonstrated in cultured cells. Mouse and rat immunogenicity studies demonstrated that influenza modRNA vaccines elicited strong functional and neutralizing antibody responses and CD4+ and CD8+ T-cell responses. Immunogenicity studies in mice, benchmarked against a licensed, adjuvanted inactivated influenza vaccine, also support the potential use of a multivalent influenza modRNA immunogenic composition formulation to target 4 different influenza virus strains.

A Lipid Nanoparticle Encapsulated RNA Immunogenic Composition Encoding the Influenza HA as a Vaccine Antigen The influenza modRNA immunogenic composition is based on a modRNA platform technology. The single-stranded, 5'-capped modRNA contains an open reading frame encoding the HA vaccine antigen and features structural elements optimized for high efficacy of the RNA. The modRNA also contains a substitution of 1-methyl-pseudouridine for each uridine to decrease recognition of the vaccine RNA by innate immune sensors, such as TLRs 7 and 8, resulting in decreased innate immune activation and increased protein translation. The modRNA is encapsulated in a LNP for delivery into target cells. The formulation contains 2 functional lipids, ALC-0315 and ALC-0159, and 2 structural lipids DSPC (1,2-distearoyl-sn-glycero-3-phosphocholine) and cholesterol. The physicochemical properties and the structures of the 4 lipids are shown in the Table below.

TABLE 10

Lipids in the Formulation

| Lipid | Molecular Weight [Da] | Molecular Formula | Physical State and Storage Condition | Chemical Name (Synonyms) and Structure |
|---|---|---|---|---|
| ALC-0315 | 766 | $C_{48}H_{95}NO_5$ | Liquid (oil) −20 °C | ((4-hydroxybutyl)azanediyl)bis(hexane-6,1-diyl)bis(2-hexyldecanoate) |

TABLE 10-continued

Lipids in the Formulation

| Lipid | Molecular Weight [Da] | Molecular Formula | Physical State and Storage Condition | Chemical Name (Synonyms) and Structure |
|---|---|---|---|---|
| | | | | 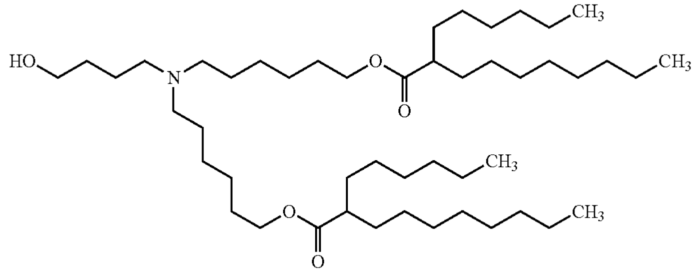 [SMILES: CCCCCCCCC(CCCCCC)C(=O)OCCCCCCN(CCCCO)CCCCCCOC(=O)C(CCCCCC)CCCCCCCC] |
| ALC-0159 | ~2400-2600 | $C_{30}H_{60}NO(C_2H_4O)_nOCH_3$ | Solid −20 °C | 2-[(polyethylene glycol)-2000]-N,N-ditetradecylacetamide 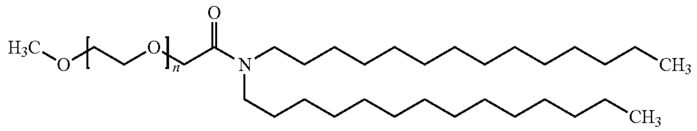 |
| DSPC | 790 | $C_{44}H_{88}NO_8P$ | Solid −20 °C | 1,2-Distearoyl-sn-glycero-3-phosphocholine 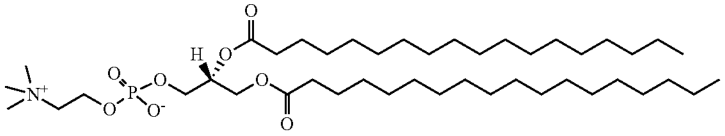 [SMILES: CCCCCCCCCCCCCCCCCC(=O)OC[C@H](COP(=O)([O-])OCC[N+](C)(C)C)OC(=O)CCCCCCCCCCCCCCCCC] |
| Cholesterol | 387 | $C_{27}H_{46}O$ | Solid −20 °C | 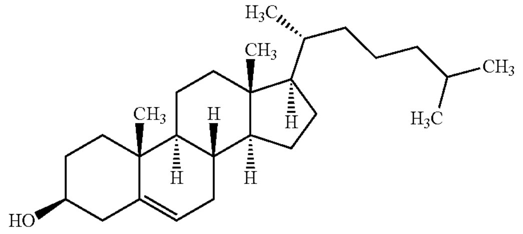 |

Influenza modRNA vaccine candidates selected for initial clinical testing will contain the full-length, codon-optimized coding sequence for the HA glycoprotein from the 4 cell-based virus strains recommended for use in the 2021-2022 Northern Hemisphere influenza season.

A/Wisconsin/588/2019 (H1N1)

A/Cambodia/e0826360/2020 (H3N2)

B/Phuket/3073/2013 (B Yamagata)

B/Washington/02/2019 (B Victoria)

In another embodiment, PF-07252220 (IRV) vaccine for Suspension for Injection is supplied as a white to off-white sterile frozen liquid, packaged in a 2 mL clear glass vial with a rubber stopper, aluminum overseal and flip off cap. The solution is a white to off-white opalescent liquid which may contain white to off white opaque, amorphous particles. The vial contains 0.5 mL with an extractable volume of 0.3 mL for further dilution via syringe mixing. For in-vial dilution, the vial contents (0.5 mL) should be accounted for the final dosing solution. Each vial includes the 0.1 mg/mL of PF-07252220 in a Lipid Nanoparticle (LNP) construct in 300 mM sucrose and 10 mM Tris, pH 7.4. There is no microbiological growth inhibitor in the formulation. PF-07252220 consists of five variations; four monovalent strain presentations and a quadrivalent strain presentation. The monovalent presentations may be further mixed to bivalent and quadrivalent dosing solutions at the point of use. The stability data presented below applies to all presentations and mixtures.

PF-07836259 (Phuket) Influenza mod RNA Suspension for Injection, 0.1 mg/mL

PF-07829855 (Wisconsin) Influenza mod RNA Suspension for Injection, 0.1 mg/mL

PF-07836261 (Washington) Influenza mod RNA Suspension for Injection, 0.1 mg/ml

PF-07836258 (Cambodia) Influenza mod RNA Suspension for Injection, 0.1 mg/ml

PF-07841697 Quadrivalent Influenza mod RNA Suspension for Injection, 0.1 mg/mL

The active investigational product must be stored at −90 to −60° C. (−130 to −76° F.) prior to use. Vials should be thawed at room temperature (no more than 30° C./ 86° F.) for approximately 30 minutes and then mixed by gently inverting the vial(s) 10 times. The investigational product will be administered intramuscularly.

TABLE 11

MONOVALENT DOSE PREPARATIONS USING 0.5 ML FILLED VOLUME VIALS OF MONOVALENT INFLUENZA MOD RNA VACCINE

| Dose | Dilution Type | Volume of PF-07252220 | Volume of 0.9% Sodium Chloride | Final Volume of Dosing solution | Final Dosing Solution concentration (in Diluted Syringe/Vial) | Final Injection Volume | Max number of Doses per DP vial |
|---|---|---|---|---|---|---|---|
| 3.75 mcg | Syringe to | 0.3 mL | 2.1 mL | 2.4 mL | 12.5 mcg/mL | 0.3 mL | 5 |
| 7.5 | In-Vial | 0.5 mL | 1.5 mL | 2 mL | 25 mcg/mL | 0.3 mL | 4 |
| 15 | In-Vial | 0.5 mL | 0.5 mL | 1 mL | 50 mcg/mL | 0.3 mL | 2 |
| 30 | None | 0.5 mL | 0 mL | 0.5 mL | 100 mcg/mL | 0.3 mL | 1 |

*Dilutions of Influenza mod RNA PF-07252220 are not limited to the preparations described in this table. The preparation instructions provided in this document are intended to support a specific clinical design, however dose preparation is not limited to these specific instruction sets. Active doses in the verified concentration range are acceptable.

TABLE 12

BIVALENT DOSE PREPARATIONS USING 0.5 ML FILLED VOLUME VIALS OF MONOVALENT INFLUENZA MOD RNA VACCINE AND SYRINGE TO SYRINGE MIX

| Strain: Dose (mcg) | DP Vial Strain | Volume of PF-07252220 in Vial | Volume of 0.9% Sodium Chloride into Vial | Syringe to Syringe Mix (1:1) | Final Volume of Dosing Solution in Diluted | Final Dosing solution Concentration (total active content) | Final Injection Volume |
|---|---|---|---|---|---|---|---|
| 1:7.5 mcg | 1 | 0.5 mL × | 0.5 mL | 0.3 mL | 0.6 mL | 50 mcg/mL | 0.3 mL |
| 2:7.5 mcg | 2 | 0.5 mL × 1 vial | 0.5 mL | 0.3 mL | | | |
| 1:15 mcg | 1 | 0.5 mL × | 0 | 0.3 mL | 0.6 mL | 100 mcg/mL | 0.3 mL |
| 2:15 mcg | 2 | 0.5 mL × 1 vial | 0 | 0.3 mL | | | |
| 1:30 mcg<br>2:30 mcg | 1 | 0.5 mL × 2 vials | 0 | 0.5 mL | 1 mL | 100 mcg/mL | 0.6 mL |
| | 2 | 0.5 mL × 2 vials | 0 | 0.5 mL | | | |

*Bivalent doses can be made of any 2 monovalent strains, designated as Strain 1 and Strain 2

TABLE 13

BIVALENT DOSE PREPARATIONS USING 0.5 ML FILLED VOLUME VIALS OF MONOVALENT INFLUENZA MOD RNA VACCINE AND IN-VIAL MIX (VOLUME OF VIAL STRAIN 1 TRANSFERRED TO VIAL STRAIN 2)

| Strain: Dose (mcg) | DP Vial Strain | Volume of PF-07252220 in Vial | Volume of 0.9% Sodium Chloride into Vial | In-Vial Mix: Volume of Vial Strain 1 transferred to Vial Strain 2 | Final Volume of Dosing Solution in Diluted Vial | Final Dosing solution Concentration (total active content) | Final Injection Volume |
|---|---|---|---|---|---|---|---|
| 1:7.5 mcg | 1 | 0.5 mL | 0.5 mL | 0.5 mL | 1 mL in | 75 mcg/mL | 0.3 mL |
| 2:15 mcg | 2 | 0.5 mL | 0 | N/A | Vial 2 | | |
| 1:3.75 mcg | 1 | 0.5 mL | 1.5 mL | 0.5 mL | 1 mL in | 62.5 mcg/mL | 0.3 mL |
| 2:15 mcg | 2 | 0.5 mL | 0 | N/A | Vial 2 | | |

*Bivalent doses can be made of any 2 monovalent strains, designated as Strain 1 and Strain 2

TABLE 14

QUADRIVALENT DOSE PREPARATIONS USING 100 MCG/ML QUADRIVALENT INFLUENZA MOD RNA VACCINE

| Dose | Dilution Type | Volume of PF-0725222 | Volume of 0.9% Sodium | Final Dosing Solution concentratio | Injection Volum | Max number of |
|---|---|---|---|---|---|---|
| 7.5 mcg per strain | None | 0.5 mL | N/A | 100 mcg/mL | 0.3 mL | 1 |
| 15 mcg per strain | None | 0.5 mL × 2 vials | N/A | 100 mcg/mL | 0.6 mL | 1 |

TABLE 15

QUADRIVALENT DOSE PREPARATIONS USING 0.5 ML FILLED VOLUME VIALS OF MONOVALENT INFLUENZA MOD RNA VACCINE AND SYRINGE TO SYRINGE MIX

| Strain: Dose (mcg) | DP Vial Strain | Volume of PF-07252220 in Vial | Step 1: Volume from Vial for syringe to syringe mix | Volume of 0.9% Sodium Chloride | Step 2: Volume from Step 1 for syringe to syringe mix | Final Dosing solution Concentration (total active content) | Final Injection Volume |
|---|---|---|---|---|---|---|---|
| 1:7.5 mcg | 1 | 0.5 mL | 0.3 mL | 1.6 mL | 1.1 mL | 60 mcg/mL | 1 mL |
| 2:7.5 mcg | 2 | 0.5 mL | 0.3 mL | | from | | |
| 3:22.5 | | | | | syringe A | | |
| 4:22.5 | 3 | 0.5 mL × 2 vials | 0.6 mL | N/A | 0.9 mL from | | |
| | 4 | 0.5 mL × 2 vials | 0.6 mL | | syringe B | | |
| 1:7.5 mcg | 1 | 0.5 mL | 0.3 mL | 0.4 mL | 0.3 mL | 90 mcg/mL | 1 mL |
| 2:7.5 mcg | 2 | 0.5 mL | 0.3 mL | | from | | |
| 3:37.5 | | | | | syringe A | | |
| 4:37.5 | 3 | 0.5 mL × 2 vials | 0.6 mL | N/A | 0.9 mL from | | |
| | 4 | 0.5 mL × 2 vials | 0.6 mL | | syringe B | | |

*Quadrivalent doses can be made of any 4 monovalent strains, designated as Strain 1, 2, 3, and 4

Example 4: Nonclinical Studies

An initial mouse immunogenicity study was conducted using an influenza modRNA immunogenic composition encoding the HA sequence from A/California/07/2009 (H1N1). This HA sequence differs from the H1N1 HA antigen that will be used in the clinical study due to strain differences, but the modRNA was formulated with the same clinical LNP composition and provides supportive data for the platform.

BALB/c mice were immunized IM with 1 μg of the LNP-formulated influenza modRNA vaccine on Days 0 and 28. ELISA of sera obtained on Days 28 and 49 showed high levels of HA-binding IgG. Sera obtained as early as 14 days after the first dose had high neutralization titers against A/California/07/2009 influenza virus, and by Day 49 (21 days after the second dose) serum influenza neutralization titers exceeded 1×104. The HAI titers against A/California/07/2009 measured in sera drawn on Day 49 greatly exceeded the titer of 40 that is generally accepted as protective against influenza in humans. BALB/c mice were immunized twice IM with 1 μg of the vaccine candidate. HA-specific IgG was measured by ELISA. The functionality of the antibodies was measured by influenza virus microneutralization. IFNy ELISpot using splenocytes harvested on Day 49 and stimulated with antigen-specific peptides showed strong CD4+ and CD8+ T-cell responses. These data confirmed that modRNA formulated with LNPs elicited Th1 phenotype T-cell responses. BALB/c mice received 2 IM immunizations with 1 μg of modRNA encoding influenza HA. The T-cell response was analyzed using antigen-specific peptides to stimulate T cells recovered from the spleen. IFNy release was measured after peptide stimulation using an ELISpot assay.

The primary serological assay used to measure vaccine-induced immune responses to influenza is the hemagglutinin inhibition assay, or HAI. The HAI quantitatively measures functional antibodies in serum that prevent HA-mediated agglutination of red blood cells in reactions containing receptor-destroying enzyme pretreated serum samples, influenza virus and red blood cells derived from turkey or guinea pig. The HAI titer is the reciprocal of the highest serum dilution resulting in loss of HA activity, visualized as a teardrop shape when the microtiter plate is tilted. Titers from multiple determinations per sample are reported as geometric mean titers (GMT). A HAI titer of ≥1:40 is generally accepted as protective in humans. HAI assays have been developed for each of the 4 influenza strains, A/Wisconsin/588/2019 (H1N1), A/Cambodia/e0826360/2020 (H3N2), B/Phuket/3073/2013 (B Yamagata) and B/Washington/02/2019 (B Victoria).

The influenza virus microneutralization assay, or MNT, quantitatively measures functional antibodies in serum that neutralize influenza virus activity, preventing productive infection of a host cell monolayer. A neutralization reaction occurs when influenza virus is incubated with serum samples; this reaction mixture is then applied to a monolayer of Madin-Darby Canine Kidney (MDCK) cells to measure the extent of neutralization. MNT titers are reported as the reciprocal of the dilution that results in 50% reduction in infection when compared to a no serum control.

Study to Evaluate the Feasibility of Bi-Valent modRNA HA Flu Vaccine with Pre-Mixed Drug Substance (RNA) to Form an LNP and Post-Mixed LNP Arms As used herein unless stated otherwise, a “pre-mixed” drug substance refers to a composition wherein RNA expressing either HA or NA is mixed in a desired ratio, followed by a single formulation into an LNP. A “post-mixed” drug product refers to a composition wherein each RNA expressing either HA or NA is encapsulated in an LNP and the resulting RNA-encapsulated LNPs are then mixed in a desired ratio.

Hemagglutination-inhibition (HAI) antibody titers were examined in mice administered with a formulation as described in the following table.

Study Design Table:

TABLE 16

| Gp# | Mice | RNA drug product (DP, i.e., RNA encapsulated LNP) Description | Dose (μg) | Dose Vol/ Route | Vax (Day) | Bleed (Day) |
|---|---|---|---|---|---|---|
| 1 | 10 | Saline | — | 50 μl/IM | 0, 28 | 21, 42 |
| 2 | 10 | LNP modRNA HA mono-valent-Wisc Strain 10 mM Tris and 300 mM Sucrose | 1 | 50 μl/IM | 0, 28 | 21, 42 |
| 3 | 10 | LNP modRNA HA mono-valent-Wisc Strain 10 mM Tris and 300 mM Sucrose | 0.2 | 50 μl/IM | 0, 28 | 21, 42 |
| 4 | 10 | LNP modRNA HA mono-valent-Phuket Strain 10 mM Tris and 300 mM Sucrose | 1 | 50 μl/IM | 0, 28 | 21, 42 |
| 5 | 10 | LNP modRNA HA mono-valent-Phuket Strain 10 mM Tris and 300 mM Sucrose | 0.2 | 50 μl/IM | 0, 28 | 21, 42 |
| 6 | 10 | LNP modRNA HA pre-mix bi-valent, i.e., Bivalent Wisconsin and Phuket (DS mixed prior to LNP formation) 10 mM Tris and 300 mM Sucrose | 2 | 50 μl/IM | 0, 28 | 21, 42 |
| 7 | 10 | LNP modRNA HA pre-mix bi-valent, i.e., Bivalent Wisconsin and Phuket (DS mixed prior to LNP formation) 10 mM Tris and 300 mM Sucrose | 0.4 | 50 μl/IM | 0, 28 | 21 ,42 |
| 8 | 10 | LNP modRNA HA post-mix bi-valent, i.e., Bivalent Wisconsin and Phuket (LNP mix) 10 mM Tris and 300 mM Sucrose | 2 | 50 μl/IM | 0, 28 | 21, 42 |
| 9 | 10 | LNP modRNA HA post-mix bi-valent, i.e., Bivalent Wisconsin and Phuket (LNP mix) 10 mM Tris and 300 mM Sucrose | 0.4 | 50 μl/IM | 0, 28 | 21, 42 |

High HAI Titers were induced by Wisconsin HA modRNA at 3 wks post-dose 1.

Slightly Higher HAI in Bi-Valent Groups.

Higher HAI in pre-mix Formulation for Bi-valent at 0.2 ug Dose. See tables 17-18 below.

TABLE 17

| GMTs 3 weeks post-dose 1 (Wisconsin) | | | | | |
|---|---|---|---|---|---|
| | GMT: | | | | |
| | 10 | 422 | 260 | 453 | 130 |
| Sample: | Saline (Group 1) | bi-val. pre-mix. | bi-val. pre-mix. | bi-val. post-mix. | bi-val. post-mix. |
| RNA Dose (ug) | — | 2 | 0.4 | 2 | 0.4 |

TABLE 18

| GMTs 3 weeks post-dose 1 (Phuket) | | | | | |
|---|---|---|---|---|---|
| | GMT: | | | | |
| | 10 | 25 | 13 | 28 | 10 |
| Sample: | Saline (Group 1) | bi-val. pre-mix. | bi-val. pre-mix. | bi-val. post-mix. | bi-val. post-mix. |
| RNA Dose (ug) | — | 2 | 0.4 | 2 | 0.4 |

It was also observed that 50% Neutralizing Ab Titers Were Comparable Between Pre-Mix and Post-Mix Drug Product. See Tables 19-22 below.

TABLE 19

| at 3 weeks post-dose 1 (against Wisconsin) | | | | | |
|---|---|---|---|---|---|
| | GMT | | | | |
| | 165 | 14319 | 9393 | 24043 | 5221 |
| Sample: | Saline | bi-val. pre-mix. | bi-val. pre-mix. | bi-val. post-mix. | bi-val. post-mix. |
| RNA Dose (ug) | — | 2 | 0.4 | 2 | 0.4 |

TABLE 20

| at 2 weeks post-dose 2 (against Wisconsin) | | | | | |
|---|---|---|---|---|---|
| | GMT | | | | |
| | 169 | 1286052 | 290731 | 1187870 | 278031 |
| Sample: | Saline | bi-val. pre-mix. | bi-val. pre-mix. | bi-val. post-mix. | bi-val. post-mix. |
| RNA Dose (ug) | — | 2 | 0.4 | 2 | 0.4 |

TABLE 21

| at 3 weeks post-dose 1 (against Phuket) | | | | | |
|---|---|---|---|---|---|
| | GMT | | | | |
| | 60 | 730 | 1051 | 1089 | 265 |
| Sample: | Saline | bi-val. pre-mix. | bi-val. pre-mix. | bi-val. post-mix. | bi-val. post-mix. |
| RNA Dose (ug) | — | 2 | 0.4 | 2 | 0.4 |

TABLE 22

| at 2 weeks post-dose 2 (against Phuket) | | | | | |
|---|---|---|---|---|---|
| | GMT | | | | |
| | 103 | 31818 | 6800 | 29035 | 8186 |
| Sample: | Saline | bi-val. pre-mix. | bi-val. pre-mix. | bi-val. post-mix. | bi-val. post-mix. |
| RNA Dose (ug) | — | 2 | 0.4 | 2 | 0.4 |

HAI Titers Were Comparable Between Pre-Mix Versus Post-Mix Drug Product. See tables 23-26 below.

TABLE 23

| at 3 weeks post-dose 1 (against Wisconsin) | | | | | |
|---|---|---|---|---|---|
| | GMT | | | | |
| | 10 | 422 | 260 | 453 | 130 |
| Sample: | Saline | bi-val. pre-mix. | bi-val. pre-mix. | bi-val. post-mix. | bi-val. post-mix. |
| RNA Dose (ug) | — | 2 | 0.4 | 2 | 0.4 |

TABLE 24

| at 2 weeks post-dose 2 (against Wisconsin) | | | | | |
|---|---|---|---|---|---|
| | GMT | | | | |
| | 10 | 2986 | 2389 | 3152 | 2229 |
| Sample: | Saline | bi-val. pre-mix. | bi-val. pre-mix. | bi-val. post-mix. | bi-val. post-mix. |
| RNA Dose (ug) | — | 2 | 0.4 | 2 | 0.4 |

TABLE 25

| at 3 weeks post-dose 1 (against Phuket) | | | | | |
|---|---|---|---|---|---|
| | GMT | | | | |
| | 10 | 25 | 13 | 28 | 10 |
| Sample: | Saline | bi-val. pre-mix. | bi-val. pre-mix. | bi-val. post-mix. | bi-val. post-mix. |
| RNA Dose (ug) | — | 2 | 0.4 | 2 | 0.4 |

TABLE 26

| at 2 weeks post-dose 2 (against Phuket) | | | | | |
|---|---|---|---|---|---|
| | GMT | | | | |
| | 10 | 1040 | 243 | 844 | 184 |
| Sample: | Saline | bi-val. pre-mix. | bi-val. pre-mix. | bi-val. post-mix. | bi-val. post-mix. |
| RNA Dose (ug) | — | 2 | 0.4 | 2 | 0.4 |

Example 5: Description of Quadrivalent Drug Product

The quadrivalent drug product is a preservative-free, sterile dispersion of liquid nanoparticles (LNP) in aqueous cryoprotectant buffer for intramuscular administration. The drug product is formulated at 0.1 mg/mL RNA in 10 mM Tris buffer, 300 mM sucrose, pH 7.4.

The drug product is supplied in a 2 mL glass vial sealed with a chlorobutyl rubber stopper and an aluminum seal with flip-off plastic cap (maximum nominal volume of 0.3 mL).

TABLE 27

Composition of Quadrivalent Drug Product

| Name of Ingredient | Grade/Quallty Standard | Function | Unit Formula (mg/mL) | Filled Amount (Total mg/vial) | Nominal Amount or Net Quantity (Net mg/vial) |
|---|---|---|---|---|---|
| PF-07829855 Drug Substance (Wisconsin) | In-house specification | Active ingredient | 0.025 | 0.013 | 0.008 |
| PF-07836258 Drug Substance (Cambodia) | In-house specification | Active ingredient | 0.025 | 0.013 | 0.008 |
| PF-07836259 Drug Substance (Phuket) | In-house specification | Active ingredient | 0.025 | 0.013 | 0.008 |
| PF-07836261 Drug Substance (Washington) | In-house specification | Active ingredient | 0.025 | 0.013 | 0.008 |

TABLE 27-continued

| Composition of Quadrivalent Drug Product | | | | | |
|---|---|---|---|---|---|
| Name of Ingredient | Grade/Quallty Standard | Function | Unit Formula (mg/mL) | Filled Amount (Total mg/vial) | Nominal Amount or Net Quantity (Net mg/vial) |
| ALC-0315[a] | In-house specification | Functional lipid | 1.43 | 0.72 | 0.43 |
| ALC-0159[b] | In-house specification | Functional lipid | 0.18 | 0.09 | 0.05 |
| DSPC[c] | In-house specification | Structural lipid | 0.31 | 0.16 | 0.09 |
| Cholesterol | Ph. Eur., NF | Structural lipid | 0.62 | 0.31 | 0.2 |
| Sucrose | Ph. Eur., NF | Cryoprotectant | 102.69 | 51.35 | 30.81 |
| Tromethamine (Tris base) | Ph. Eur., USP | Buffer component | 0.20 | 0.10 | 0.06 |
| Tris (hydroxymethyl) aminomethane hydrochloride (Tris HCl) | In-house specification | Buffer component | 1.32 | 0.66 | 0.40 |
| Water for Injection | Ph. Eur., USP, JP | Solvent | q.s.[d] to 1.00 mL | q.s.[d] to 0.50 mL | q.s.[d] to 0.30 mL |

[a]ALC-0315 = ((4-hydroxybutyl)azanediyl)bis(hexane-6,1-diyl)bis(2-hexyldecanoate)
[b]ALC-0159 = 2-[(polyethylene glycol)-2000]-N,N-ditetradecylacetamide
[c]DSPC = 1,2-Distearoyl-sn-glycero-3-phosphocholine
[d]q.s. is an abbreviation for quantum satis meaning as much as is sufficient.

The recommended storage temperature of the FIH drug substance is −20±5° C.

The recommended long term storage temperature of the FIH drug product is −60 to −90° C.

The drug product may be stored at 2-8° C. at Point of Use.

TABLE 28

| Batch Analyses for Quadrivalent Clinical Drug Product | | |
|---|---|---|
| Analytical Procedure | Quality Attributes | Acceptance Criteria |
| Composition and Strength | | |
| Appearance (Visual) | Appearance | White to off-white suspension |
| Appearance (Particles) | Appearance (Visible Particulates) | May contain white to off-white opaque, amorphous particles |
| Subvisible particulate matter | Subvisible particles | Particles ≥10 μm: ≤6000 per container<br>Particles ≥25 μm: ≤600 per container |
| Potentiometry | pH | 7.4 ± 0.5 |
| Osmometry | Osmolality | 240-400 mOsmol/kg |
| Dynamic Light Scattering (DLS) | LNP Size | 40-120 nm |
| | LNP Polydispersity | ≤0.3 |
| Fluorescence Assay | RNA Content | 0.074-0.126 mg/mL |
| | RNA Encapsulation | ≥80% |
| HPLC-CAD | ALC-0315 Content | 0.90-1.85 mg/mL |
| | ALC-0159 Content | 0.11-0.24 mg/mL |
| | DSPC Content | 0.18-0.41 mg/mL |
| | Cholesterol Content | 0.36-0.78 mg/mL |
| Container content | Vial content (volume) | Not less than 0.30 mL |
| Identity | | |
| HPLC-CAD | Lipid identities | Retention times consistent with references (ALC-0315, ALC-0159, Cholesterol, DSPC) |
| RT-PCR | Identity of encoded RNA sequence(s) | Identity confirmed |
| Purity | | |
| Capillary Gel Electrophoresis | RNA Integrity | ≥55% intact RNA (release)<br>≥50% intact RNA (stability) |

TABLE 28-continued

| Batch Analyses for Quadrivalent Clinical Drug Product | | |
|---|---|---|
| Analytical Procedure | Quality Attributes | Acceptance Criteria |
| Safety | | |
| Endotoxin (LAL) | Endotoxin (LAL) | ≤12.5 EU/mL |
| Sterility | Sterility | No growth detected |
| Dye incursion | Container Closure Integrity | Pass |

TABLE 29

| Batch Analyses for Quadrivalent Clinical Drug Product | | |
|---|---|---|
| Analytical Procedure | Quality Attributes | Acceptance Criteria |
| Composition and Strength | | |
| Appearance (Visual) | Appearance | White to off-white suspension |
| Appearance (Particles) | Appearance (Visible Particulates) | May contain white to off-white opaque, amorphous particles |
| Subvisible particulate matter | Subvisible particles | Particles ≥10 μm: ≤6000 per container<br>Particles ≥25 μm: ≤600 per container |
| Potentiometry | pH | 7.4 ± 0.5 |
| Osmometry | Osmolality | 240-400 mOsmol/kg |
| Dynamic Light Scattering (DLS) | LNP Size | 40-120 nm |
| | LNP Polydispersity | ≤0.3 |
| Fluorescence Assay | RNA Content | 0.074-0.126 mg/mL |
| | RNA Encapsulation | ≥80% |
| HPLC-CAD | ALC-0315 Content | 0.90-1.85 mg/mL |
| | ALC-0159 Content | 0.11-0.24 mg/mL |
| | DSPC Content | 0.18-0.41 mg/mL |
| | Cholesterol Content | 0.36-0.78 mg/mL |
| Container content | Vial content (volume) | Not less than 0.30 mL |
| Identity | | |
| HPLC-CAD | Lipid identities | Retention times consistent with references (ALC-0315, ALC-0159, Cholesterol, DSPC) |
| RT-PCR | Identity of encoded RNA sequence(s) | Identity confirmed |
| Purity | | |
| Capillary Gel Electrophoresis | RNA Integrity | ≥55% intact RNA (release)<br>≥50% intact RNA (stability) |
| Safety | | |
| Endotoxin (LAL) | Endotoxin (LAL) | ≤12.5 EU/mL |
| Sterility | Sterility | No growth detected |
| Dye incursion | Container Closure Integrity | Pass |

Example 6: LNP Flu HA modRNA Quadrivalent Study

The following example describes a study of LNP Flu HA modRNA Quadrivalent, in which mice were administered with different LNP_Flu HA modRNA materials as detailed in the table below. Sera collected at Day 21 post prime and at Day 42 (14 days post boost) were evaluated by serology testing (HAI, and neutralization).

TABLE 30

| Mice | RNA DP Description | Dose (μg) | Dose Vol/Route | Vax (Day) | Bleed (Day) |
|---|---|---|---|---|---|
| 10 | Saline | — | 50 μl/IM | 0, 28 | 21, 42 |
| 10 | Quadrivalent (modRNAs premixed & coformulate) | 4 | 50 μl/IM | 0, 28 | 21, 42 |

TABLE 30-continued

| Mice | RNA DP Description | Dose (μg) | Dose Vol/Route | Vax (Day) | Bleed (Day) |
|---|---|---|---|---|---|
| 10 | Quadrivalent (modRNAs premixed & coformulate) | 0.8 | 50 μl/IM | 0, 28 | 21, 42 |
| 10 | Quadrivalent (LNPs made separately & mixed), "post-mixed" | 4 (1 ug each) | 50 μl/IM | 0, 28 | 21, 42 |
| 10 | Quadrivalent (LNPs made separately & mixed) "post-mixed" | 0.8 (0.2 ug each) | 50 μl/IM | 0, 28 | 21, 42 |

HAI Titers were Comparable Between Pre-mixed Versus Post-mixed Drug Product at D21, see following tables 31-35.

TABLE 31

| GMTs 3 weeks post-dose 1 (Wisconsin) | | | | | |
|---|---|---|---|---|---|
| GMT: | 10 | 686 | 343 | 485 | 299 |
| Sample: | Saline (Group 1) | Pre-mixed | Pre-mixed | Post-mixed | Post-mixed |
| RNA Dose (ug) | — | 4 | 0.8 | 4 | 0.8 |

TABLE 32

| GMTs 3 weeks post-dose 1 (Cambodia) | | | | | |
|---|---|---|---|---|---|
| | GMT: | | | | |
| | 10 | 686 | 343 | 485 | 299 |
| Sample: | Saline (Group 1) | Pre-mixed | Pre-mixed | Post-mixed | Post-mixed |
| RNA Dose (ug) | — | 4 | 0.8 | 4 | 0.8 |

TABLE 33

| GMTs 3 weeks post-dose 1 (Cambodia) | | | | | |
|---|---|---|---|---|---|
| | GMT: | | | | |
| | 28 | 40 | 49 | 46 | 53 |
| Sample: | Saline (Group 1) | Pre-mixed | Pre-mixed | Post-mixed | Post-mixed |
| RNA Dose (ug) | — | 4 | 0.8 | 4 | 0.8 |

TABLE 34

| GMTs 3 weeks post-dose 1 (Washington) | | | | | |
|---|---|---|---|---|---|
| | GMT: | | | | |
| | 14 | 26 | 21 | 30 | 23 |
| Sample: | Saline (Group 1) | Pre-mixed | Pre-mixed | Post-mixed | Post-mixed |
| RNA Dose (ug) | — | 4 | 0.8 | 4 | 0.8 |

TABLE 35

| GMTs 3 weeks post-dose 1 (Phuket) | | | | | |
|---|---|---|---|---|---|
| | GMT: | | | | |
| | 10 | 61 | 36 | — | 53 |
| Sample: | Saline (Group 1) | Pre-mixed | Pre-mixed | Post-mixed | Post-mixed |
| RNA Dose (ug) | — | 4 | 0.8 | 4 | 0.8 |

H1N1 A/Wisconsin: Comparable 50% Neutralization Titers Between Pre-mix and Post-Mix were observed. H3N2 A/Cambodia: Comparable 50% Neutralization Titers Between Pre-mix and Post-Mix were observed. By/Phuket: Comparable 50% Neutralization Titers Between Pre-mix and Post-Mix were observed. By/Washington: Comparable 50% Neutralization Titers Between Pre-mix and Post-Mix were also observed.

EXAMPLE 7 : Immunogenicity Data in Mice of a Multivalent Influenza modRNA Vaccine, cont'd To evaluate the feasibility of a multivalent formulation of the modRNA influenza vaccine, modRNAs encoding 4 different HA proteins and 4 different neuraminidase (NA) proteins were generated. Immune responses elicited by mice vaccinated with LNP-formulated modRNA encoding a single strain-specific HA or NA were compared to groups vaccinated with an octavalent HA/NA modRNA formulation. Octavalent formulation methods were compared by separately formulating each modRNA expressing HA or NA in LNPs and then mixing the eight LNPs together in equal ratios, or by pre-mixing the eight modRNAs followed by a single co-formulation in LNPs.

BALB/c mice were immunized IM with 2 μg of each HA and NA-expressing modRNA either as a monovalent or octavalent vaccine formulation in LNPs on Days 0 and 28. Robust antibody and T cell responses were elicited by LNP-formulated modRNA to all HA and NA components, at levels similar to or greater than the licensed vaccine comparator. Similar HAI and neutralizing responses were observed on Day 49 (21 days after the second boost) for individual HA and octavalent formulations for influenza A strains. Antibodies measured against NA showed a similar trend as HA (data not shown). Immunogenicity studies in mice, benchmarked against a licensed, adjuvanted inactivated influenza vaccine, support the potential use of a multivalent influenza modRNA vaccine formulation to target at least four different influenza virus strains. Initial immunogenicity studies in mice of an octavalent HA/NA modRNA vaccine indicated no interference for influenza A strains and exhibited antibody responses for influenza B strains in comparison to monovalent control vaccines. These initial mouse immunogenicity data support the use of a multivalent modRNA formulation.

CLAUSES

1. An influenza virus vaccine, comprising: at least one ribonucleic acid (RNA) polynucleotide having an open reading frame encoding at least one influenza virus antigenic polypeptide or an immunogenic fragment thereof, formulated in a lipid nanoparticle.
2. The influenza vaccine of clause 1, wherein the RNA further comprises a 5' cap analog.
3. The influenza vaccine of clause 2, wherein the 5' cap analog comprises $m_2^{7,3'-O}Gppp(m_1^{2'-O})$ ApG.
4. The influenza vaccine of clause 1, wherein the RNA further comprises a modified nucleotide.
5. The influenza vaccine of clause 4, wherein the modified nucleotide comprises N1-Methylpseudourodine-5'-triphosphate (m1ΨTP).
6. The influenza vaccine of clause 1, wherein the at least one antigenic polypeptide is influenza hemagglutinin 1 (HA1), hemagglutinin 2 (HA2), an immunogenic fragment of HA1 or HA2, or a combination of any two or more of the foregoing.
7. The influenza vaccine of clause 1, wherein at least one antigenic polypeptide is HA1, HA2, or a combination of HA1 and HA2, and at least one antigenic polypeptide is selected from the group consisting of neuraminidase (NA), nucleoprotein (NP), matrix protein 1 (M1), matrix protein 2 (M2), non-structural protein 1 (NS1) and non-structural protein 2 (NS2).
8. The influenza vaccine of clause 1, wherein at least one antigenic polypeptide is HA1, HA2, or a combination of HA1 and HA2, and at least one antigenic polypeptide is neuraminidase (NA).
9. The influenza vaccine of clause 1, wherein the composition comprises a) at least one ribonucleic acid (RNA) polynucleotide having an open reading frame encoding influenza hemagglutinin 1 (HA1); b) at least one ribonucleic acid (RNA) polynucleotide having an open reading frame encoding hemagglutinin 2 (HA2); c) at least one ribonucleic acid (RNA) polynucleotide having an open reading frame encoding at least one antigenic polypeptide is selected from the group consisting of neuraminidase (NA), nucleoprotein (NP), matrix protein 1 (M1), matrix protein 2 (M2), non-structural protein 1 (NS1) and non-structural protein 2 (NS2); and d) at least one ribonucleic acid (RNA) polynucleotide having an open reading frame encoding at least one antigenic polypeptide is selected from the group consisting of neuraminidase (NA), nucleoprotein (NP), matrix protein 1 (M1), matrix protein 2 (M2), non-structural protein 1 (NS1) and non-structural protein 2 (NS2).
10. The influenza vaccine according to clause 5, wherein the open reading frame is codon-optimized.
11. The influenza vaccine of clause 1, wherein the composition further comprises a cationic lipid.
12. The influenza vaccine of clause 1, wherein the composition comprises a lipid nanoparticle encompassing the mRNA molecule.
13. The influenza vaccine of clause 1, wherein the composition comprises a) a lipid nanoparticle encompassing at least one ribonucleic acid (RNA) polynucleotide having an open reading frame encoding influenza hemagglutinin 1 (HA1); b) a lipid nanoparticle encompassing at least one ribonucleic acid (RNA) polynucleotide having an open reading frame encoding hemagglutinin 2 (HA2); c) a lipid nanoparticle encompassing at least one ribonucleic acid (RNA) polynucleotide having an open reading frame encoding at least one antigenic polypeptide is selected from the group consisting of neuraminidase (NA), nucleoprotein (NP), matrix protein 1 (M1), matrix protein 2 (M2), non-structural protein 1 (NS1) and non-structural protein 2 (NS2); and d) a lipid nanoparticle encompassing at least one ribonucleic acid (RNA) polynucleotide having an open reading frame encoding at least one antigenic polypeptide is selected from the group consisting of neuraminidase (NA), nucleoprotein (NP), matrix protein 1 (M1), matrix protein 2 (M2), non-structural protein 1 (NS1) and non-structural protein 2 (NS2).
14. The influenza vaccine of clause 13, wherein the lipid nanoparticle size is at least 40 nm.
15. The influenza vaccine of clause 13, wherein the lipid nanoparticle size is at most 180 nm.
16. The influenza vaccine of clause 13, wherein at least 80% of the total RNA in the composition is encapsulated.
17. The influenza vaccine of clause 1, wherein the composition comprises
18. The influenza vaccine of clause 1, wherein the composition comprises ALC-0315 (4-hydroxybutyl) azanediyl)bis(hexane-6,1-diyl)bis(2-hexyldecanoate).
19. The influenza vaccine of clause 1, wherein the composition comprises ALC-0159 (2-[(polyethylene glycol)-2000]-N,N-ditetradecylacetamide).
20. The influenza vaccine of clause 1, wherein the composition comprises 1,2- Distearoyl-sn-glycero-3-phosphocholine (DSPC).
21. The influenza vaccine of clause 1, wherein the composition comprises cholesterol.
22. The influenza vaccine of clause 1, wherein the composition comprises 0.9-1.85 mg/mL ALC-0315; 0.11-0.24 mg/mL ALC-0159; 0.18 -0.41 mg/mL DSPC; and 0.36-0.78 mg/mL cholesterol.
23. The influenza vaccine of clause 1, wherein the composition comprises Tris.
24. The influenza vaccine of clause 1, wherein the composition comprises sucrose.
25. The influenza vaccine of clause 1, wherein the composition does not further comprise sodium chloride.
26. The influenza vaccine of clause 1, wherein the composition comprises 10 mM Tris.
27. The influenza vaccine of clause 1, wherein the composition comprises 300 mM sucrose.
28. The influenza vaccine of clause 1, wherein the composition has a pH 7.4.
29. The influenza vaccine of clause 1, wherein the composition has less than or equal to 12.5 EU/mL of bacterial endotoxins.
30. The influenza vaccine of clause 1, wherein the RNA polynucleotide comprises a 5' cap, 5' UTR, 3' UTR, histone stem-loop and poly-A tail.
31. The influenza vaccine of clause 30, wherein the 5' UTR comprises the sequence

```
                                        (SEQ ID No: 4)
AATAAACTAGTATTCTTCTGGTCCCCACAGACTCAGAGAGAA

CCC (5' WHO UTR1).
```

32. The influenza vaccine of clause 30, wherein the 5' UTR comprises the sequence (SEQ ID NO: 5)
GAGAAΨAAACΨAGΨAΨΨCΨΨ CΨGGΨCCCCA CAGACΨCAGA
GAGAACCCGCCACC 33. The influenza vaccine of clause 30, wherein the 5' UTR comprises the sequence (SEQ ID NO: 6)
AGAATAAACTAGTATTCTTCTGGTCCCCACAGACTCAGAGAGAA
CCC (5' WHO UTR1).

34. The influenza vaccine of clause 30, wherein the 3' UTR comprises the sequence (SEQ ID NO: 7)
CUCGAGCUGGUACUGCAUGCACGCAAUGCUAGCUGCCCCUUUCCCGUCCU
GGGUACCCCGAGUCUCCCCCGACCUCGGGUCCCAGGUAUGCUCCCACCUC
CACCUGCCCCACUCACCACCUCUGCUAGUUCCAGACACCUCCCAAGCACG
CAGCAAUGCAGCUCAAAACGCUUAGCCUAGCCACACCCCCACGGGAAACA
GCAGUGAUUAACCUUUAGCAAUAAACGAAAGUUUAACUAAGCUAUACUAA
CCCCAGGGUUGGUCAAUUUCGUGCCAGCCACACCCUGGAGCU
AGC (3' WHO UTR2).

35. The influenza vaccine of clause 30, wherein the 3' UTR comprises the sequence (SEQ ID NO: 8)
CΨCGAGCΨGGΨACΨGCAΨGCACGCAAΨGCΨAGCΨGCCCCΨΨΨCCCGΨCCΨ
GGGΨACCCCGAGΨCΨCCCCCGACCΨCGGGΨCCCAGGΨAΨGCΨCCCACCΨC
CACCΨGCCCCACΨCACCACCΨCΨGCΨAGΨΨCCAGACACCΨCCCAAGCACG
CAGCAAΨGCAGCΨCAAAACGCΨΨAGCCΨAGCCACACCCCCACGGGAAACA
GCAGΨGAΨΨAACCΨΨΨAGCAAΨAAACGAAAGΨΨΨAACΨAAGCΨAΨACΨAA
CCCCAGGGΨΨGGΨCAAΨΨΨCGΨGCCAGCCACACCCΨGGAGCΨA
GC (3' WHO ΨTR2).

36. An immunogenic composition comprising: (i) a first ribonucleic acid (RNA) polynucleotide having an open reading frame encoding a first antigen, said antigen comprising at least one influenza virus antigenic polypeptide or an immunogenic fragment thereof, and (ii) a second RNA polynucleotide having an open reading frame encoding a second antigen, said second antigen comprising at least one influenza virus antigenic polypeptide or an immunogenic fragment thereof, wherein the first and second RNA polynucleotides are formulated in a lipid nanoparticle (LNP).

37. The immunogenic composition of clause 36, wherein the first and second antigens comprise hemagglutinin (HA), or an immunogenic fragment or variant thereof.

38. The immunogenic composition of clause 36 or 37 wherein the first antigen comprises an HA from a different subtype of influenza virus to the influenza virus antigenic polypeptide or an immunogenic fragment thereof of the second antigen.

39. The immunogenic composition of any of clause 36-38, wherein the first and second RNA polynucleotides are formulated in a single lipid nanoparticle.

40. The immunogenic composition of any preceding clause further comprising: (iii) a third antigen comprising at least one influenza virus antigenic polypeptide or an immunogenic fragment thereof, wherein the third antigen is from influenza virus but is from a different strain of influenza virus to both the first and second antigens.

41. The immunogenic composition of clause 40, wherein the first, second and third RNA polynucleotides are formulated in a lipid nanoparticle.

42. The immunogenic composition of clause 41, wherein the first, second and third RNA polynucleotides are formulated in a single lipid nanoparticle.

43. The immunogenic composition of any preceding clause further comprising: (iv) a fourth RNA polynucleotide having an open reading frame encoding a fourth antigen, said antigen comprising at least one influenza virus antigenic polypeptide or an immunogenic fragment thereof, wherein the fourth antigen is from influenza virus but is from a different strain of influenza virus to the first, second and third antigens.

44. The immunogenic composition of clause 43, wherein the first, second, third, and fourth RNA polynucleotides are formulated in a lipid nanoparticle.

45. The immunogenic composition of clause 44, wherein the first, second, third, and fourth RNA polynucleotides are formulated in a single lipid nanoparticle.

46. The immunogenic composition of any preceding clause further comprising: (v) a fifth RNA polynucleotide having an open reading frame encoding a fifth antigen, said antigen comprising at least one influenza virus antigenic polypeptide or an immunogenic fragment thereof, wherein the fifth antigen is from influenza virus but is from a different strain of influenza virus to the first, second, third, and fourth antigens.

47. The immunogenic composition of clause 46, wherein the first, second, third, fourth, and fifth RNA polynucleotides are formulated in a lipid nanoparticle.

48. The immunogenic composition of clause 47, wherein the first, second, third, fourth, and fifth RNA polynucleotides are formulated in a single lipid nanoparticle.

49. The immunogenic composition of any preceding clause further comprising: (vi) a sixth RNA polynucleotide having an open reading frame encoding a sixth antigen, said antigen comprising at least one influenza virus antigenic polypeptide or an immunogenic fragment thereof, wherein the sixth antigen is from influenza virus but is from a different strain of influenza virus to the first, second, third, fourth, and fifth antigens.

50. The immunogenic composition of clause 49, wherein the first, second, third, fourth, and fifth RNA polynucleotides are formulated in a lipid nanoparticle.

51. The immunogenic composition of clause 50, wherein the first, second, third, fourth, and fifth RNA polynucleotides are formulated in a single lipid nanoparticle.

52. The immunogenic composition of any preceding clause further comprising: (vii) a seventh RNA polynucleotide having an open reading frame encoding a seventh antigen, said antigen comprising at least one influenza virus antigenic polypeptide or an immunogenic fragment thereof, wherein the seventh antigen is from influenza virus but is from a different strain of influenza virus to the first, second, third, fourth, fifth, and sixth antigens.

53. The immunogenic composition of clause 52, wherein the first, second, third, fourth, fifth, sixth and seventh RNA polynucleotides are formulated in a lipid nanoparticle.

54. The immunogenic composition of clause 53, wherein the first, second, third, fourth, fifth, sixth and seventh RNA polynucleotides are formulated in a single lipid nanoparticle.

55. The immunogenic composition of any preceding clause further comprising: (viii) an eighth RNA polynucleotide having an open reading frame encoding an eighth antigen, said antigen comprising at least one influenza virus antigenic polypeptide or an immunogenic fragment thereof, wherein the eighth antigen is from influenza virus but is from a different strain of influenza virus to the first, second, third, fourth, fifth, sixth and seventh antigens.

56. The immunogenic composition of clause 55, wherein the first, second, third, fourth, fifth, sixth, seventh and eighth RNA polynucleotides are formulated in a lipid nanoparticle.

57. The immunogenic composition of clause 56, wherein the first, second, third, fourth, fifth, sixth, seventh and eighth RNA polynucleotides are formulated in a single lipid nanoparticle.

58. The immunogenic composition of any preceding clause further comprising: (v) a fifth RNA polynucleotide having an open reading frame encoding a fifth antigen, said antigen comprising at least one influenza virus antigenic polypeptide or an immunogenic fragment thereof, wherein the fifth antigen is from influenza virus but is from a different strain of influenza virus to the first, second, third, and fourth antigens.

59. The immunogenic composition of clause 58, wherein the first, second, third, fourth, and fifth RNA polynucleotides are formulated in a lipid nanoparticle.

60. The immunogenic composition of clause 59, wherein the RNA polynucleotides are present in about equal ratios.

61. The immunogenic composition of any preceding clause, wherein each RNA polynucleotide comprises a modified nucleotide.

62. The immunogenic composition of clause 61, wherein the modified nucleotide is selected from the group consisting of pseudouridine, 1-methylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, and 2'—O-methyl uridine.

63. The immunogenic composition of any preceding clause, wherein each RNA polynucleotide comprises a 5' terminal cap, a 5' UTR, a 3'UTR, and a 3' polyadenylation tail.

64. The immunogenic composition of clause 63, wherein the 5' terminal cap comprises:

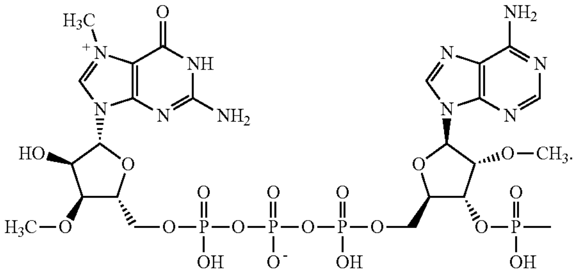

65. The immunogenic composition of clause 63, wherein the 5' UTR comprises SEQ ID NO: 1

66. The immunogenic composition of clause 63, wherein the 3' UTR comprises SEQ ID NO: 2.

67. The immunogenic composition of clause 63, wherein the 3' polyadenylation tail comprises SEQ ID NO: 3.

68. The immunogenic composition of any preceding clause, wherein the RNA polynucleotide has an integrity greater than 85%.

69. The immunogenic composition of any preceding clause, wherein the RNA polynucleotide has a purity of greater than 85%.

70. The immunogenic composition of any preceding clause, wherein the lipid nanoparticle comprises 20-60 mol % ionizable cationic lipid, 5-25 mol % neutral lipid, 25-55 mol cholesterol, and 0.5-5 mol % PEG-modified lipid.

71. The immunogenic composition of any preceding clause, wherein the cationic lipid

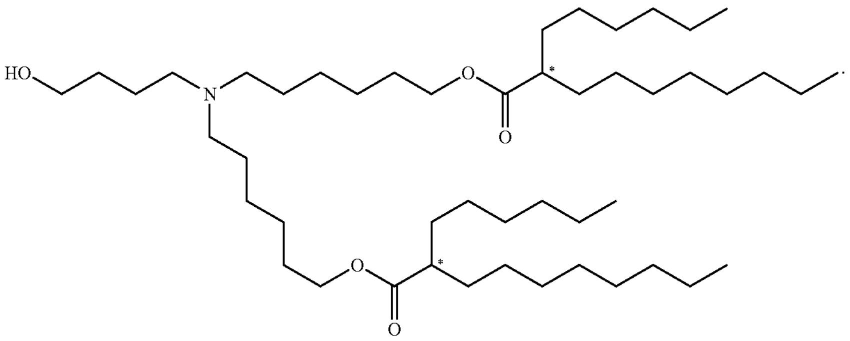

Asterisks (*) indicate chiral centers.

comprises:

72. The immunogenic composition of any preceding clause, wherein the PEG-modified lipid comprises:

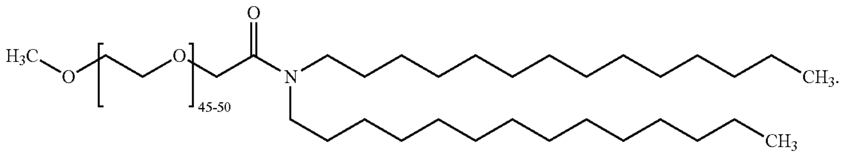

73. The immunogenic composition of any preceding clause, wherein the first antigen is HA from influenza A subtype H1 or an immunogenic fragment or variant thereof and the second antigen is HA from a different H1 strain to the first antigen or an immunogenic fragment or variant thereof.

74. The immunogenic composition of any preceding clause, wherein the first and second antigens are HA from influenza A subtype H3 or an immunogenic fragment or variant thereof and wherein both antigens are derived from different strains of H3 influenza virus.

75. The immunogenic composition of any preceding clause, wherein the first and second antigens are HA from influenza A subtype H1 or an immunogenic fragment or variant thereof and the third and fourth antigens are from influenza A subtype H3 or an immunogenic fragment or variant thereof and wherein the first and second antigens are derived from different strains of H1 virus and the third and fourth antigens are from different strains of H3 influenza virus.

76. The immunogenic composition of any preceding clause, wherein at least the first and second RNA polynucleotides are formulated in a single lipid nanoparticle.

77. The immunogenic composition of any preceding clause, wherein the first and second RNA polynucleotides are formulated in a single lipid nanoparticle.

78. The immunogenic composition of any preceding clause, wherein the first, second, and third RNA polynucleotides are formulated in a single lipid nanoparticle.

79. The immunogenic composition of any preceding clause, wherein the first, second, third, and fourth RNA polynucleotides are formulated in a single LNP.

80. The immunogenic composition of any one of clauses 36-75, wherein each of the RNA polynucleotides is formulated in a single LNP, wherein each single LNP encapsulates the RNA polynucleotide encoding one antigen.

81. The immunogenic composition of clause 80, wherein the first RNA polynucleotide is formulated in a first LNP; and the second RNA polynucleotide is formulated in a second LNP.

82. The immunogenic composition of clause 80, wherein the first RNA polynucleotide is formulated in a first LNP; the second RNA polynucleotide is formulated in a second LNP; and the third RNA polynucleotide is formulated in a third LNP.

83. The immunogenic composition of clause 80, wherein the first RNA polynucleotide is formulated in a first LNP; the second RNA polynucleotide is formulated in a second LNP; the third RNA polynucleotide is formulated in a third LNP; and the fourth RNA polynucleotide is formulated in a fourth LNP.

84. The immunogenic composition of clause 80, wherein the first RNA polynucleotide is formulated in a first LNP; the second RNA polynucleotide is formulated in a second LNP; the third RNA polynucleotide is formulated in a third LNP; the fourth RNA polynucleotide is formulated in a fourth LNP; and the fifth RNA polynucleotide is formulated in a fifth LNP.

85. The immunogenic composition of clause 80, wherein the first RNA polynucleotide is formulated in a first LNP; the second RNA polynucleotide is formulated in a second LNP; the third RNA polynucleotide is formulated in a third LNP; the fourth RNA polynucleotide is formulated in a fourth LNP; the fifth RNA polynucleotide is formulated in a fifth LNP; and the sixth RNA polynucleotide is formulated in a sixth LNP.

86. The immunogenic composition of clause 80, wherein the first RNA polynucleotide is formulated in a first LNP; the second RNA polynucleotide is formulated in a second LNP; third RNA polynucleotide is formulated in a third LNP; the fourth RNA polynucleotide is formulated in a fourth LNP; the fifth RNA polynucleotide is formulated in a fifth LNP; the sixth RNA polynucleotide is formulated in a sixth LNP; and the seventh RNA polynucleotide is formulated in a seventh LNP.

87. The immunogenic composition of clause 80, wherein the first RNA polynucleotide is formulated in a first LNP; the second RNA polynucleotide is formulated in a second LNP; the third RNA polynucleotide is formulated in a third LNP; the fourth RNA polynucleotide is formulated in a fourth LNP; the fifth RNA polynucleotide is formulated in a fifth LNP; the sixth RNA polynucleotide is formulated in a sixth LNP; the seventh RNA polynucleotide is formulated in a seventh LNP; and the eighth RNA polynucleotide is formulated in an eighth LNP.

88. The immunogenic composition of any preceding clause, for use in the eliciting an immune response against influenza.

89. A method of eliciting an immune response against influenza disease, comprising administering an effective amount of an immunogenic composition according to any one of clauses 36-79.

90. A method of purifying an RNA polynucleotide synthesized by in vitro transcription, comprising ultrafiltration and diafiltration.

91. The method according to clause 90, wherein the method does not comprise a chromatography step.

92. The method according to clause 90, wherein the purified RNA polynucleotide is substantially free of contaminants comprising short abortive RNA species, long abortive RNA species, double- stranded RNA (dsRNA), residual plasmid DNA, residual in vitro transcription enzymes, residual solvent and/or residual salt.

93. The method according to clause 90, wherein the residual plasmid DNA is ≤500 ng DNA/mg RNA.
94. The method according to clause 90, wherein purity of the purified mRNA is between about 60% and about 100%.
95. The method according to clause 90, further comprising encapsulating the RNA polynucleotide in a lipid nanoparticle.
96. The method according to clause 95, wherein the LNPs are buffer exchanged and concentrated via flat sheet cassette membranes.

What is claimed:

1. An immunogenic composition comprising:

(i) a first ribonucleic acid (RNA) polynucleotide comprising an open reading frame encoding a first antigen, said first antigen comprising a full-length hemagglutinin (HA) polypeptide;

(ii) a second RNA polynucleotide comprising an open reading frame encoding a second antigen, said second antigen comprising at least one influenza virus antigenic polypeptide or an immunogenic fragment thereof; and (ii) a third RNA polynucleotide comprising an open reading frame encoding a third antigen, said third antigen comprising at least one influenza virus antigenic polypeptide or an immunogenic fragment thereof, wherein the third antigen is from an influenza virus strain different from the influenza virus strain of the first and second antigens, wherein the first, second, and third RNA polynucleotides are formulated in one or more lipid nanoparticles, wherein each RNA polynucleotide comprises a 5' terminal cap, a 5' UTR comprising SEQ ID NO: 1, a 3' UTR comprising SEQ ID NO:2, wherein 100% of a uridine in SEQ ID NOs: 1 and 2 is replaced with a pseudouridine, and a 3' polyadenylation tail, and wherein the LNPs are purified and have a mean size of 40 nm to 150 nm.

2. The immunogenic composition of claim 1, wherein the first, second, and third RNA polynucleotides are formulated in a first, second, and third lipid nanoparticle, respectively.

3. The immunogenic composition of claim 1, further comprising: (iv) a fourth RNA polynucleotide comprising an open reading frame encoding a fourth antigen, said antigen comprising at least one influenza virus antigenic polypeptide or an immunogenic fragment thereof, wherein the fourth antigen is from influenza virus but is from a different strain of influenza virus to the first, second and third antigens.

4. The immunogenic composition of claim 3, wherein the first, second, third, and fourth RNA polynucleotides are formulated in one or more lipid nanoparticles.

5. The immunogenic composition of claim 1, wherein the first, second, and third RNA polynucleotides are present in about equal ratios.

6. The immunogenic composition of claim 1, wherein the open reading frame of each of the first, second, and third RNA polynucleotides comprises a modified nucleotide.

7. The immunogenic composition of claim 6, wherein the modified nucleotide is selected from the group consisting of pseudouridine, 1-methylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, and 2'-O-methyl uridine.

8. The immunogenic composition of claim 1, wherein the 5' terminal cap comprises:

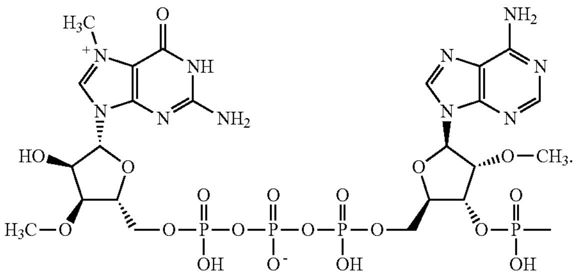

9. The immunogenic composition of claim 1, wherein the 3' polyadenylation tail comprises SEQ ID NO: 3.

10. The immunogenic composition of claim 1, wherein the first, second, and third RNA polynucleotides have an integrity greater than 85%.

11. The immunogenic composition of claim 1, wherein the first, second, and third RNA polynucleotides have a purity of greater than 85%.

12. The immunogenic composition of claim 1, wherein the lipid nanoparticle comprises 20-60 mol % ionizable cationic lipid, 5-25 mol % neutral lipid, 25-55 mol % cholesterol, and 0.5-5 mol % PEG-modified lipid.

13. The immunogenic composition of claim 12, wherein the cationic lipid comprises:

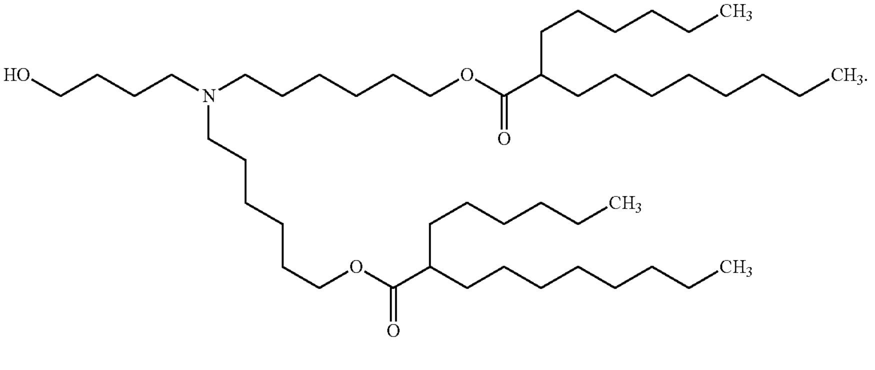 [SMILES: CCCCCCCCC(CCCCCC)C(=O)OCCCCCCN(CCCCO)CCCCCCOC(=O)C(CCCCCC)CCCCCCCC]

14. The immunogenic composition of claim 12, wherein the PEG-modified lipid comprises:

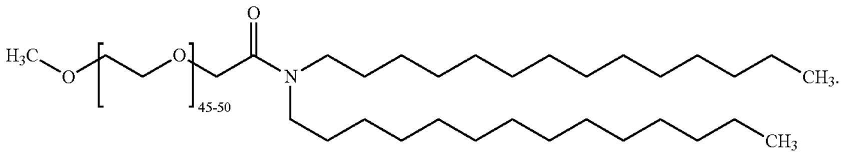

15. The immunogenic composition of claim 1, wherein the first antigen is HA from influenza A subtype H1 and the second antigen is HA from a different H1 strain to the first antigen or an immunogenic fragment or variant thereof.

16. The immunogenic composition of claim 1, wherein at least the first and second RNA polynucleotides are formulated in a single lipid nanoparticle.

17. The immunogenic composition of claim 1, wherein the first and second RNA polynucleotides are formulated in a single lipid nanoparticle.

18. The immunogenic composition of claim 1, wherein the first, second, and third RNA polynucleotides are formulated in a single lipid nanoparticle.

19. The immunogenic composition of claim 3, wherein the first RNA polynucleotide is formulated in a first lipid nanoparticle (LNP); the second RNA polynucleotide is formulated in a second LNP; the third RNA polynucleotide is formulated in a third LNP; and the fourth RNA polynucleotide is formulated in a fourth LNP.

20. The immunogenic composition of claim 1, for use in the eliciting an immune response against influenza in a subject.

21. A method of eliciting an immune response against influenza disease in a subject, comprising administering an effective amount of an immunogenic composition according to claim 1.

22. The immunogenic composition of claim 1, wherein the third antigen comprises a neuraminidase (NA) polypeptide.

* * * * *